(12) United States Patent
Seko et al.

(10) Patent No.: US 7,179,817 B2
(45) Date of Patent: Feb. 20, 2007

(54) CARBOXYLIC ACID DERIVATIVES AND DRUGS CONTAINING THE SAME AS THE ACTIVE INGREDIENT

(75) Inventors: Takuya Seko, Mishima-gun (JP); Masahiko Terakado, Mishima-gun (JP); Hiroshi Kohno, Mishima-gun (JP); Shinya Takahashi, Mishima-gun (JP)

(73) Assignee: ONO Pharmaceutical Co., Ltd., Osaka (JP)

( * ) Notice: Subject to any disclaimer, the term of this patent is extended or adjusted under 35 U.S.C. 154(b) by 416 days.

(21) Appl. No.: 10/477,106

(22) PCT Filed: May 9, 2002

(86) PCT No.: PCT/JP02/04520

§ 371 (c)(1),
(2), (4) Date: Nov. 10, 2003

(87) PCT Pub. No.: WO02/092068

PCT Pub. Date: Nov. 21, 2002

(65) Prior Publication Data

US 2004/0224941 A1 Nov. 11, 2004

(30) Foreign Application Priority Data

May 10, 2001 (JP) ............................. 2001-140458

(51) Int. Cl.
| C07D 211/78 | (2006.01) |
| C07D 211/70 | (2006.01) |
| C07D 5/02 | (2006.01) |
| C07C 317/00 | (2006.01) |
| C07C 331/00 | (2006.01) |
| C07C 49/23 | (2006.01) |
| C07F 265/30 | (2006.01) |

(52) U.S. Cl. ............... 514/277; 514/354; 514/400; 546/326; 546/334; 568/30; 568/77; 568/329; 568/1; 562/466; 544/166; 549/577

(58) Field of Classification Search ............ 514/277, 514/354, 400; 546/326, 334; 568/30, 77, 568/329, 1; 562/466; 544/166; 549/577
See application file for complete search history.

(56) References Cited

U.S. PATENT DOCUMENTS 5,872,280 A 2/1999 Abram et al.

FOREIGN PATENT DOCUMENTS

JP 2-218654 A 8/1990

OTHER PUBLICATIONS

Hcaplus 132:44282, Journal of Chromatography, A (1999), 859(1), 13-21, Iwata, Tetsuo et. al.*
D. Meyer Zu Heringdorf, et al., Stimulation of intracellular sphingosine-1-phosphate production by G-protein-coupled sphingosine-1-phosphate receptors, Eur. J. Pharmacol., Mar. 2001, vol. 414, pp. 145 to 154.
K. Sato, et al., Differential roles of Edg-1, and Edg-5, sphingosine 1-phosphate receptors, in the signaling pathways in c6 glioma cells, Brain. Res. Mol. Brain. Res., 2000, vol. 85, pp. 151 to 160.

* cited by examiner

Primary Examiner—Thomas McKenzie
Assistant Examiner—Binta Robinson
(74) Attorney, Agent, or Firm—Sughrue Mion, PLLC

(57) ABSTRACT

Compounds represented by formula (I), prodrugs thereof and salts thereof, and pharmaceutical compositions comprising the same as an active ingredient (wherein each symbol has the meaning as defined in the specification.).

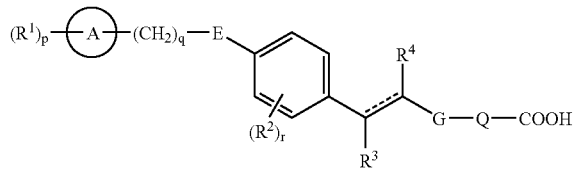

Because of having an EDG-1 agonism, the compounds represented by formula (I) are useful in preventing and/or treating peripheral arterial disease such as arteriosclerosis obliterans, thromboangiitis obliterans, Buerger's disease or diabetic neuropathy, sepsis, angiitis, nephritis, pneumonia, stroke, myocardial infarction, edematous state, atherosclerosis, varicosity such as hemorrhoid, anal fissure or fistula ani, dissecting aneurysm of the aorta, angina, DIC, pleuritis, congestive heart failure, multiple organ failure, bedsore, burn, chronic ulcerative colitis, Crohn's disease, heart transplantation, renal transplantation, dermal graft, liver transplantation, osteoporosis, pulmonary fibrosis, interstitial pneumonia, chronic hepatitis, liver cirrhosis, chronic renal failure, or glomerular sclerosis.

14 Claims, No Drawings

CARBOXYLIC ACID DERIVATIVES AND DRUGS CONTAINING THE SAME AS THE ACTIVE INGREDIENT

TECHNICAL FIELD

The present invention relates to carboxylic acid derivatives and pharmaceutical compositions comprising the same as an active ingredient. More specifically, the present invention relates to (1) carboxylic acid derivatives represented by formula (I)

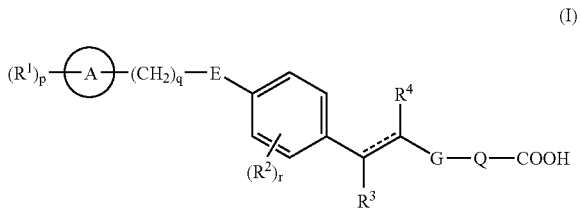

prodrugs thereof, non-toxic salts thereof, (2) the process for preparation thereof, and (3) EDG-1 agonist comprising carboxylic acid derivatives represented by above formula (I), prodrugs thereof and non-toxic salts thereof as an active ingredient.

BACKGROUND ART

In recent years, it is known that various lipid mediators such as eicosanoid, platelet activating factor (PAF) and lysophosphatidic acid (LPA) are produced by the activity of phospholipase from cell membranes. Moreover, sphingosine 1-phosphate (hereinafter abbreviated as S1P) is a lipid which is produced by metabolic turnover of sphingolipid, acts as a mediator for signal transduction and delivers various signals into cells. Firstly, it was reported that S1P may act as an intracellular second messenger, then, by intracellular microinjection of S1P, it was revealed that S1P has a biological action in cell. However, intracellular substance affected directly by S1P has never identified. On the other hand, the existence of five subtypes of S1P receptor in cell membranes has been disclosed recently and it is gradually proved that their physiological activities are via S1P receptor. Five subtypes of S1P receptor are called EDG (Endothelial differentiation gene)-1, 3, 5, 6 and 8, respectively. They as well as EDG-2, 4 and 7 which are LPA receptors are 7-transmembrane G protein-coupled receptor (GPCR) and are called EDG receptor family. These discoveries originate with a report which was reported by Hia et al. in 1990 that EDG-1 is an orphan receptor which is induced by Phorbol 12-myristate 13-acetate (PMA) in human umbilical vein endothelial cells (HUVEC).

S1P receptors to which S1P binds deliver signals into cells via G-protein-coupled receptors. Gs, Gi, Gq are known as G-proteins to which S1P receptor can couple, and it is considered that the receptor is responsible for an increase of cell proliferation, an induction of cell chemotaxis, adversely, a decrease of cell proliferation, or an inhibition of cell chemotaxis. Furthermore, since systems via ERK signal which active p42MAPK/ERK2 operate in the lower of G-protein, it has been known that S1P receptors deliver various signals.

Inhibition of migration of smooth muscle cell or cancer cell, regulation of blood pressure, platelet aggregation and so on are known as pharmacological action of S1P. Recently, it is revealed that S1P plays an important role for angiogenesis. It was reported by Menq-Jer Lee et al. that S1P induced cell survival, formation of adherens junctions, morphogenesis of microvascular in HUBEC (Cell 99, 301–312 (1999)). Moreover, they reported that, in vitro and in vivo, S1P has a synergetic effect with fibroblast growth factor (FGF) or vascular endothelial growth factor (VEGF) for angiosenesis. It was revealed by OK-Hee Lee et al. that S1P stimulated DNA synthesis and chemotactic motility of HUVECs in vitro, and S1P induced angiogenesis by itself in vivo (Biochem. Biophys. Res. Commun. 264, 743–750 (1999)). These results indicated that an induction of angiogenesis via S1P receptor is one of the biological actions of S1P in the body.

Recently, EDG-1 knock-out mice were prepared (Yujing Liu et al, J. Clin. Inves. 2000) and it is indicated that S1P induced angiogenesis is the action via EDG-1 because abnormal angiogenesis lead to embryonic lethality of the mice. Therefore, it is suggested that EDG-1 agonist is used as a treating agent for disease caused by anangioplasia. For example, it is used as an agent for treatment of peripheral arterial disease such as arteriosclerosis obliterans, thromboangiitis obliterans, Buerger's disease or diabetic neuropathy, varicosity such as hemorrhoid, anal fissure or fistula ani, dissecting aneurysm of the aorta, sepsis, angiitis, nephritis or pneumonia, moreover, for prevention and/or treatment of various edematous state caused by ischemia of various organ or increase of the blood permeability, for example, myocardial infarction, stroke, angina, DIC (Disseminated intravascular coagulation), pleuritis, congestive heart failure or multiple organ failure. Furthermore, because angiogenesis closely relates to osteogenesis, it is used a treating agent for abnormal bone metabolism, for example, osteoprosis. Furthermore, because it is indicated that EDG-1 may inhibit chemotaxis of vascular smooth muscle in knock-out mouse, EDG-1 agonist is used as an agent for prevention and/or treatment for arterial sclerosis. Furthermore, it is used as an agent for prevention and/or treatment for bedsore, burn, chronic ulcerative colitis or Crohn's disease. It is used as prognostic or preoperative activator of blood vessel in various organ transplant, for example, heart transplantation, renal transplantation, dermal graft or liver transplantation.

Because it was revealed that S1P is effective for bleomycin induced lung fibrosis in mice (ref. WO01/03739), it is used as an agent for prevention and/or treatment for pulmonary fibrosis, interstitial pneumonia, chronic hepatitis, liver cirrhosis, chronic renal failure or glomerular sclerosis.

Therefore, it is considered that EDG-1 agonist is used as an agent for prevention and/or treatment for peripheral arterial disease such as arteriosclerosis obliterans, thromboangiitis obliterans, Buerger's disease or diabetic neuropathy, sepsis, angiitis, nephritis, pneumonia, stroke, myocardial infarction, edematous state, atherosclerosis, varicosity such as hemorrhoid, anal fissure or fistula ani, dissecting aneurysm of the aorta, angina, DIC, pleuritis, congestive heart failure, multiple organ failure, bedsore, burn, chronic ulcerative colitis, Crohn's disease, heart transplantation, renal transplantation, dermal graft, liver transplantation, osteoporosis, pulmonary fibrosis, interstitial pneumonia, chronic hepatitis, liver cirrhosis, chronic renal failure, or glomerular sclerosis.

The existence of a compound having EDG-1 agonistic action has never known until today.

On the other hand, in the specification of EP791576, it is described that benzoic acid derivatives represented by formula (X)

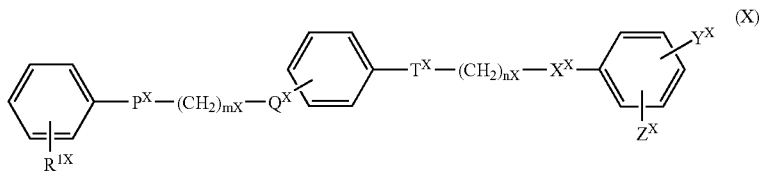

[wherein $R^{1X}$ is hydrogene, alkyl having up to six carbon atoms or substituted phenyl;

$P^X$ and $Q^X$ are independently oxygen, sulfur or a bond;

$X^X$ is oxygen, sulfur or —CONH—;

$T^X$ is ethylene, oxygen, sulfur or a bond;

$Y^X$ is —COOH, —NHSO$_2$R$^{3X}$ or —CONHSO$_2$R$^{3X}$;

wherein $R^{2X}$ is hydrogen, halogen, trifluoromethyl, trifluoromethoxy, nitro, cyano or alkyl or alkoxy;

$Z^X$ is —COOH, COR$^{4X}$, —CO(CH$_2$)$_{pX}$CO$_2$H, —O(CH$_2$)$_{pX}$CO$_2$H, —S(CH$_2$)$_{pX}$CO$_2$H, NO$_2$, —CONHW$^X$CO$_2$H or —NHW$^X$CO$_2$H;

wherein $R^{2X}$ has the above mentioned meaning;

$R^{3X}$ is trifluoromethyl, alkyl or optionally substituted phenyl;

$R^{4X}$ is W$^X$CO$_2$H or alkyl;

pX is an integer from 0 to 5;

$W^X$ is phenylene, alkylene having up to 8 carbon atoms which is optionally substituted by alkyl or cycloalkyl each having up to 6 carbon atoms or —CO(CH$_2$)$_{qX}$— or —(CH$_2$)$_{qX}$—;

wherein qX is an integer from 0 to 5;

mX is an integer from 0 to 6;

nX is an integer from 0 to 4.]

and salts thereof are used as inhibitor of luekotriene.

Moreover, in the specification of JP02-218654, it is described that benzoic acid derivatives represented by formula (Y)

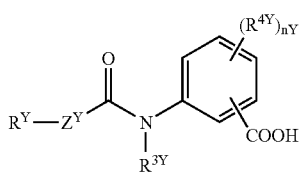

[wherein $R^Y$ is a group represented by formula

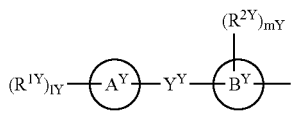

(wherein $R^{1Y}$ is hydrogen, C1–8 alkyl, C1–8 alkoxy, halogen or trifluoromethyl;

IY is an integer from 1 to 5;

$A^Y$ is 4–10 membered carbocyclic ring or cyclic hetero ring;

$Y^Y$ is a group represented by formula

—O—AlK—O—,

—AlK—O—, or

—AlK—

(wherein AlK is C1–8 alkylene.);

$B^Y$ is 4–10 membered mono-carbocyclic ring or mono-cyclic hetero ring;

$R^{2Y}$ is hydrogene, C1–4 alkyl, C1–4 alkoxy, halogen, trifluoromethyl or C2–5 alkanoyl;

mY is an integer from 1 to 4.);

$Z^Y$ is a bond, C1–6 alkylene or C2–6 alkenylene;

$R^{3Y}$ is hydrogen, C1–4 alkyl, phenyl or C1–4 alkyl substituted by phenyl;

$R^{4Y}$ is hydrogen, C1–4 alkyl, C1–4 alkoxy, halogen, trifluoromethyl, hydroxy or nitro;

nY is an integer from 1 to 4.]

and non-toxic salts thereof are used as reverse transcriptase inhibitor.

DISCLOSURE OF THE INVENTION

The present inventors have made investigations so as to find a compound having superior agonistic action for EDG-1 and extremely safe. Consequently, the inventors have found that the purpose has been achieved by carboxylic acid derivative represented by formula (I).

The carboxylic acid derivatives represented by formula (I), the prodrugs thereof and the non-toxic salts are new compounds which have never prepared before.

The present invention relates to

1) EDG-1 agonist which comprises, as an active ingredient, carboxylic acid derivatives represented by formula (I)

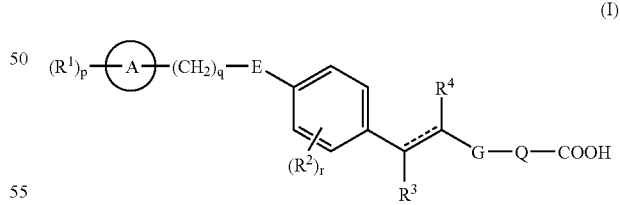

wherein $R^1$ is C1–8 alkyl, C1–8 alkoxy, halogen atom, nitro or trifluoromethyl, ring A is C5–7 mono-carbocyclic ring or 5–7 membered mono-cyclic hetero ring containing 1–2 nitrogen atoms, one oxygen atom and/or one sulfur atom, E is —CH$_2$—, —O—, —S— or —NR$^6$— (wherein $R^6$ is hydrogen or C1–8 alkyl.), $R^2$ is C1–8 alkyl, C1–8 alkoxy, halogen atom, nitro or trifluoromethyl, $R^3$ is hydrogen or C1–8 alkyl,
$R^4$ is hydrogen or C1–8 alkyl,
$R^2$ and $R^4$ taken together form —CH$_2$—CH$_2$— or —CH=CH—,
G is —CONR$^7$—, —NR$^7$CO—, —SO$_2$NR$^7$—, —NR$^7$SO$_2$—, —CH$_2$NR$^7$— or —NR$^7$CH$_2$— (wherein $R^7$ is hydrogen, C1–8 alkyl, Cyc1 or C1–8 alkyl substituted by Cyc1, Cyc1 is C5–7 mono-carbocyclic ring or 5–7 membered mono-cyclic hetero ring containing 1–2 nitrogen atoms, one oxygen atom and/or one sulfur atom.),
Q is C1–4 alkylene or

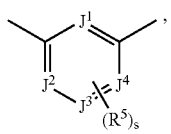

$J^1$, $J^2$, $J^3$ and $J^4$ are each independently carbon atom or nitrogen atom (with the proviso that the number of nitrogen is less than two.),
$R^5$ is
(1) C1–8 alkyl,
(2) halogen atom,
(3) nitro,
(4) cyano,
(5) trifluoromethyl,
(6) trifluoromethoxy,
(7) phenyl,
(8) tetrazolyl,
(9) —OR$^9$,
(10) —SR$^{10}$,
(11) —COOR$^{11}$,
(12) —NR$^{12}$R$^{13}$,
(13) —CONR$^{14}$R$^{15}$,
(14) —SO$_2$NR$^{16}$R$^{17}$,
(15) —NR$^{18}$COR$^{19}$,
(16) —NR$^{20}$SO$_2$R$^{21}$,
(17) —SO$_2$R$^{22}$ or
(18) —OP(O)(OR$^{23}$)$_2$,
(wherein $R^9$–$R^{18}$, $R^{20}$ and $R^{23}$ are each independently hydrogen, C1–8 alkyl, Cyc2 or C1–8 alkyl substituted by Cyc2,
$R^{12}$ and $R^{13}$, $R^{14}$ and $R^{15}$, $R^{16}$ and $R^{17}$ together with nitrogen atom to which they are attached, form 5–7 membered mono-cyclic hetero ring containing 1–2 nitrogen atoms, one oxygen atom and/or one sulfur atom (the hetero ring may be optionally substituted by C1–8 alkyl, hydroxy or aimno.)
$R^{19}$ and $R^{21}$ are each independently C1–8 alkyl, Cyc2 or C1–8 alkyl substituted by Cyc2,
$R^{22}$ is hydroxy, C1–8 alkyl, Cyc2 or C1–8 alkyl substituted by Cyc2, Cyc2 is C5–7 mono-carbocyclic ring or 5–7 membered mono-cyclic hetero ring containing 1–2 nitrogen atoms, one oxygen atom and/or one sulfur atom.),
wherein, when Q is

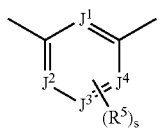

and $J^2$ is carbon atom substituted by $R^5$, G may be

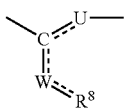

(wherein U is oxygen atom, nitrogen atom or sulfur atom,
W is carbon atom or nitrogen atom,
$R^8$ and $R^5$, which bonds $J^2$, taken together form bond, carbon atom or nitrogen atom.),
p is 0 or an integer of 1–5,
q is an integer of 4–6,
r is 0 or an integer of 1–4,
s is 0 or an integer of 1–4,

- - - - - is single bond or double bond,
prodrugs thereof or non-toxic salts.
2) carboxylic acid derivatives represented by formula (I)

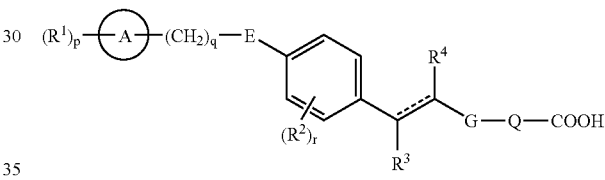

(I)

(wherein all symbols represent the same meanings as defined hereinbefore.), prodrugs thereof or non-toxic salts, and
3) the process for preparation thereof.

DETAILED DESCRIPTION OF THE INVENTION

In the present invention, C1–8 alkyl means methyl, ethyl, propyl, butyl, pentyl, hexyl, heptyl, octyl or isomeric groups thereof.

In the present invention, C1–8 alkoxy means methoxy, ethoxy, propoxy, butoxy, pentyloxy, hexyloxy, heptyloxy, octyloxy or isomeric groups thereof.

In the present invention, C1–4 alkylene means methylene, ethylene, trimethylene, tetramethylene or isomeric groups thereof.

In the present invention, halogen is chlorine, bromine, fluorine or iodine.

In the present invention, C5–7 mono-carbocyclic ring means C5–7 mono-carbocyclic aryl or partially saturated one. It is, for example, cyclopentane, cyclohexane, cycloheptane, cyclopentene, cyclohexene, cycloheptene, cyclopentadiene, cyclohexadiene, cycloheptadiene or benzene etc.

In the present invention, 5–7 membered mono-cyclic hetero ring containing 1–2 nitrogen atom(s), one oxygen atom and/or one sulfur atom means 5–7 membered mono-cyclic hetero aryl containing 1–2 nitrogen atom(s), one oxygen atom and/or one sulfur atom or partially saturated one. It is, for example, pyrrole, imidazole, pyrazole, pyridine, pyrazine, pyrimidine, pyridazine, azepine, diazepine, furan, pyran, oxepine, thiophene, thiain (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiadiazole, tetrahydrothiadiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine or thiomorpholine etc.

In the present invention, 5–7 membered mono-cyclic hetero ring containing 1–2 nitrogen atoms, one oxygen atom and/or one sulfur atom formed together with nitrogen atom to which they are attached, means 5–7 membered mono-cyclic hetero aryl containing 1–2 nitrogen atom(s), one oxygen atom and/or one sulfur atom, fully or partially saturated one. It is, for example, pyrrole, imidazole, pyrazole, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole, tetrahydroisoxazole, tetrahydrothiazole, tetrahydroisothiazole, dihydrooxadiazole, tetrahydrooxadiazole, dihydrothiadiazole, tetrahydrothiadiazole, tetrahydrooxadiazine, tetrahydrothiadiazine, tetrahydrooxadiazepine, perhydrooxazepine, perhydrooxadiazepine, tetrahydrothiadiazepine, perhydrothiazepine, perhydrothiadiazepine, morpholine, or thiomorpholine etc.

Unless otherwise specified, all isomers are included in the present invention. For example, alkyl, alkoxy and alkylene groups include straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomer (D-, L-, d-, l-isomer), polar compounds generated by chromatographic separation (more polar compound, less polar compound), equilibrium compounds, mixtures thereof at voluntary ratios and racemic mixtures are also included in the present invention.

The compounds represented by formula (I) may be converted into the corresponding salts by conventional means.

In present invention, The non-toxic salts include, for example, salts of alkali metals, salts of alkaline earth metals, ammonium salts, salts of amines or acid addition salts etc.

The compounds of the present invention represented by formula (I) may be converted into the corresponding salts by conventional means. Non-toxic salts or water-soluble salts are preferred. Suitable salts, for example, include: salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine).

As acid addition salts, non-toxic and water-soluble salts are preferred. Suitable acid addition salts, for example, include: salts of inorganic acids e.g. hydrochloride, hydrobromide, hydroiodide, sulfate, phosphate, nitrate; salts of organic acids e.g. acetate, lactate, tartrate, benzoate, citrate, methanesulfonate, ethanesulfonate, benzenesulfonate, toluenesulfonate, isethionate, glucuronate, gluconate.

The compounds of the present invention represented by formula (I) and salts thereof may be converted into solvates by conventional means.

Non-toxic and water-soluble solvates are preferred. Suitable solvates include, for example, solvates such as solvent of water or alcohol (for example, ethanol etc.).

As prodrugs in the present invention, compounds which may improve bioavailability and biomembrane permeability are preferable. Since the compounds of the present invention represented by formula (I) have carboxyl, prodrugs include compounds which are cleaved or oxidized in body to be converted into compounds having carboxyl.

The compounds which are cleaved in body to be converted into compounds having carboxyl include carboxylate ester derivatives or carboxylic amide derivatives.

The compounds which oxidized in body to be converted into compounds having carboxyl include alcohol derivatives.

The prodrugs of the compounds of the present invention represented by formula (I) include the compounds represented by formula (IA)

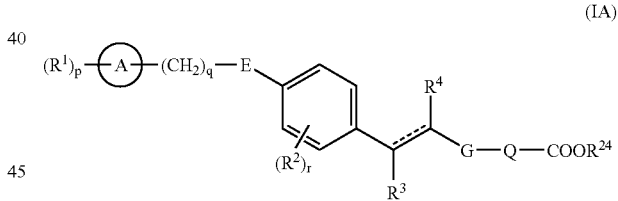

(IA)

(wherein $R^{24}$ is C1–8 alkyl or C1–8 alkyl substituted by 1–2 of hydroxyl or amino, and the other symbol have the same meanings as defined hereinbefore.), the compounds represented by formula (IB)

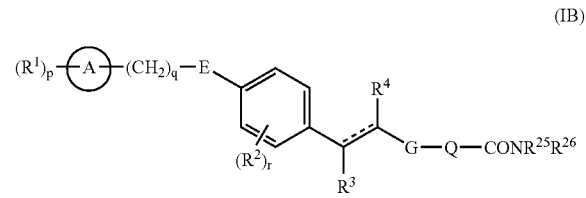

(IB)

(wherein $R^{25}$ and $R^{26}$ are, each independently, hydroxy, C1–8 alkyl or C1–8 alkyl substituted by 1–2 of hydroxyl or amino, and the other symbol have the same meanings as defined hereinbefore.), the compounds represented by formula (IC)

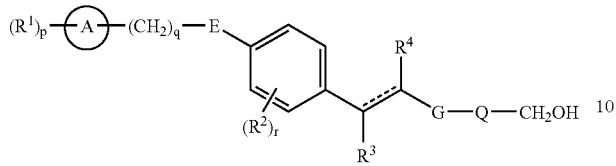

(wherein all symbol have the same meanings as defined hereinbefore.), the compounds represented by formula (ID)

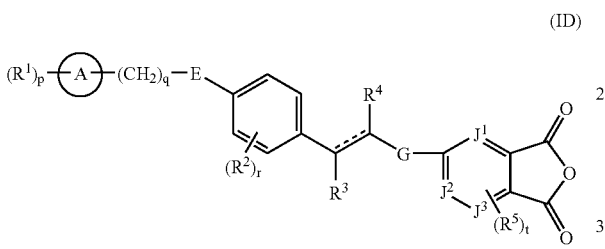

(wherein t is 0 or an integer of 1–3, and the other symbol have the same meanings as defined hereinbefore.), concretely.

In formula (I), 0 or 1 is preferable as p and especially 0.

In formula (I), C1–8 alkyl or C1–8 alkoxy is preferable as $R^1$ and especially methyl or methoxy.

In formula (I), C5–7 mono-carbocyclic ring or 5–7 membered mono-cyclic hetero ring containing 1–2 nitrogen atom(s), one oxygen atom and/or one sulfur atom is preferable as ring A and especially benzene or thiophene.

In formula (I), 5 or 6 is preferable as q and especially 5.

In formula (I), —O—, —S— or —$NR^6$— is preferable as E and especially —O—.

In formula (I), 0 or 1 is preferable as r and especially 0.

In formula (I), C1–8 alkyl, C1–8 alkoxy or halogen is preferable as $R^2$ and especially methyl, methoxy or fluorine.

In formula (I), hydrogen is preferable as $R^3$.

In formula (I), hydrogen is preferable as $R^4$.

In formula (I), —$CONR^7$—, —$NR^7CO$—, —$NR^7SO_2$—, —$CH_2NR^7$— or —$NR^7CH_2$— is preferable as G and especially —$CONR^7$—, —$NR^7CO$—, —$CH_2NR^7$— or —$NR^7CH_2$—.

In formula (I), hydrogen or C1–8 alkyl is preferable as $R^7$ and especially hydrogen.

In formula (I), hydrogen or C1–4 alkylene or

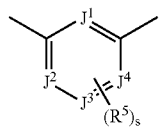

is preferable as Q and especially methylene, ethylene, phenylene or pyridinylene.

In formula (I), carbon atom or nitrogen atom is preferable as $J^1$, $J^2$, $J^3$ and $J^4$, and especially compounds wherein $J^1$, $J^2$, $J^3$ and $J^4$ are carbon atom or wherein $J^1$ is nitrogen atom and $J^2$, $J^3$ and $J^4$ are carbon atom are preferable.

In formula (I), 0 or 1 is preferable as s and especially 1.

In formula (I), halogen or —$COOR^{11}$ is preferable as $R^5$ and especially chlorine or —COOH. Moreover, $R^5$ which binds $J^4$ is preferable.

In the compounds of the present invention represented by formula (I), preferably compounds are the carboxylic acid derivatives represented by formula (I-1)

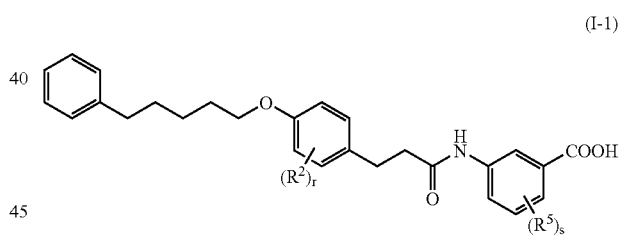

(wherein $R^2$, r, $R^5$ and s have the same meanings as defined hereinbefore.), formula (I-2)

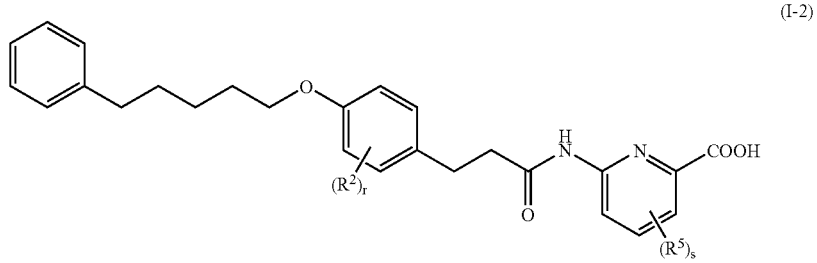

(wherein R², r, R⁵ and s have the same meanings as defined hereinbefore.), formula (I-3)

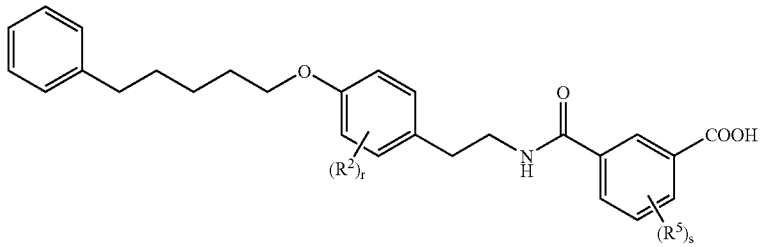

(wherein R², r, R⁵ and s have the same meanings as defined hereinbefore.), formula (I-4)

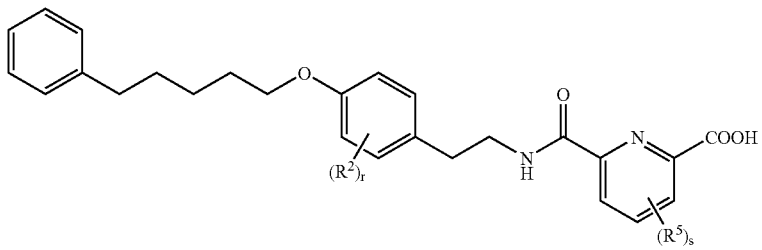

(wherein R², r, R⁵ and s have the same meanings as defined hereinbefore.), formula (I-5)

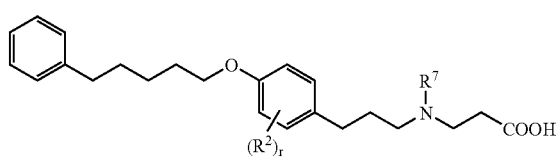

(wherein R², r and R⁷ have the same meanings as defined hereinbefore.), formula (I-6)

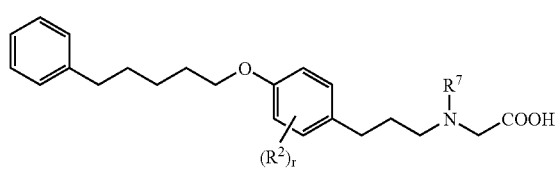

(wherein R², r and R⁷ have the same meanings as defined hereinbefore.), or formula (I-7)

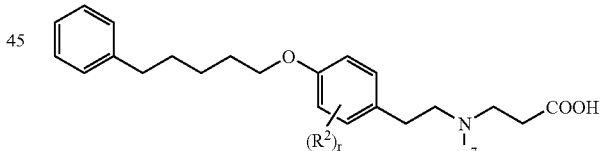

(wherein R², r and R⁷ have the same meanings as defined hereinbefore.), the prodrugs thereof or the non-toxic salts thereof.

The specific compounds in the present invention include the compounds in table 1–7, the example compounds, the prodrugs or the non-toxic salts.

TABLE 1

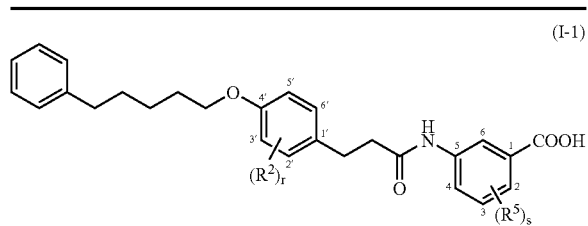
(I-1)

| No. | r | R² | s | R⁵ |
|---|---|---|---|---|
| 1 | 0 | — | 0 | — |
| 2 | 0 | — | 1 | 2-Cl |
| 3 | 0 | — | 1 | 2-F |
| 4 | 0 | — | 1 | 2-COOH |
| 5 | 0 | — | 1 | 3-Cl |
| 6 | 0 | — | 1 | 3-F |
| 7 | 0 | — | 1 | 3-COOH |
| 8 | 0 | — | 1 | 4-Cl |
| 9 | 0 | — | 1 | 4-F |
| 10 | 0 | — | 1 | 4-COOH |
| 11 | 0 | — | 1 | 6-Cl |
| 12 | 0 | — | 1 | 6-F |
| 13 | 0 | — | 1 | 6-COOH |
| 14 | 1 | 3'-OCH₃ | 1 | 2-Cl |
| 15 | 1 | 3'-OCH₃ | 1 | 2-F |
| 16 | 1 | 3'-OCH₃ | 1 | 2-COOH |
| 17 | 1 | 2'-OCH₃ | 1 | 2-Cl |
| 18 | 1 | 2'-OCH₃ | 1 | 2-F |
| 19 | 1 | 2'-OCH₃ | 1 | 2-COOH |
| 20 | 1 | 3'-CH₃ | 1 | 2-Cl |
| 21 | 1 | 3'-CH₃ | 1 | 2-F |
| 22 | 1 | 3'-CH₃ | 1 | 2-COOH |
| 23 | 1 | 2'-CH₃ | 1 | 2-Cl |
| 24 | 1 | 2'-CH₃ | 1 | 2-F |
| 25 | 1 | 2'-CH₃ | 1 | 2-COOH |
| 26 | 1 | 3'-Cl | 1 | 2-Cl |
| 27 | 1 | 3'-Cl | 1 | 2-F |
| 28 | 1 | 3'-Cl | 1 | 2-COOH |
| 29 | 1 | 2'-Cl | 1 | 2-Cl |
| 30 | 1 | 2'-Cl | 1 | 2-F |
| 31 | 1 | 2'-Cl | 1 | 2-COOH |

TABLE 2

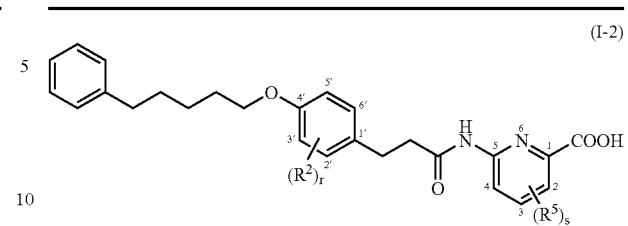
(I-2)

| No. | r | R² | s | R⁵ |
|---|---|---|---|---|
| 1 | 0 | — | 0 | — |
| 2 | 0 | — | 1 | 2-Cl |
| 3 | 0 | — | 1 | 2-F |
| 4 | 0 | — | 1 | 2-COOH |
| 5 | 0 | — | 1 | 3-Cl |
| 6 | 0 | — | 1 | 3-F |
| 7 | 0 | — | 1 | 3-COOH |
| 8 | 0 | — | 1 | 4-Cl |
| 9 | 0 | — | 1 | 4-F |
| 10 | 0 | — | 1 | 4-COOH |
| 11 | 0 | — | 2 | 2,3-di-Cl |
| 12 | 0 | — | 2 | 2,3-di-F |
| 13 | 0 | — | 2 | 2,4-di-Cl |
| 14 | 1 | 3'-OCH₃ | 1 | 2-Cl |
| 15 | 1 | 3'-OCH₃ | 1 | 2-F |
| 16 | 1 | 3'-OCH₃ | 1 | 2-COOH |
| 17 | 1 | 2'-OCH₃ | 1 | 2-Cl |
| 18 | 1 | 2'-OCH₃ | 1 | 2-F |
| 19 | 1 | 2'-OCH₃ | 1 | 2-COOH |
| 20 | 1 | 3'-CH₃ | 1 | 2-Cl |
| 21 | 1 | 3'-CH₃ | 1 | 2-F |
| 22 | 1 | 3'-CH₃ | 1 | 2-COOH |
| 23 | 1 | 2'-CH₃ | 1 | 2-Cl |
| 24 | 1 | 2'-CH₃ | 1 | 2-F |
| 25 | 1 | 2'-CH₃ | 1 | 2-COOH |
| 26 | 1 | 3'-Cl | 1 | 2-Cl |
| 27 | 1 | 3'-Cl | 1 | 2-F |
| 28 | 1 | 3'-Cl | 1 | 2-COOH |
| 29 | 1 | 2'-Cl | 1 | 2-Cl |
| 30 | 1 | 2'-Cl | 1 | 2-F |
| 31 | 1 | 2'-Cl | 1 | 2-COOH |

TABLE 3

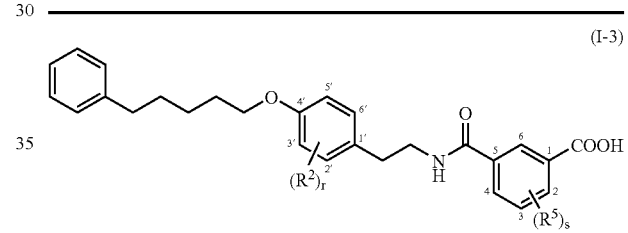
(I-3)

| No. | r | R² | s | R⁵ |
|---|---|---|---|---|
| 1 | 0 | — | 0 | — |
| 2 | 0 | — | 1 | 2-Cl |
| 3 | 0 | — | 1 | 2-F |
| 4 | 0 | — | 1 | 2-COOH |
| 5 | 0 | — | 1 | 3-Cl |
| 6 | 0 | — | 1 | 3-F |
| 7 | 0 | — | 1 | 3-COOH |
| 8 | 0 | — | 1 | 4-Cl |
| 9 | 0 | — | 1 | 4-F |
| 10 | 0 | — | 1 | 4-COOH |
| 11 | 0 | — | 1 | 6-Cl |
| 12 | 0 | — | 1 | 6-F |
| 13 | 0 | — | 1 | 6-COOH |
| 14 | 1 | 3'-OCH₃ | 1 | 2-Cl |
| 15 | 1 | 3'-OCH₃ | 1 | 2-F |
| 16 | 1 | 3'-OCH₃ | 1 | 2-COOH |
| 17 | 1 | 2'-OCH₃ | 1 | 2-Cl |
| 18 | 1 | 2'-OCH₃ | 1 | 2-F |
| 19 | 1 | 2'-OCH₃ | 1 | 2-COOH |
| 20 | 1 | 3'-CH₃ | 1 | 2-Cl |
| 21 | 1 | 3'-CH₃ | 1 | 2-F |
| 22 | 1 | 3'-CH₃ | 1 | 2-COOH |
| 23 | 1 | 2'-CH₃ | 1 | 2-Cl |
| 24 | 1 | 2'-CH₃ | 1 | 2-F |
| 25 | 1 | 2'-CH₃ | 1 | 2-COOH |
| 26 | 1 | 3'-Cl | 1 | 2-Cl |
| 27 | 1 | 3'-Cl | 1 | 2-F |
| 28 | 1 | 3'-Cl | 1 | 2-COOH |
| 29 | 1 | 2'-Cl | 1 | 2-Cl |
| 30 | 1 | 2'-Cl | 1 | 2-F |
| 31 | 1 | 2'-Cl | 1 | 2-COOH |

TABLE 4

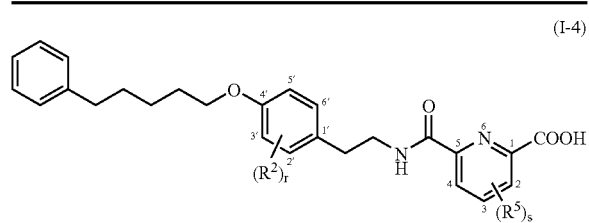
(I-4)

| No. | r | R² | s | R⁵ |
|---|---|---|---|---|
| 1 | 0 | — | 0 | — |
| 2 | 0 | — | 1 | 2-Cl |
| 3 | 0 | — | 1 | 2-F |
| 4 | 0 | — | 1 | 2-COOH |
| 5 | 0 | — | 1 | 3-Cl |
| 6 | 0 | — | 1 | 3-F |
| 7 | 0 | — | 1 | 3-COOH |
| 8 | 0 | — | 1 | 4-Cl |
| 9 | 0 | — | 1 | 4-F |
| 10 | 0 | — | 1 | 4-COOH |
| 11 | 0 | — | 2 | 2,3-di-Cl |
| 12 | 0 | — | 2 | 2,3-di-F |
| 13 | 0 | — | 2 | 2,4-di-Cl |
| 14 | 1 | 3'-OCH₃ | 1 | 2-Cl |
| 15 | 1 | 3'-OCH₃ | 1 | 2-F |
| 16 | 1 | 3'-OCH₃ | 1 | 2-COOH |
| 17 | 1 | 2'-OCH₃ | 1 | 2-Cl |
| 18 | 1 | 2'-OCH₃ | 1 | 2-F |
| 19 | 1 | 2'-OCH₃ | 1 | 2-COOH |
| 20 | 1 | 3'-CH₃ | 1 | 2-Cl |
| 21 | 1 | 3'-CH₃ | 1 | 2-F |
| 22 | 1 | 3'-CH₃ | 1 | 2-COOH |
| 23 | 1 | 2'-CH₃ | 1 | 2-Cl |
| 24 | 1 | 2'-CH₃ | 1 | 2-F |
| 25 | 1 | 2'-CH₃ | 1 | 2-COOH |
| 26 | 1 | 3'-Cl | 1 | 2-Cl |
| 27 | 1 | 3'-Cl | 1 | 2-F |
| 28 | 1 | 3'-Cl | 1 | 2-COOH |
| 29 | 1 | 2'-Cl | 1 | 2-Cl |
| 30 | 1 | 2'-Cl | 1 | 2-F |
| 31 | 1 | 2'-Cl | 1 | 2-COOH |

TABLE 5

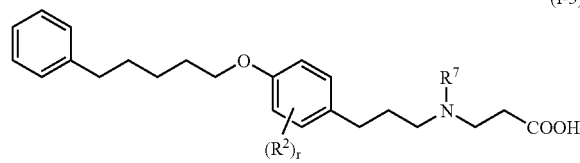
(I-5)

| No. | r | R² | R⁷ |
|---|---|---|---|
| 1 | 0 | — | H |
| 2 | 1 | 3'-OCH₃ | H |
| 3 | 1 | 2'-OCH₃ | H |
| 4 | 1 | 3'-CH₃ | H |
| 5 | 1 | 2'-CH₃ | H |
| 6 | 1 | 3'-Cl | H |
| 7 | 1 | 2'-Cl | H |
| 8 | 0 | — | CH₃ |
| 9 | 1 | 3'-OCH₃ | CH₃ |
| 10 | 1 | 2'-OCH₃ | CH₃ |
| 11 | 1 | 3'-CH₃ | CH₃ |
| 12 | 1 | 2'-CH₃ | CH₃ |
| 13 | 1 | 3'-Cl | CH₃ |
| 14 | 1 | 2'-Cl | CH₃ |

TABLE 6

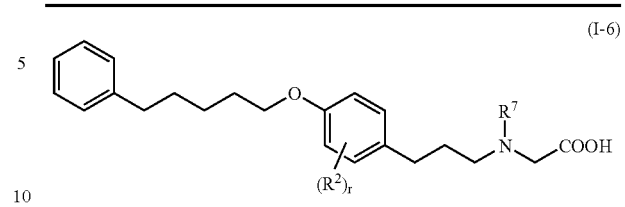
(I-6)

| No. | r | R² | R⁷ |
|---|---|---|---|
| 1 | 0 | — | H |
| 2 | 1 | 3'-OCH₃ | H |
| 3 | 1 | 2'-OCH₃ | H |
| 4 | 1 | 3'-CH₃ | H |
| 5 | 1 | 2'-CH₃ | H |
| 6 | 1 | 3'-Cl | H |
| 7 | 1 | 2'-Cl | H |
| 8 | 0 | — | CH₃ |
| 9 | 1 | 3'-OCH₃ | CH₃ |
| 10 | 1 | 2'-OCH₃ | CH₃ |
| 11 | 1 | 3'-CH₃ | CH₃ |
| 12 | 1 | 2'-CH₃ | CH₃ |
| 13 | 1 | 3'-Cl | CH₃ |
| 14 | 1 | 2'-Cl | CH₃ |

TABLE 7

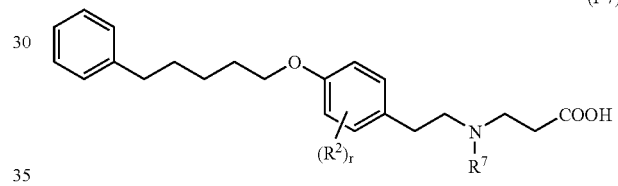
(I-7)

| No. | r | R² | R⁷ |
|---|---|---|---|
| 1 | 0 | — | H |
| 2 | 1 | 3'-OCH₃ | H |
| 3 | 1 | 2'-OCH₃ | H |
| 4 | 1 | 3'-CH₃ | H |
| 5 | 1 | 2'-CH₃ | H |
| 6 | 1 | 3'-Cl | H |
| 7 | 1 | 2'-Cl | H |
| 8 | 0 | — | CH₃ |
| 9 | 1 | 3'-OCH₃ | CH₃ |
| 10 | 1 | 2'-OCH₃ | CH₃ |
| 11 | 1 | 3'-CH₃ | CH₃ |
| 12 | 1 | 2'-CH₃ | CH₃ |
| 13 | 1 | 3'-Cl | CH₃ |
| 14 | 1 | 2'-Cl | CH₃ |

The Process for Preparation of the Compound of the Present Invention:

Among the compounds of the present invention of formula (I), the compounds where any $R^5$ in Q are not —NH₂, i.e., the compounds of formula (I-a)

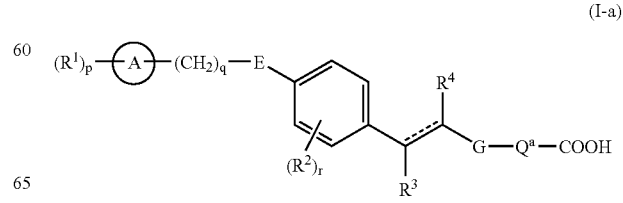
(I-a)

(wherein $Q^a$ has the same meaning as Q. With the proviso that, any $R^5$ in Q are not —$NH_2$. The other symbols have the same meanings as defined hereinbefore.)

may be prepared by the hydrolysis of the compounds of formula (IA-a)

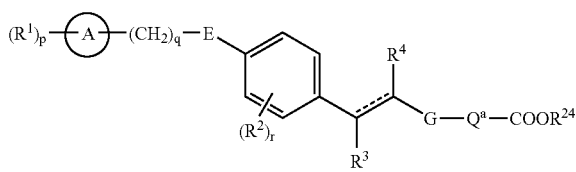

(IA-a)

(wherein all symbols have the same meanings as defined hereinbefore.).

The hydrolysis is well known. It is, for example, the hydrolysis in an alkaline condition or an acidic condition.

Concrete descriptions of these methods are as follows:

The hydrolysis in an alkaline condition may be carried out, for example, in an organic solvent (methanol, tetrahydrofuran or dioxane etc.) with hydroxide of alkaline metal (sodium hydroxide, potassium hydroxide or lithium hydroxide etc.), hydroxide of alkaline earth metal (barium hydroxide or calcium hydroxide etc.), carbonate (sodium carbonate or potassium carbonate etc.), or an aqueous solution thereof or a mixture thereof at 0–40° C.

The hydrolysis in an acidic condition may be carried out, for example, in an organic solvent (dichloromethane, chloroform, dioxane, ethyl acetate or anisole etc.), organic acid (acetic acid, trifluoroacetic acid or methanesulfonic acid etc.) or inorganic acid (hydrochloric acid or sulfuric acid etc.), or a mixture thereof (hydrogen bromide/acetic acid etc.) at 0–100° C.

Among the compounds of the present invention of formula (I), the compounds where at least one of $R^5$ in Q is —$NH_2$, i.e., the compounds of formula (I-b)

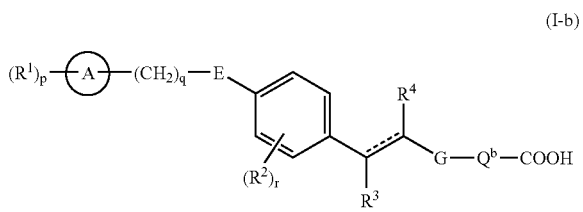

(I-b)

(wherein $Q^b$ has the same meaning as Q. With the proviso that, at least one of $R^5$ in Q is —$NH_2$. The other symbols have the same meanings as defined hereinbefore.) may be prepared by the reduction of the compounds where at least one of $R^5$ in Q is —$NO_2$ among the compounds prepared by the above method i.e., the compounds of formula (1-a-1)

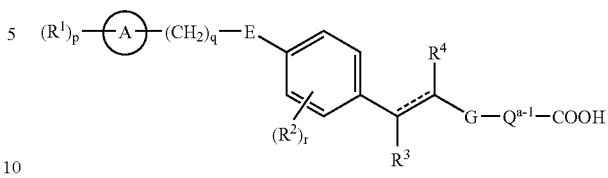

(I-a-1)

(wherein $Q^{a-1}$ has the same meaning as Q. With the proviso that, at least one of $R^5$ in Q is —$NO_2$. The other symbols have the same meanings as defined hereinbefore.).

The reduction of nitro group is well known. It is, for example, the reduction by hydrogenolysis or using organic metal.

The removal of a protecting group by hydrogenolysis may be carried out, for example, inert solvent [ether (tetrahydrofuran, dioxane, dimethoxyethane or diethylether etc.), alcohol (methanol or ethanol etc.), benzene (benzene or toluene etc.), ketone (acetone or methylethylketone etc.), nitrile (acetonitrile etc.), amide (dimethylformamide etc.), water, ethyl acetate, acetic acid or a mixture thereof etc.) in the presence of a hydrogenation catalyst (palladium on carbon, palladium black, palladium, palladium hydroxide, platinum oxide, nickel, Raney nickel, ruthenium chloride etc.) in the presence or absence of inorganic acid (hydrochloric acid, sulfuric acid, hypochlorous acid, boric acid, tetrafluoroboric acid etc.) or organic acid (acetic acid, p-toluenesulfonic acid, oxalic acid, trifluoroacetic acid, formic acid etc.), at atmospheric or positive pressure under an atmosphere of hydrogen or in the presence of ammonium formate at 0–200° C. When using an acid, its salt may be used at the same time.

The reduction using organic metal may be carried out, for example, in solvent which can be mixed in water (ethanol, methanol etc.) in the presence or absence of aqueous solution of hydrochloric acid, using organic metal (zinc, iron, tin, tinchloride, iron chloride etc.) at 50–150° C.

(A) The prodrugs represented by formula (IA) may be prepared by the following method.

Among the compounds of formula (IA), the compounds where any $R^5$ in Q are not —$NH_2$, i.e., the compounds of above formula (IA-a) may be prepared by the following method of (1)–(7).

(1) Among the Compounds of Formula (IA-a), the Compounds where G is —$CONR^7$—, i.e., the Compounds of Formula (IA-a-1)

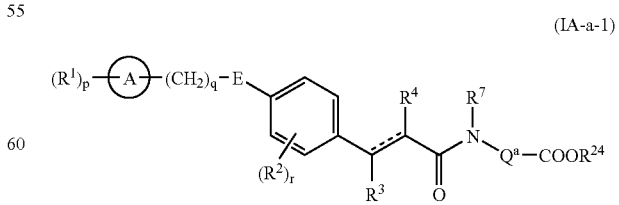

(IA-a-1)

(wherein all symbols have the same meanings as defined hereinbefore.) may be prepared by the following method of (a) or (b).

(1-a) The Compounds of Formula (IA-a-1) may be Prepared by the Amidation of the Compounds of Formula (II)

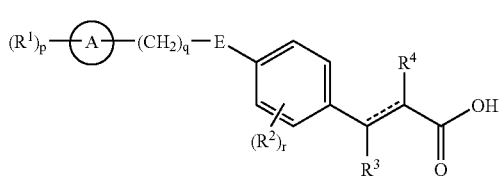
(II)

(wherein all symbols have the same meanings as defined hereinbefore.) with the compounds of formula (III)

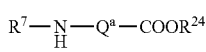
(III)

(wherein all symbols have the same meanings as defined hereinbefore.).

The method of amidation is known. It includes the method
(1) via an acyl halide,
(2) via a mixed acid anhydride,
(3) using a condensing agent.

These methods are explained as follows.

(1) The method via an acyl halide may be carried out, for example, by reacting carboxylic acid with an acyl halide (e.g. oxalyl chloride or thionyl chloride etc.) in an organic solvent (e.g. chloroform, methylene chloride, diethyl ether or tetrahydrofuran) or without a solvent at −20° C. to reflux temperature. And then the obtained acyl halide derivative may be reacted with amine in an inert organic solvent (e.g. chloroform, methylene chloride, diethyl ether or tetrahydrofuran) at 0–40° C. As an alternative, the obtained acyl halide derivative may be reacted in an organic solvent (dioxane, tetrahydrofuran) using an alkaline aqueous solution (e.g. sodium bicarbonate, sodium hydroxide) at 0-40° C.

(2) The method via a mixed acid anhydride may be carried out, for example, by reacting carboxylic acid with an acyl halide (e.g. pivaloyl chloride, tosyl chloride or mesyl chloride) or an acid derivative (ethyl chloroformate or isobutyl chloroformate) in an organic solvent (e.g. chloroform, methylene chloride, diethyl ether, tetrahydrofuran) or without a solvent, in the presence of tertiary amine (e.g. pyridine, triethylamine, dimethylaniline or dimethylaminopyridine) at 0–40° C. And then the obtained mixed acid anhydride derivative may be reacted with amine in an organic solvent (e.g. chloroform, methylene chloride, diethyl ether or tetrahydrofuran), at 0–40° C.

(3) The method using a condensing agent may be carried out, for example, by reacting carboxylic acid with amine in an organic solvent (e.g. chloroform, methylene chloride, dimethylformamide, diethyl ether or tetrahydrofuran) or without a solvent, in the presence or absence of tertiary amine (e.g. pyridine, triethylamine, dimethylaniline or dimethylaminopyridine), using a condensing agent (e.g. 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride), in the presence or absence of 1-hydroxybenzotiazole (HOBt), at 0–40° C.

The reaction described in (1), (2) and (3) may be carried out under an inert gas (e.g. argon, nitrogen) to avoid water in order to obtain a preferable result.

(1-b) Among the Compounds of Formula (IA-a-1), the Compounds where $R^7$ is not Hydrogen Atom, i.e., the Compounds of Formula (IA-a-1-1)

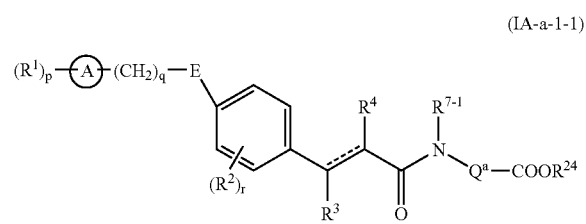
(IA-a-1-1)

(wherein $R^{7-1}$ has the same meaning as $R^7$. With the proviso that, $R^{7-1}$ is not hydrogen atom. The other symbols have the same meanings as defined hereinbefore.) may be prepared by reacting the compounds where $R^7$ is hydrogen atom among the compounds of formula (IA-a-1) prepared by the above method, i.e., the compounds of formula (IA-a-1-2)

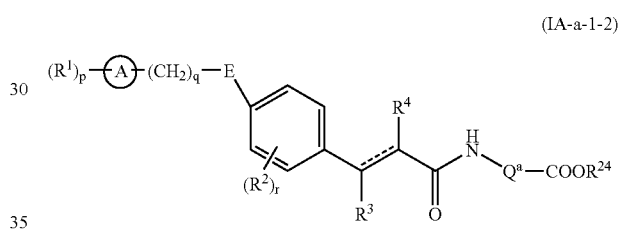
(IA-a-1-2)

(wherein all symbols have the same meanings as defined hereinbefore.) with the compounds of formula (IV)

$R^{7-1}$—X (IV)

(wherein X is halogen atom and the other symbols have the same meanings as defined hereinbefore.).

The reaction is well known, and for example, it may be carried out in an organic solvent (dimethylformamide, dimethylsulfoxide or tetrahydrofuran etc.), in the presence of alkali (sodium hydride, potassium hydride, potassium carbonate or sodium carbonate etc.) at 20–150° C.

(2) Among the Compounds of Formula (IA-a), the Compounds where G is —NR$^7$CO—, i.e., the Compounds of Formula (IA-a-2)

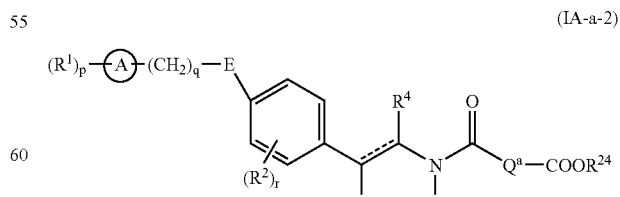
(IA-a-2)

(wherein all symbols have the same meanings as defined hereinbefore.) may be prepared by the following method of (c) or (d).

(2-c) The Compounds of Formula (IA-a-2) may be Prepared by the Amidation of the Compounds of Formula (V)

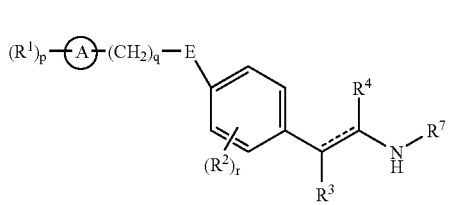

(wherein all symbols have the same meanings as defined hereinbefore.) with the compounds of formula (VI)

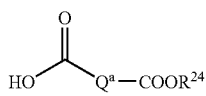

(wherein all symbols have the same meanings as defined hereinbefore.).

The amidation may be carried out by the above method.

(2-d) Among the Compounds of Formula (IA-a-2), the Compounds where $R^7$ is not Hydrogen Atom, i.e., the Compounds of Formula (IA-a-2-1)

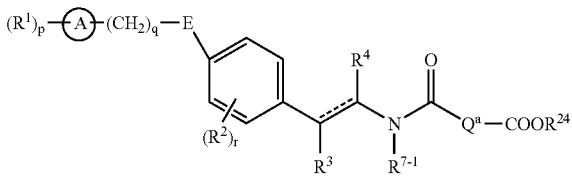

(wherein all symbols have the same meanings as defined hereinbefore.) may be prepared by reacting the compounds where $R^7$ is hydrogen atom among the compounds of formula (IA-a-2) prepared by the above method, i.e., the compounds of formula (IA-a-2-2)

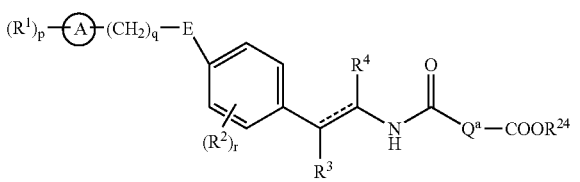

(wherein all symbols have the same meanings as defined hereinbefore.) with the compounds of formula (IV).

The reaction may be carried out by the above same method using the compounds of formula (IA-a-1-2) and formula (IV).

(3) Among the Compounds of Formula (IA-a), the Compounds where G is —CH$_2$NR$^7$—, i.e., the Compounds of Formula (IA-a-3)

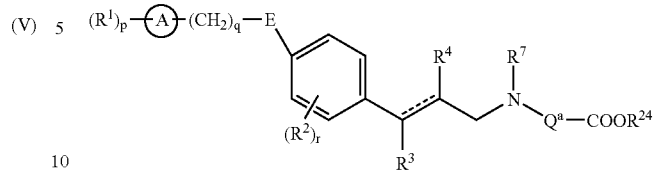

(wherein all symbols have the same meanings as defined hereinbefore.) may be prepared by the following method of (e), (f), (j) or (k).

(3-e) The Compounds of Formula (IA-a-3) may be Prepared by Reductive Amination of the Compounds of Formula (VII)

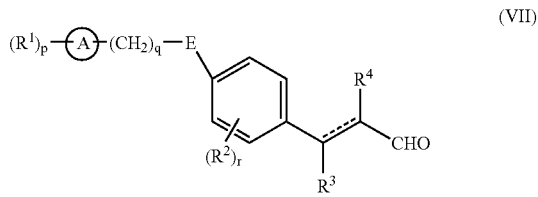

(wherein all symbols have the same meanings as defined hereinbefore.) with the compounds of formula (III).

The reductive amination is well known. For example, it may be carried out in an organic solvent (dichloroethane, dichloromethane, dimethylformamide or acetic acid, or mixture thereof etc.) in the presence of reducing agent (triethylamine or diisopropylethylamine etc.) with Lewis acid (titanium tetrachloride etc.), at 0–40° C., and subsequently by the addition of a reducing agent (sodium triacetoxyborohydride or sodium cyanoborohydride etc.) at 0–40° C.

(3-f) Among the Compounds of Formula (IA-a-3), the Compounds where $R^7$ is not Hydrogen Atom, i.e., the Compounds of Formula (IA-a-3-2)

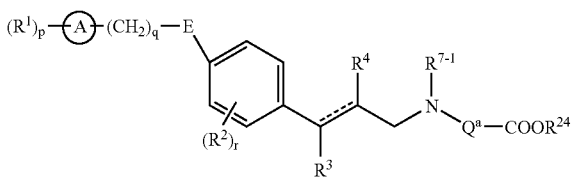

(wherein all symbols have the same meanings as defined hereinbefore.) may be prepared by reacting the compounds where $R^7$ is hydrogen atom prepared by the above method, i.e., the compounds of formula (IA-a-3-1)

(IA-a-3-1)

$(R^1)_p$—(A)—$(CH_2)_q$—E

[structure with $R^4$, $R^3$, $(R^2)_r$, N-H, $Q^a$—COOR$^{24}$]

(wherein all symbols have the same meanings as defined hereinbefore.) with the compounds of formula (IV).

The reaction may be carried out by the above same method using the compounds of formula (IA-a-1-2) and formula (IV).

(3-j) Among the Compounds of Formula (IA-a-3), the Compounds where $R^7$ is Hydrogen Atom and $Q^a$ is Methylene, i.e., the Compounds of Formula (IA-a-3—3)

(IA-a-3-3)

$(R^1)_p$—(A)—$(CH_2)_q$—E

[structure with $R^4$, $R^3$, $(R^2)_r$, N-H, COOR$^{24}$]

(wherein all symbols have the same meanings as defined hereinbefore.) may be prepared by the reaction of the compounds of formula (XIII)

(XIII)

$(R^1)_p$—(A)—$(CH_2)_q$—E

[structure with $R^4$, $R^3$, $(R^2)_r$, N-H, $R^{27}$]

(wherein $R^{27}$ is benzyloxycarbonyl or t-butoxycarbonyl and the other symbols have the same meanings as defined hereinbefore.) with the compounds of formula (XIV)

(XIV)

X—COOR$^{24}$ (wherein all symbols have the same meanings as defined hereinbefore.) and the removal of an amino-protecting group.

The reaction is well known. For example, it may be carried out in an inert organic solvent (tetrahydrofuran, dioxan, diethyleter, benzene, dimethoxyethane, hexane, cyclohexane, hexamethylphosphoric triamide or dimethylindazolidione, or mixture thereof etc.) in the presence or absence of alkali metal iodide (lithium iodide, sodium iodide or potassium iodide etc.) in the presence of a base (n-butyllithium, sec-butyllithium, t-butyllithium, phenyllithium, diisopropylaminolithium, potassium hydride, sodium hydride or lithium hexamethyldisiladide etc.), at −70 to 20° C.

If an amino-protecting group is benzyloxycarbonyl or t-butoxycarbonyl, the reduction may be carried out by the same method of the hydrolysis in an acidic condition or the hydrogenolysis described hereinbefore.

(3-k) Among the Compounds of Formula (IA-a-3), the Compounds where $R^7$ is Hydrogen Atom and $Q^a$ is Ethylene, i.e., the Compounds of Formula (IA-a-3-4)

(IA-a-3-4)

$(R^1)_p$—(A)—$(CH_2)_q$—E

[structure with $R^4$, $R^3$, $(R^2)_r$, N-H, COOR$^{24}$]

(wherein all symbols have the same meanings as defined hereinbefore.) may be prepared by the reaction of the compounds of formula (XV)

(XV)

$(R^1)_p$—(A)—$(CH_2)_q$—E

[structure with $R^4$, $R^3$, $(R^2)_r$, NH$_2$]

(wherein all symbols have the same meanings as defined hereinbefore.) with the compounds of formula (XVI)

(XVI)

[CH$_2$=CH]—COOR$^{24}$ (wherein all symbols have the same meanings as defined hereinbefore.).

The reaction is known and may be carried by reacting in organic solvent (methanol or ethanol etc.) at 0–20° C.

(4) Among the Compounds of Formula (IA-a), the Compounds where G is —NR$^7$CH$_2$—, i.e., the Compounds of Formula (IA-a-4)

(IA-a-4)

$(R^1)_p$—(A)—$(CH_2)_q$—E

[structure with $R^4$, $R^3$, $(R^2)_r$, N-$R^7$, $Q^a$—COOR$^{24}$]

(wherein all symbols have the same meanings as defined hereinbefore.) may be prepared by the following method of (g), (h), (m) or (n).

(4-g) The Compounds of Formula (IA-a-4) may be Prepared by Reductive Amination of the Compounds of Formula (VIII)

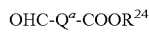   (VIII)

(wherein all symbols have the same meanings as defined hereinbefore.).

The reductive amination may be carried out by the above method.

(4-h) Among the Compounds of Formula (IA-a-4), the Compounds where $R^7$ is not Hydrogen Atom, i.e., the Compounds of Formula (IA-a-4-2)

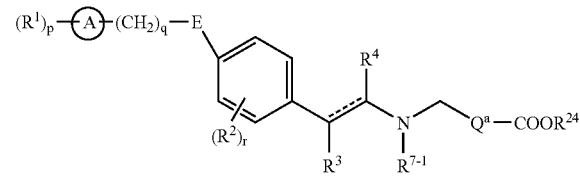
(IA-a-4-2)

(wherein all symbols have the same meanings as defined hereinbefore.) may be prepared by reacting the compounds where $R^7$ is hydrogen atom prepared by the above method, i.e., the compounds of formula (IA-a-4-1)

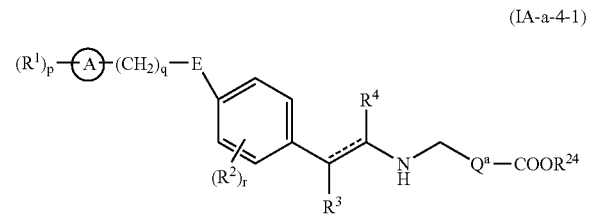
(IA-a-4-1)

(wherein all symbols have the same meanings as defined hereinbefore.) with the compounds of formula (IV).

The reaction may be carried out by the above same method using the compounds of formula (IA-a-1-2) and formula (IV).

(4-m) Among the Compounds of Formula (IA-a-4), the Compounds where $R^7$ is Hydrogen Atom and $Q^a$ is Methylene, i.e., the Compounds of Formula (IA-a-4-3)

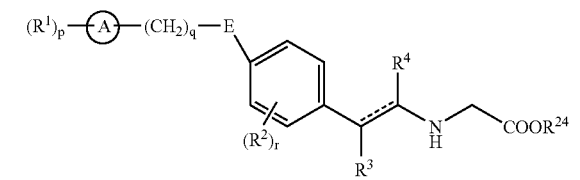
(IA-a-4-3)

(wherein all symbols have the same meanings as defined hereinbefore.) may be prepared by the reaction of the compounds of formula (V-1)

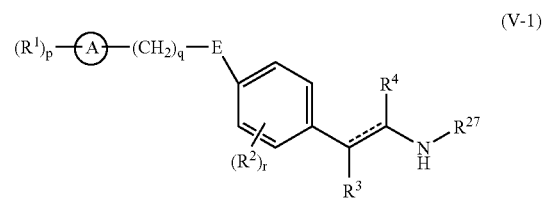
(V-1)

(wherein all symbols have the same meanings as defined hereinbefore.) with the compounds of formula (XIV) and the removal of an amino-protecting group.

The reaction may be carried out by the above method of the compounds of formula (XIII) and formula (XIV).

(4-n) Among the Compounds of Formula (IA-a4), the Compounds where $R^7$ is Hydrogen Atom and $Q^a$ is Ethylene, i.e., the Compounds of Formula (IA-a-4-4)

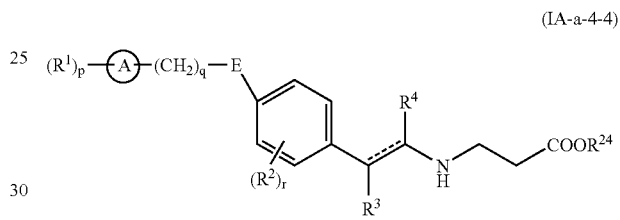
(IA-a-4-4)

(wherein all symbols have the same meanings as defined hereinbefore.) may be prepared by the reaction of the compounds of formula (V-2)

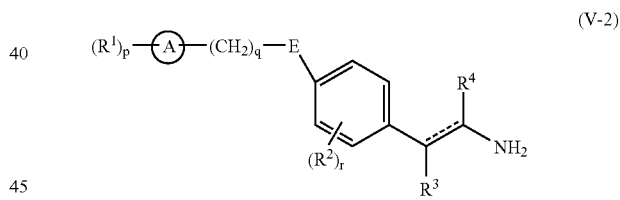
(V-2)

(wherein all symbols have the same meanings as defined hereinbefore.) with the compounds of formula (XV).

The reaction may be carried out by the above method of the compounds of formula (XV) and formula (XV).

(5) Among the Compounds of Formula (IA-a), the Compounds where G is —$NR^7SO_2$—, i.e., the Compounds of Formula (IA-a-5)

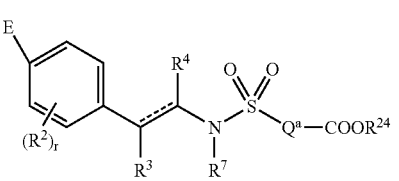
(IA-a-5)

(wherein all symbols have the same meanings as defined hereinbefore.) may be prepared by the sulfonamidation of the compounds of formula (V) with the compounds of formula (IX)

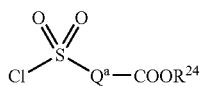 (IX)

(wherein all symbols have the same meanings as defined hereinbefore.).

The sulfonamidation is well known. For example, it may be carried out by reacting sulfonyl halide in presence of tertiary amine (isopropylethylamine, pyridine, triethylamine, dimethylaniline or dimethylaminopyridine etc.) in amine and an inert organic solvent (chloroform, dichoromethane, dichoroethane, diethyleter or tetrahydrofuran etc.) at 0–40° C.

(6) Among the Compounds of Formula (IA-a), the Compounds where G is —$SO_2NR^7$—, i.e., the Compounds of Formula (IA-a-6)

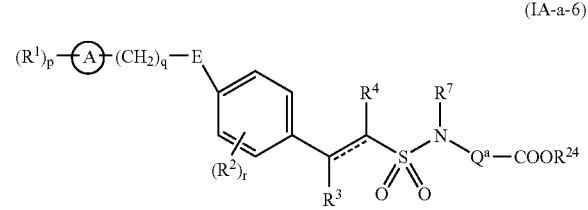 (IA-a-6)

(wherein all symbols have the same meanings as defined hereinbefore.) may be prepared by the sulfonamidation of the compounds of formula (X)

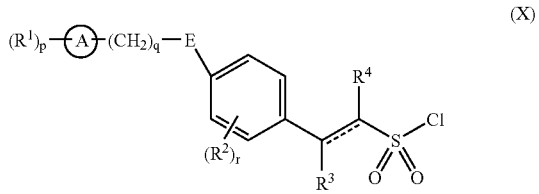 (X)

(wherein all symbols have the same meanings as defined hereinbefore.) with the compounds of formula (III).

The sulfonamidation may be carried out by the above method.

(7) Among the Compounds of Formula (IA-a), the Compounds where Q is

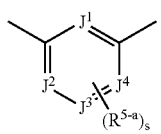

(wherein $R^{5-a}$ has the same meaning as $R^5$. With the proviso that, any $R^{5-a}$ are not —$NH_2$. The other symbols have the same meanings as defined hereinbefore.), $J^2$ is carbon atom substituted by $R^5$ and G is

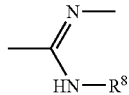

(wherein all symbols have the same meanings as defined hereinbefore.), and $R^5$ and $R^8$ taken together are single bond, i.e., the compounds of formula (IA-a-7)

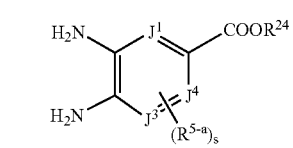 (IA-a-7)

(wherein all symbols have the same meanings as defined hereinbefore.) may be prepared by the amidation of the compounds of formula (II) with the compounds of formula (XI)

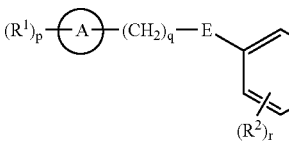 (XI)

(wherein all symbols have the same meanings as defined hereinbefore.) and the cyclization.

The amidation may be carried out by the above method.

The cyclization is well known. For example, it may be carried out by in an organic solvent (toluene or banzene etc.) in presence of catalyst (p-toluenesulfonic acid or pyridinium p-toluenesulfonic acid etc.) at 20–150° C.

Among the compounds of the present invention of formula (IA), the compounds where at least one of $R^5$ in $Q^a$ is —$NH_2$, i.e., the compounds of formula (IA-b)

(IA-b)

(wherein all symbols have the same meanings as defined hereinbefore.) may be prepared by the reduction of the compounds where at least one of $R^5$ in $Q^a$ is —$NO_2$ among the compounds of formula (I-a) prepared by the above method of (1)–(7) i.e., the compounds of formula (IAa-1)

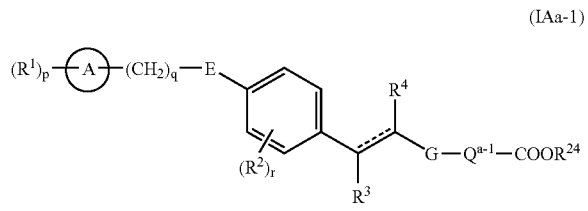

(IAa-1)

(wherein all symbols have the same meanings as defined hereinbefore.).

The reduction of nitro group may be carried out by the above method.

(B) The prodrugs of formula (IB) may be carried out by the following method.

Among the compounds of formula (IB), the compounds where any $R^5$ in $Q^a$ are not —$NH_2$, i.e., the compounds of formula (IB-a)

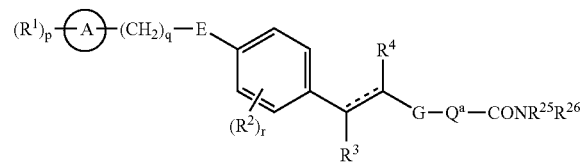

(IB-a)

(wherein all symbols have the same meanings as defined hereinbefore.) may be prepared using the compounds which contain carboxylic amide (—$CONR^{25}R^{26}$) instead of carboxylic acid ester (—$COOR^{24}$) by the same method of (1)–(7) described hereinbefore.

Among the compounds of the present invention of formula (IB), the compounds where at least one of $R^5$ in Q is —$NH_2$, i.e., the compounds of formula (IB-b)

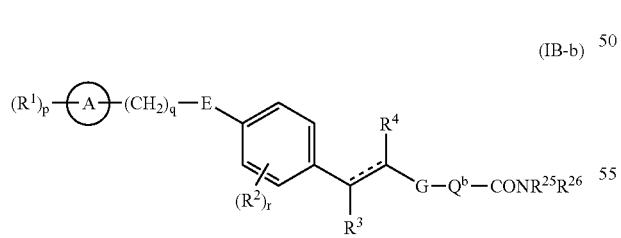

(IB-b)

(wherein all symbols have the same meanings as defined hereinbefore.) may be prepared by the reduction of the compounds where at least one of $R^5$ in Q is —$NO_2$ among the compounds of formula (IB-a) prepared by the above method, i.e., the compounds of formula (IB-a-1)

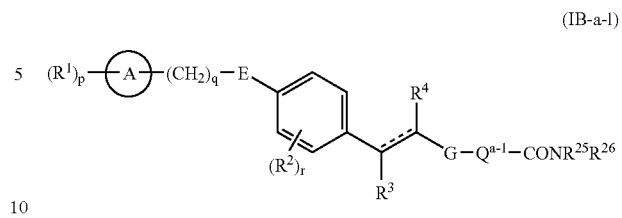

(IB-a-1)

(wherein all symbols have the same meanings as defined hereinbefore.).

The reduction of nitro group may be carried out by the above method.

The compounds of formula (IB) may be prepared by the amidation of the compounds of formula (I) with the compounds of formula (XII)

(XII)

(wherein all symbols have the same meanings as defined hereinbefore.).

The amidation may be carried out by the above method.

(C) The prodrugs of formula (IC) may be prepared by the reduction of the compounds of formula (IA).

The reduction of carboxylic acid ester to alcohol is well known. For example, it may be carried out in organic solvent (tetrahydrofuran, methanol or ethanol, or mixture thereof etc.) or aqueous solution thereof in presence of reducing agent (sodium borohydride, lithium borohydride or borane-dimethylsulfide complex etc.) at −20 to 60° C.

(D) The prodrugs of formula (ID) may be prepared by the following method.

Among the compounds of formula (ID), the compounds where any $R^5$ in Q are not —$NH_2$, i.e., the compounds of formula (ID-a)

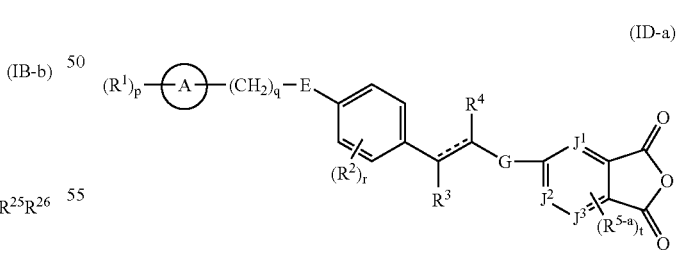

(ID-a)

(wherein all symbols have the same meanings as defined hereinbefore.) may be prepared using the compounds which contain acid anhydride (—COOCO—) instead of carboxylic acid ester (—$COOR^{24}$) by the same method of (1)-(7) described hereinbefore.

Among the compounds of the present invention of formula (ID), the compounds where at least one of $R^5$ in Q is —$NH_2$, i.e., the compounds of formula (ID-b)

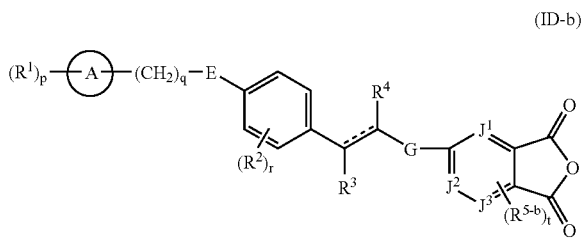

(ID-b)

(wherein $R^{5-b}$ has the same meaning as $R^5$. With the proviso that, at least one of $R^{5-b}$ is —$NH_2$. The other symbols have the same meanings as defined hereinbefore.) may be prepared by the reduction of the compounds where at least one of $R^5$ is —$NO_2$ among the compounds of formula (ID-a) prepared by the above method, i.e., the compounds of formula (ID-a-1)

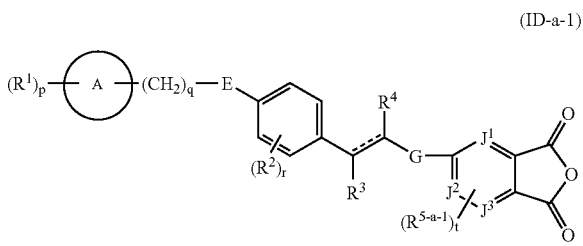

(ID-a-1)

(wherein $R^{5-a-1}$ has the same meaning as $R^5$. With the proviso that, at least one of $R^{5-a-1}$ is —$NO_2$. The other symbols have the same meanings as defined hereinbefore.).

The reduction of nitro group may be carried out by the above method.

The compound of formula (ID) may be prepared by the dehydration of the compound where Q is

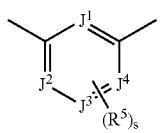

(wherein all symbols have the same meanings as defined hereinbefore.), $J^4$ is carbon atom and bonds COOH among the compounds of formula (I), i.e., the compounds of formula (1-D-1)

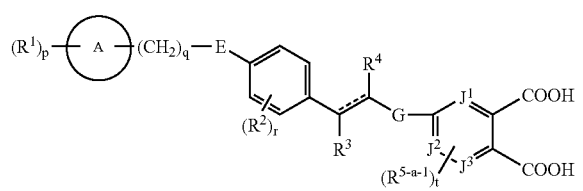

(I-D-1)

(wherein all symbols have the same meanings as defined hereinbefore.).

The dehydration is well known. For example, it may be carried out in organic solvent (toluene or benzene etc.) in presence or absence of dehydrating agent (phosphorus pentoxide, phosphorus oxychloride or acetic anhydride etc.) at 50–150° C.

The compounds represented by formula (II), (III), (IV), (V), (V-1), (V-2), (VI), (VII), (VIII), (IX), (X), (XI), (XII), (XIII), (XIV), (XV) and (XVI) which are used as the starting materials may be prepared by known methods or put on sale. For example, the materials may be prepared by the methods described on the specification.

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

INDUSTRIAL APPLICABILITY

The compound of the present invention has an agonistic action for EDG-1. The agonistic action was confirmed by, for example, screening described hereinafter in laboratory.

(1) Assessment of an Agonistic Action by Monitoring the Intracellular Calcium Ion The assessment of an agonistic action for the receptor was carried out using the human EDG-1 gene over expression cells (Chinese Hamster Ovary, CHO). EDG-1 expression cells were cultured with Ham's F12 (GIBCO BRL, No. 11765-047) medium containing 10% FBS, Penicillin/Streptomycin and Blasticidin (5 μg/mL). First, in order to load Fura2-AM (Dojindo, No. 348-05831) in the cells, the cells were incubated by 5 μM Fura2-AM solution (Ham's F12 medium containing 10% FBS, 20 mM HEPES pH7.4, 2.5 mM Probenecid (Sigma, catalog No.P-8761)) at 37° C. for 60 min. Next, the cells were washed once by Hanks solution containing 20 mM HEPES pH7.4, 2.5 mM Probenecid and soaked in the Hanks solution until assay.

The plate was set on the fluorescence drug screening system (Hamamatsu photonics FDSS-2000). After measurement of the background signal for 30 minutes, the solution of the assay compound was added. The test compounds were added at the final concentration range of between 0.1 nM and 10 μM as the final dimethyl sulfoxide (DMSO) concentration made to 1/1000 of the original solution. Fura2-$Ca^{2+}$ fluorescence excited at 340 nm and 380 nm was measured every 3 seconds at emission wavelength 500 nm. Intracellular $Ca^{2+}$ concentration was assessed with fluorescent ratio of excitation wavelength 340 nm and 380 nm. Agonistic activity was calculated as below, that is, the control value (A) was obtained by measuring the response of 100 nM S1P (BIOMOL:M9076) after adding DMSO to the well for the test compounds, and (A) was compared with the value (B) which is the difference of fluorescent ratio obtained by measuring response between the pre and post of test compounds added. Rate of intracellular $Ca^{2+}$ increase (%) was calculated as following equation.

rate of increase (%)=$(B/A) \times 100$

Moreover, rate of increase was calculated at each concentration and $EC_{50}$ (Concentration of Half—100 nM S1P $Ca^{2+}$ release) of each compound was calculated setting the maximal concentration of the compound giving the response corresponding to that of S1P at the concentration of 100 nM. The result shows in table 8.

TABLE 8

| Compound No. | EC$_{50}$(nM) |
|---|---|
| Example 2(1) | 9.0 |
| Example 2(3) | 1.4 |
| Example 9(6) | 7.3 |
| Example 16 | 8.3 |
| Example 16(3) | 4.5 |
| Example 19 | 1.5 |
| Example 28 | 25 |
| Example 32 | 30 |

According to above result, it was confirmed that the compound of the present invention has an agonistic action for EDG-1.

Toxicity:

The compound of the present invention has low toxicity so that use of it as a pharmaceutical can be considered as safe enough.

INDUSTRIAL APPLICABILITY

Application to Pharmaceuticals:

Because of having an EDG-1 agonism, the compounds represented by formula (I), the prodrugs thereof or the non-toxic salts thereof are useful in preventing and/or treating peripheral arterial disease such as arteriosclerosis obliterans, thromboangiitis obliterans, Buerger's disease or diabetic neuropathy, sepsis, angiitis, nephritis, pneumonia, stroke, myocardial infarction, edematous state, atherosclerosis, varicosity such as hemorrhoid, anal fissure or fistula ani, dissecting aneurysm of the aorta, angina, DIC, pleuritis, congestive heart failure, multiple organ failure, bedsore, burn, chronic ulcerative colitis, Crohn's disease, heart transplantation, renal transplantation, dermal graft, liver transplantation, osteoporosis, pulmonary fibrosis, interstitial pneumonia, chronic hepatitis, liver cirrhosis, chronic renal failure, or glomerular sclerosis for mammal, especially human.

The compounds of the present invention represented by formula (I) may be administered in combination with other drugs for the purpose of 1) complement and/or enhancement of preventing and/or treating effect, 2) improvement of dynamics and absorption of the compound, and lowering of dose, and/or 3) alleviation of side effect of the compound.

The compounds of the present invention represented by formula (I) may be administered in combination with other drugs as a composition in one drug product comprising these components, or may be administered separately. When they are administered independently, they may be administered simultaneously or with time lag. Administering with time lag includes the method of administering the compounds of the present invention represented by formula (I) before other drugs and vice versa; they may be administered in the same route or not.

The above combination takes effects on whichever disease treating and/or preventing effect of the compounds of the present invention represented by formula (I) is complemented and/or enhanced.

As other methods to complement and/or to enhance the preventing and/or treating effect for disease which is susceptible to treatment by EDG-1 agonist such as arteriosclerosis obliterans, thromboangiitis obliterans, Buerger's disease, diabetic neuropathy, congestive heart failure, multiple organ failure, bedsore, burn or chronic ulcerative colitis etc., gene therapy inducing vascularization, cell therapy or drug therapy etc. are given. EDG-1 agonist may be used with these methods. For example, the method that gene such as VEGF or HGF etc. is supplemented via an intramuscular injection is effective and EDG-1 agonist may be used with this method. Cell therapy is the method that vascular endothelial precursor cell is given. For example, the method that bone marrow mononuclear cell (stem cell fraction), which is isolated from self-bone marrow and concentrated, is supplemented via an intramuscular injection is effective and EDG-1 agonist may be used with this method, too. Moreover, in drug therapy, the other drugs which have vascularization action are used and EDG-1 agonist has an effect by combination with following drugs. For example, as protein therapeutic product, VEGF, HGF, FGF, HIF-α or PDGF etc. are given. As low molecular weight therapeutic product, alprostadil, alcloxa, tretinoin tocoferil or MCI-154 etc. are give.

When the compounds of the present invention represented by formula (I), the non-toxic salts thereof or the hydrates thereof are used for the above-described purpose, it is usually administered systemically or topically via an oral or parenteral route.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention represented by formula (I) may be administered in the composition of, for example, solid compositions, liquid compositions or other compositions each for oral administration, or injections, liniments or suppositories, each for parenteral administration.

Solid compositions for oral administration include compressed tablets, pills, capsules, powders, and granules.

Capsules include hard capsules and soft capsules.

In such solid compositions, one or more of the active substance(s) may be admixed with at least one inert diluent such as lactose, mannitol, glucose, hydroxypropyl cellulose, microcrystalline cellulose, starch, polyvinylpyrrolidone or magnesium aluminometasilicate. The compositions may comprise, in accordance with the conventional process, additives other than the inert diluent, for example, lubricants such as magnesium stearate, disintegrants such as cellulose calcium glycolate, stabilizer such as lactose, and solubilizing agent such as glutamic acid or aspartic acid. Tablets or pills may be coated with a film of a gastric soluble or enteric substance such as sucrose, gelatin, hydroxypropyl cellulose or hydroxypropyl methylcellulose phthalate, or with two or more layers, if necessary. Furthermore, capsules made of a substance which can be absorbed in the body, for example, gelatin, are included.

Liquid compositions for oral administration include pharmaceutically acceptable emulsions, solutions, syrups and elixirs. Such liquid compositions comprise one or more of the active substance(s) and an ordinarily employed inert diluent(s) (for example, purified water or ethanol) dissolving the substance(s) therein. The compositions may comprise, in addition to the inert diluent, an adjuvant such as humectants or suspending agents, sweetening agents, flavoring agents, aromatic agents and antiseptics.

The other compositions for oral administration include sprays which comprise one or more active substance(s) and are formulated in a manner known per se in the art. The compositions may comprise, in addition to an inert diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

In the present invention, injections for parenteral administration include sterile aqueous and/or non-aqueous solutions, suspensions and emulsions. The aqueous solutions or suspensions include, for example, distilled water for injection and saline. The non-aqueous solutions or suspensions include propylene glycol, polyethylene glycol, vegetable oils such as olive oil, alcohol such as ethanol and Polysorbate 80 (trade mark). Furthermore, sterile aqueous and non-aqueous solutions, suspensions, and emulsions may be used in combination. Such compositions may additionally comprise adjuvants such as antisaptic, humectant, emulsfier, dispersant, stabilizer (such as lactose) and solubilizing agent (such as glutamic acid and aspartic acid). They are sterilized by filtration through a bacteria retaining filter, the addition of a sterilizer, or irradiation. Also, a sterile solid composition is prepared and then, for example, a freeze-dried product may be dissolved in sterilized or sterile distilled water for injection or another sterile solvent before use.

The other compositions for parenteral administration include liquids for external use, ointments, endermic liniments, suppositories for intrarectal administration and pessaries for vaginal administration which comprise one or more of the active substance(s) and may be prepared by methods known per se.

BEST MODE FOR CARRYING OUT THE INVENTION

The following Reference Examples and Examples are intended to illustrate the present invention, but do not limit them.

In chromatographic separations and TLC, the solvents in parenthesis show the eluting and developing solvents and the ratios of the solvents used are by volume. The solvents in parenthesis in NMR show the solvents used for measurement.

REFERENCE EXAMPLE 1 methyl 3-[4-(5-phenylpentyloxy)phenyl]propanoate

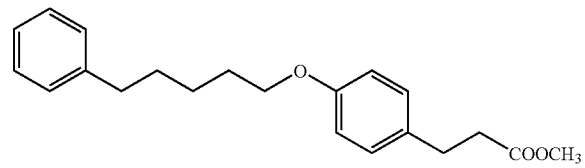

To a mixture of 5-phenylpentanol (3.7 mL), methyl 3-(4-hydroxyphenyl)propanoate (3.6 g), triphenylphosphine (5.77 g) and dichloromethane (200 mL) was added 1,1'-(azodicarbonyl)dipiperidine (5.55 g). The reaction mixture was stirred at room temperature for 4 days. Diethyl ether was added to the reaction mixture, which was filtered and the filtrate was concentrated. Hexane-diethyl ether (1:1) (200 mL) was added to the residue, which was filtered and the filtrate was concentrated. The obtained residue was purified by column chromatography on silica gel (hexane: ethyl acetate=9:1→4:1) to give the title compound (6.16 g) having the following physical data.

TLC: Rf 0.46 (hexane:ethyl acetate=9:1); NMR (CDCl$_3$): δ 7.32–7.06 (m, 7H), 6.84–6.77 (m, 2H), 3.92 (t, J=6.6 Hz, 2H), 3.66 (s, 3H), 2.89 (t, J=7.6 Hz, 2H), 2.68–2.55 (m, 4H), 1.87–1.41 (m, 6H).

REFERENCE EXAMPLE 2

3-[4-(5-phenylpentyloxy)phenyl]propanoic acid

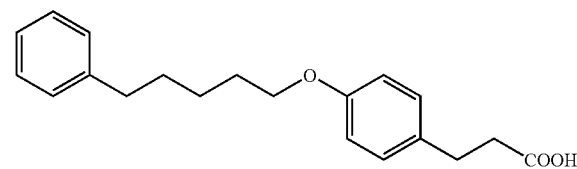

To a solution of the compound prepared in Reference Example 1 (12 g) in methanol (60 mL) and tetrahydrofuran (80 mL) was added 2N aqueous sodium hydroxide solution (40 mL). The reaction mixture was refluxed for 4 hours. On ice bath, 1N hydrochloric acid was added to the reaction mixture, which was extracted with ethyl acetate. The extract was dried over anhydrous magnesium sulfate and concentrated to give the title compound (11.32 g) having the following physical data.

TLC: Rf 0.40 (chloroform:methanol=9:1); NMR (CDCl$_3$): δ 7.31–7.09 (m, 7H), 6.85–6.78 (m, 2H), 3.92 (t, J=6.6 Hz, 2H), 2.90 (t, J=7.6 Hz, 2H), 2.64 (t, J=7.6 Hz, 4H), 1.87–1.42 (m, 6H).

REFERENCE EXAMPLE 3

3-[4-(5-phenylpentyloxy)phenyl]propanoyl chloride

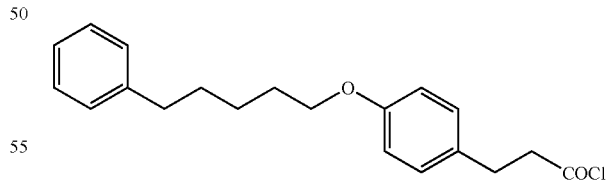

To a solution of the compound prepared in Reference Example 2 (151 mg) in dichloromethane (1 mL) was poured a drop of dimethylformamide. Further, to the mixture was added oxalyl chloride (0.13 mL) on ice bath. The reaction mixture was stirred at room temperature for 1 hour. The reaction mixture was concentrated to give the title compound (167 mg).

EXAMPLE 1 methyl 2-methoxy-5-[3-(4-(5-phenylpentyloxy)phenyl)propanoylamino]benzoate

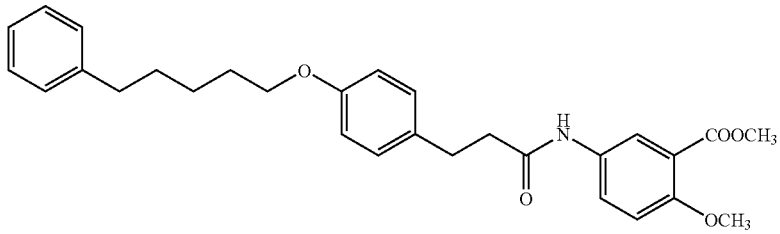

To a solution of methyl 2-methoxy-5-aminobenzoate (89 mg) in dichloromethane (1 mL) was added triethylamine (0.1 mL) and a solution of the compound prepared in Reference Example 3 in dichloromethane (1 mL) sequentially. The reaction mixture was stirred at room temperature for 4 hours. 1N hydroxychloric acid was added to the reaction mixture, which was extracted with ethyl acetate. The extract was washed with saturated aqueous solution of sodium hydrogen carbonate and brine, dried over anhydrous magnesium sulfate and concentrated. The obtained residue was purified by column chromatography on silica gel (chloroform:methanol=50:1) to give the title compound (197 mg) having the following physical data.

TLC: Rf 0.48 (hexane:ethyl acetate=1:1); NMR (CDCl$_3$): δ 7.73–7.67 (m, 2H), 7.31–7.11 (m, 7H), 6.99–6.80 (m, 4H), 3.95–3.87 (m, 8H), 2.98 (t, J=7.5 Hz, 2H), 2.68–2.56 (m, 4H), 1.87–1.45 (m, 6H).

EXAMPLE 1(1)-1(5)

By the same procedure as described in Example 1 using the corresponding amine derivatives respectively instead of methyl 2-methoxy-5-aminobenzoate, the following compounds of the present invention were obtained.

EXAMPLE 1(1)

methyl 2-chloro-5-[3-(4-(5-phenylpentyloxy)phenyl)propanoylamino]benzoate

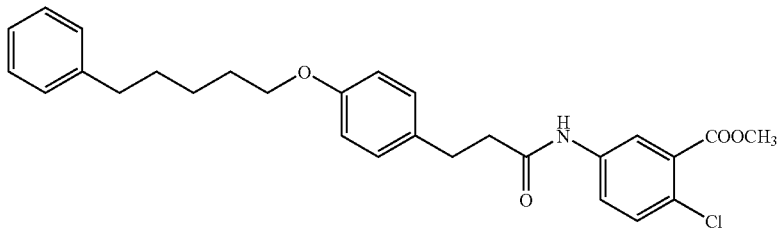

TLC: Rf 0.52 (hexane:ethyl acetate=2:1); NMR (DMSO-d$_6$): δ 10.20 (s, 1H), 8.12 (d, J=2.7 Hz, 1H), 7.73 (dd, J=2.7, 8.7 Hz, 1H), 7.48 (d, J=8.7 HZ, 1H), 7.30–7.15 (m, 5H), 7.12 (d, J=8.4 Hz, 2H), 6.81 (d, J=8.4 Hz, 2H), 3.90 (t, J=6.6 Hz, 2H), 3.86 (s, 3H), 2.84 (t, J=7.5 Hz, 2H), 2.59 (t, J=7.5 Hz, 4H), 1.80–1.55 (m, 4H), 1.50–1.40 (m, 2H).

EXAMPLE 1(2)
methyl 2-bromo-5-[3-(4-(5-phenylpentyloxy)phenyl)propanoylamino]benzoate
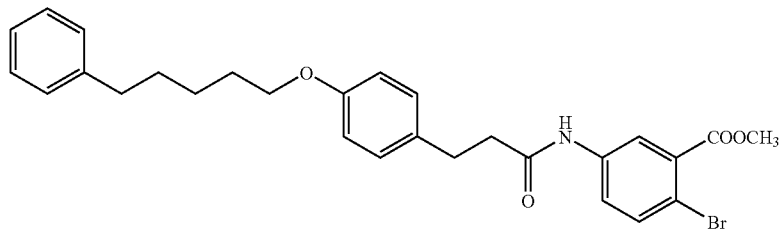
TLC: Rf 0.59 (hexane:ethyl acetate=2:1); NMR (CDCl$_3$):
δ 7.84 (d, J=2.2 Hz, 1H), 7.56 (d, J=8.4 Hz, 1H), 7.50 (dd, J=8.4, 2.2 Hz, 1H), 7.32–7.10 (m, 8H), 6.85–6.78 (m, 2H), 3.92 (t, J=6.6 Hz, 2H), 3.91 (s, 3H), 2.98 (t, J=7.2 Hz, 2H), 2.68–2.58 (m, 4H), 1.87–1.41 (m, 6H).
EXAMPLE 1(3)
methyl 2-methoxycarbonyl-5-[3-(4-(5-phenylpentyloxy)phenyl)propanoylamino]benzoate
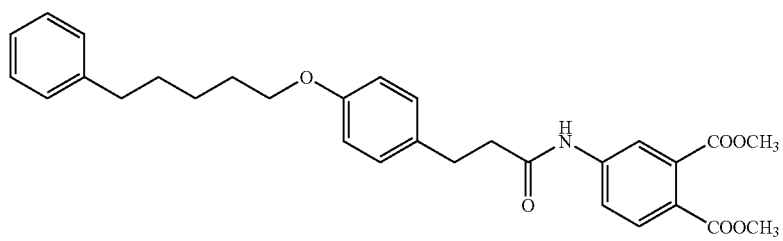
TLC: Rf 0.24 (hexane:ethyl acetate=2:1); NMR (CDCl$_3$):
δ 7.77–7.64 (m, 3H), 7.52 (s, 1H), 7.32–7.08 (m, 7H), 6.84–6.77 (m, 2H), 3.94–3.86 (m, 8H), 2.97 (t, J=7.2 Hz, 2H), 2.63 (t, J=7.2 Hz, 4H), 1.87–1.41 (m, 6H).

EXAMPLE 1(4)

methyl 3-methoxycarbonyl-5-[3-(4-(5-phenylpentyloxy)phenyl)propanoylamino]benzoate

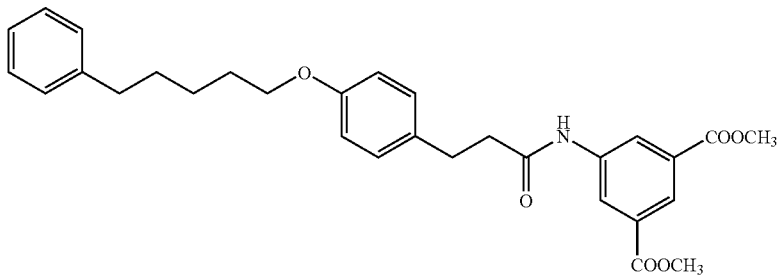

TLC: Rf 0.43 (hexane:ethyl acetate=2:1); NMR (CDCl$_3$): δ 8.40 (t, J=1.5 Hz, 1H), 8.31 (d, J=1.5 Hz, 1H), 7.36 (s, 1H), 7.31–7.25 (m, 2H), 7.20–7.11 (m, 5H), 6.84–6.79 (m, 2H), 3.94–3.90 (m, 8H), 3.00 (t, J=7.5 Hz, 2H), 2.69–2.61 (m, 4H), 1.85–1.66 (m, 4H), 1.55–1.44 (m, 2H).

EXAMPLE 1(5)

methyl 2-methylthio-5-[3-(4-(5-phenylpentyloxy)phenyl)propanoylamino]benzoate

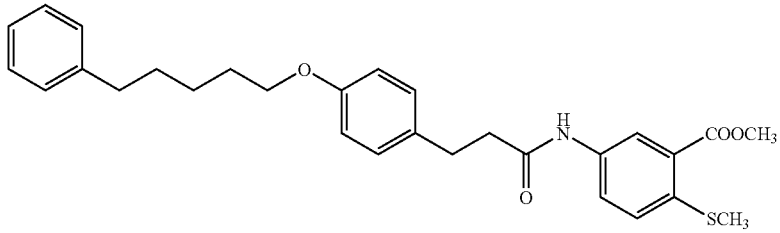

TLC: Rf 0.38 (hexane:ethyl acetate=2:1); NMR (CDCl$_3$): δ 7.95 (d, J=2.4 Hz, 1H), 7.70 (dd, J=2.4, 8.7 Hz, 1H), 7.30–7.10 (m, 9H), 6.82 (d, J=8.4 Hz, 2H), 3.92 (t, J=6.6 Hz, 2H), 3.89 (s, 3H), 2.99 (t, J=7.5 Hz, 2H), 2.66–2.59 (m, 4H), 2.44 (s, 3H), 1.85–1.60 (m, 4H), 1.60–1.40 (m, 2H).

EXAMPLE 2

2-methoxy-5-[3-(4-(5-phenylpentyloxy)phenyl)propanoylamino]benzoic acid

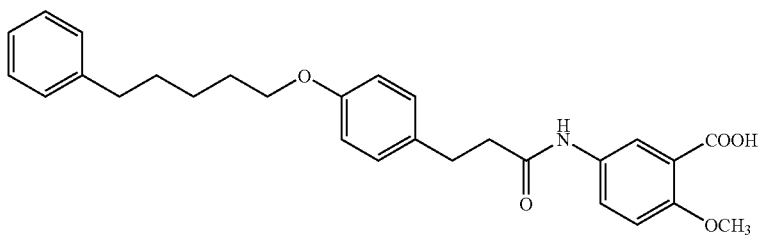

To a solution of the compound prepared in Example 1 (190 mg) in methanol (1 mL) and tetrahydrofuran (1.5 mL) was added 2N aqueous sodium hydroxide solution (0.5 mL). The reaction mixture was stirred at room temperature for 4 hours. To the reaction mixture was added 1N hydrochloric acid. The precipitate was filtered, washed with water and dried to give the compound of the present invention (173 mg) having the following physical data.

TLC: Rf 0.37 (chloroform:methanol=9:1); NMR (DMSO-d$_6$): δ 12.75–12.40 (br, 1H), 9.84 (s, 1H), 7.86 (d, J=2.6 Hz, 1H), 7.66 (dd, J=9.0, 2.6 Hz, 1H), 7.28–7.01 (m, 8H), 6.79 (d, J=8.6 Hz, 2H), 3.88 (t, J=6.4 Hz, 2H), 3.75 (s, 3H), 2.81 (t, J=7.4 Hz, 2H), 2.56 (t, J=7.6 Hz, 4H), 1.76–1.31 (m, 6H).

EXAMPLE 2(1)–2(5)

By the same procedure as described in Example 2 using the compounds prepared in Example 1(1)–1(5) respectively instead of the compound prepared in Example 1, the following compounds of the present invention were obtained.

EXAMPLE 2(1)

2-chloro-5-[3-(4-(5-phenylpentyloxy)phenyl)propanoylamino]benzoic acid

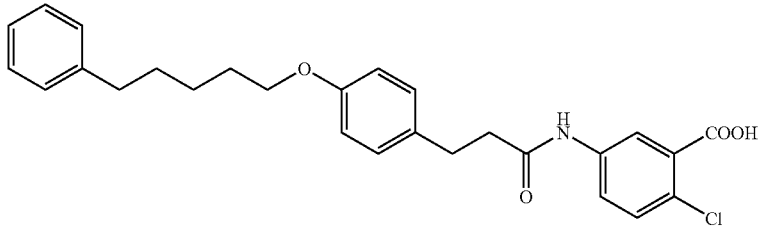

TLC: Rf 0.36 (chloroform:methanol=9:1); NMR (DMSO-$d_6$): δ 13.35 (s, 1H), 10.15 (s, 1H), 8.07 (d, J=2.7 Hz, 1H), 7.71 (dd, J=2.7, 8.7 Hz, 1H), 7.44 (d, J=8.7 Hz, 1H), 7.30–7.15 (m, 5H), 7.13 (d, J=8.4 Hz, 2H), 6.80 (d, J=8.4 Hz, 2H), 3.90 (t, J=6.6 Hz, 2H), 2.84 (t, J=7.5 Hz, 2H), 2.59 (t, J=7.5 Hz, 4H), 1.80–1.55 (m, 4H), 1.50–1.35 (m, 2H).

EXAMPLE 2(2)

2-bromo-5-[3-(4-(5-phenylpentyloxy)phenyl)prpanolylamino]benzoic acid

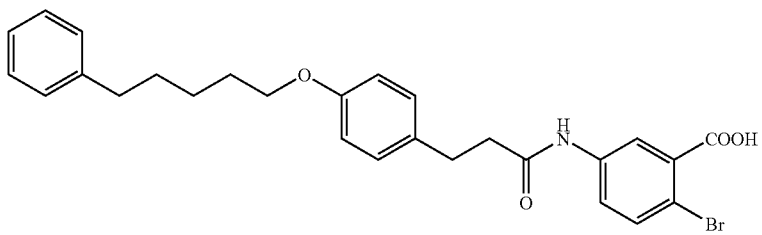

TLC: Rf 0.41 (chloroform:methanol:acetic acid=90:10:1); NMR (DMSO-$d_6$): δ 10.13 (s, 1H), 8.02 (d, J=1.5 Hz, 1H), 7.63–7.57 (m, 2H), 7.27–7.09 (m, 7H), 6.79 (d, J=8.4 Hz, 2H), 3.87 (t, J=6.6 Hz, 2H), 2.81 (t, J=7.5 Hz, 2H), 2.56 (t, J=7.5 Hz, 4H), 1.74–1.54 (m, 4H), 1.44–1.34 (m, 2H).

EXAMPLE 2(3)

2-carboxy-5-[3-(4-(5-phenylpentyloxy)phenyl)propanoylamino]benzoic acid

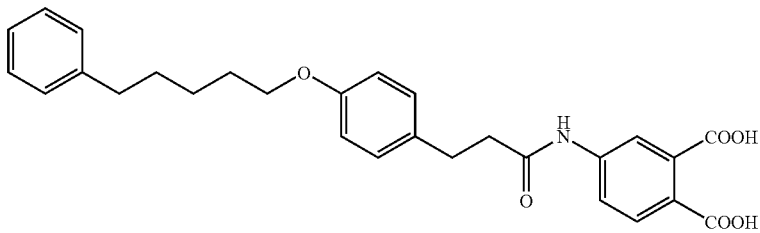

TLC: Rf 0.32 (chloroform:methanol:acetic acid=9:1:1); NMR (DMSO-$d_6$): δ 10.23 (s, 1H), 7.83 (s, 1H), 7.72–7.65 (m, 2H), 7.27–7.07 (m, 7H), 6.79 (d, J=8.4 Hz, 2H), 3.88 (t, J=6.6 Hz, 2H), 2.82 (t, J=7.5 Hz, 2H), 2.62–2.54 (m, 4H), 1.73–1.54 (m, 4H), 1.44–1.34 (m, 2H).

EXAMPLE 2(4)

3-carboxy-5-[3-(4-(5-phenylpentyloxy)phenyl)propanoylamino]benzoic acid

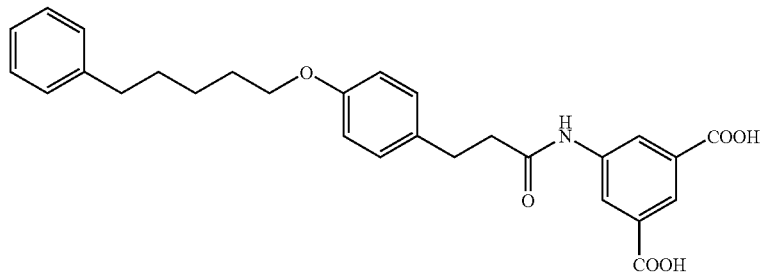

TLC: Rf 0.28 (chloroform:methanol:acetic acid=90:10:1); NMR (DMSO-$d_6$): δ 10.24 (s, 1H), 8.40 (d, J=1.5 Hz, 2H), 8.12 (t, J=1.5 Hz, 1H), 7.27–7.11 (m, 7H), 6.82–6.77 (m, 2H), 3.87 (t, J=6.6 Hz, 2H), 2.83 (t, J=7.5 Hz, 2H), 2.62–2.53 (m, 4H), 1.73–1.54 (m, 4H), 1.43–1.33 (m, 2H).

EXAMPLE 2(5)

2-methylthio-5-[3-(4-(5-phenylpentyloxy)phenyl)propanoylamino]benzoic acid

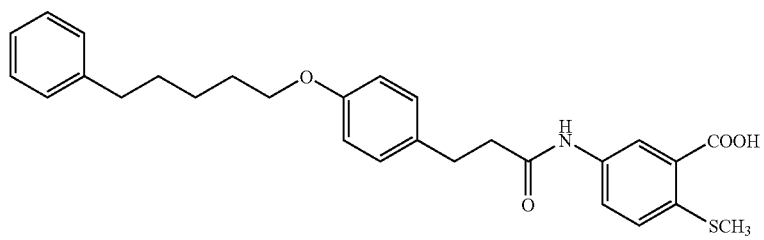

TLC: Rf 0.42 (chloroform:methanol=9:1); NMR (DMSO-$d_6$): δ 13.00 (s, 1H), 9.99 (s, 1H), 8.17 (d, J=2.4 Hz, 1H), 7.77 (dd, J=2.4, 8.4 Hz, 1H), 7.27 (d, J=8.4 Hz, 1H), 7.30–7.15 (m, 5H), 7.12 (d, J=8.7 Hz, 2H), 6.81 (d, J=8.7 Hz, 2H), 3.90 (t, J=6.6 Hz, 2H), 2.83 (t, J=7.5 Hz, 2H), 2.60–2.40 (m, 4H), 2.37 (s, 3H), 1.80–1.60 (m, 4H), 1.50–1.40 (m, 2H).

EXAMPLE 3

3-[3-(4-(5-phenylpentyloxy)phenyl)propanoylamino]benzoic acid

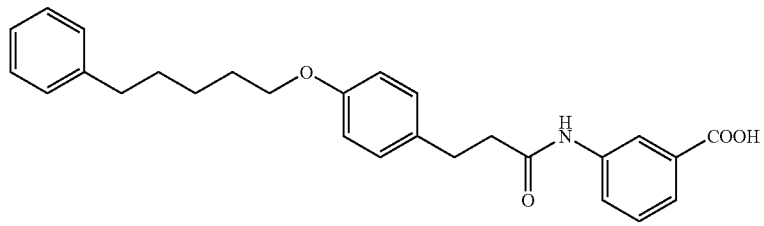

By the same procedure as described in Example 1→Example 2 using methyl 3-aminobenzoate instead of methyl 2-methoxy-5-aminobenzoate, the following compound of the present invention having the following physical data were obtained.

TLC: Rf 0.38 (chloroform:methanol=9:1); NMR (DMSO-$d_6$): δ 13.04–12.80 (br, 1H), 10.05 (s, 1H), 8.19 (s, 1H), 7.79 (d, J=7.8 Hz, 1H), 7.58 (d, J=7.8 Hz, 1H), 7.38 (t, J=7.8 Hz, 1H), 7.28–7.10 (m, 7H), 6.79 (d, J=8.4 Hz, 2H), 3.88 (t, J=6.6 Hz, 2H), 2.82 (t, J=7.6 Hz, 2H), 2.56 (t, J=7.6 Hz, 4H), 1.76–1.30 (m, 6H).

EXAMPLES 3(1)–3(6)

By the same procedure as described in Example 3 using the corresponding amine derivatives respectively instead of methyl 3-aminobenzoate, the following compounds of the present invention were obtained.

EXAMPLE 3(1)

3-[N-(pyridin-2-yl)methyl-3-(4-(5-phenylpentyloxy)phenyl)propanoylamino]benzoic acid hydrochloride

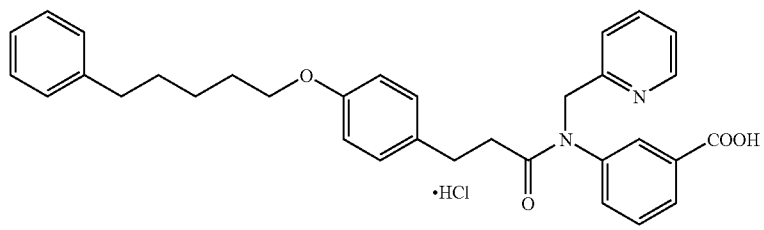

TLC: Rf 0.52 (chloroform:methanol:acetic acid=90:10:1); NMR (DMSO-$d_6$): δ 8.66 (d, J=5.2 Hz, 1H), 8.26–8.12 (br, 1H), 7.88–7.82 (m, 2H), 7.68–7.45 (m, 4H), 7.28–7.09 (m, 5H), 6.93 (d, J=8.8 Hz, 2H), 6.73 (d, J=8.8 Hz, 2H), 5.10 (s, 2H), 3.86 (t, J=6.4 Hz, 2H), 2.78–2.67 (m, 2H), 2.56 (t, J=7.6 Hz, 2H), 2.43–2.26 (br, 2H), 1.75–1.30 (m, 6H).

EXAMPLE 3(2)
3-chloro-5-[3-(4-(5-phenylpentyloxy)phenyl)pro-panoylamino]benzoic acid
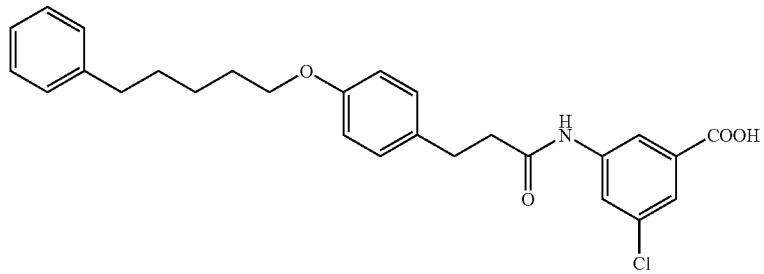
TLC: Rf 0.33 (chloroform:methanol=9:1); NMR (DMSO-d$_6$): δ 10.24 (s, 1H), 8.03–7.99 (m, 2H), 7.53 (t, J=1.8 Hz, 1H), 7.27–7.10 (m, 7H), 6.79 (d, J=8.4 Hz, 2H), 3.87 (t, J=6.6 Hz, 2H), 2.82 (t, J=7.8 Hz, 2H), 2.61–2.54 (m, 4H), 1.73–1.54 (m, 4H), 1.44–1.34 (m, 2H).
EXAMPLE 3(3)
2-(morpholin-4-yl)-5-[3-(4-(5-phenylpentyloxy)phe-nyl)propanoylamino]benzoic acid
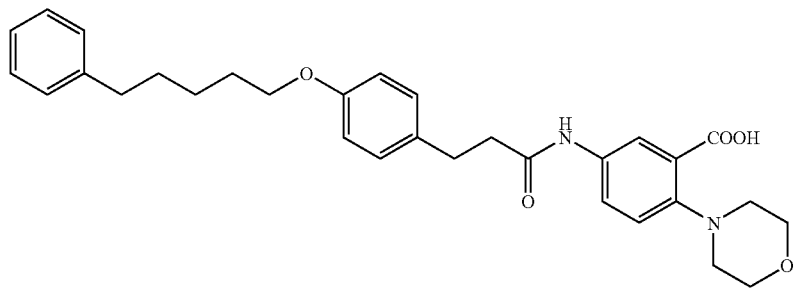
TLC: Rf 0.54 (chloroform:methanol=9:1); NMR (DMSO-d$_6$): δ 10.10 (s, 1H), 8.18 (d, J=2.4 Hz, 1H), 7.87 (dd, J=8.7, 2.4 Hz, 1H), 7.62 (d, J=8.7 Hz, 1H), 7.27–7.10 (m, 7H), 6.82–6.77 (m, 2H), 3.88 (t, J=6.6 Hz, 2H), 3.78–3.75 (m, 4H), 3.02–2.99 (m, 4H), 2.82 (t, J=7.5 Hz, 2H), 2.56 (t, J=7.5 Hz, 4H), 1.76–1.54 (m, 4H), 1.44–1.34 (m, 2H).

EXAMPLE 3(4)

2-(pyrrolidin-1-yl)-5-[3-(4-(5-phenylpentyloxy)phenyl)propanoylamino]benzoic acid

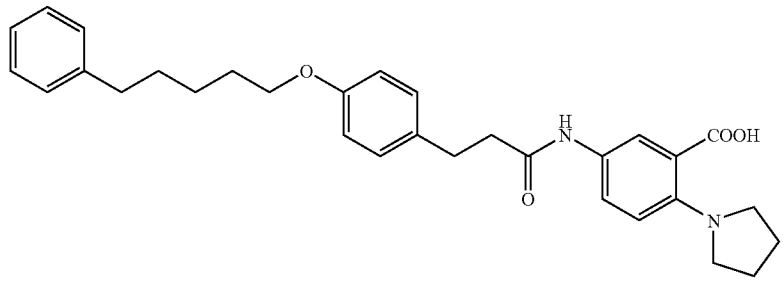

TLC: Rf 0.47 (chloroform:methanol=9:1); NMR (DMSO-$d_6$): δ 9.86 (s, 1H), 7.92 (d, J=2.4 Hz, 1H), 7.66 (dd, J=9.0, 2.4 Hz, 1H), 7.27–7.09 (m, 8H), 6.79 (d, J=9.0 Hz, 2H), 3.88 (t, J=6.6 Hz, 2H), 3.15 (t, J=6.6 Hz, 4H), 2.81 (t, J=7.5 Hz, 2H), 2.59–2.52 (m, 4H), 1.92 (t, J=6.6 Hz, 4H), 1.74–1.54 (m, 4H), 1.44–1.34 (m, 2H).

EXAMPLE 3(5)

6-[3-(4-(5-phenylpentyloxy)phenyl)propanoylamino]pyridine-2-carboxylic acid

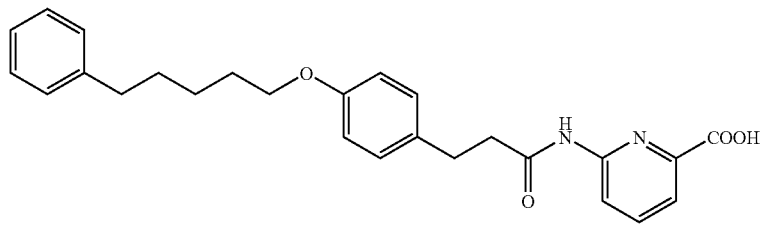

TLC: Rf 0.38 (chloroform:methanol=9:1); NMR (DMSO-$d_6$): δ 10.76 (s, 1H), 8.28 (d, J=8.4 Hz, 1H), 7.94–7.88 (m, 1H), 7.71 (dd, J=7.5 Hz, 0.9 Hz, 1H), 7.27–7.10 (m, 7H), 6.81–6.77 (m, 2H), 3.88 (t, J=6.6 Hz, 2H), 2.81 (t, J=8.1 Hz, 2H) 2.66 (t, J=8.1 Hz, 2H), 2.56 (t, J=7.5 Hz, 2H), 1.73–1.54 (m, 4H), 1.44–1.34 (m, 2H).

EXAMPLE 3(6)

2-[3-(4-(5-phenylpentyloxy)phenyl)propanoylamino]pyridine-4-carboxylic acid

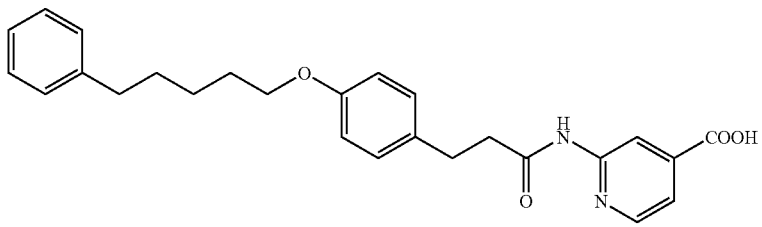

TLC: Rf 0.15 (chloroform:methanol=9:1); NMR (DMSO-d$_6$): δ 10.67 (s, 1H), 8.56 (s, 1H), 8.43 (dd, J=5.1 Hz, 0.6 Hz, 1H), 7.47 (dd, J=5.1 Hz, 1.5 Hz, 1H), 7.27–7.09 (m, 7H), 6.82–6.77 (m, 2H), 3.88 (t, J=6.6 Hz, 2H), 2.81 (t, J=7.2 Hz, 2H) 2.66 (t, J=7.2 Hz, 2H), 2.56 (t, J=8.4 Hz, 2H), 1.73–1.54 (m, 4H), 1.44–1.34 (m, 2H).

EXAMPLE 4

4-chloro-3-[3-(4-(5-phenylpentyloxy)phenyl)propanoylamino]benzoic acid

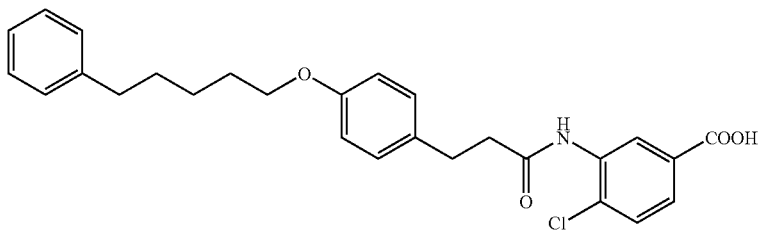

To a solution of the compound prepared in Reference Example 3 (249 mg) in dioxane (2 mL) was added 3-amino-4-chlorobenzoic acid (171 mg) and pyridine (0.07 mL). The reaction mixture was refluxed for 2 hours. To the reaction mixture was added 1N hydrochloric acid. The precipitate was filtered, washed with water and dried to give the compound of the present invention (342 mg) having the following physical data.

TLC: Rf 0.35 (chloroform:methanol=9:1); NMR (DMSO-d$_6$): δ 13.30–13.05 (br, 1H), 9.58 (s, 1H), 8.26 (d, J=2.0 Hz, 1H), 7.68 (dd, J=8.4, 2.0 Hz, 1H), 7.57 (d, J=8.4 Hz, 1H), 7.29–7.12 (m, 7H), 6.80 (d, J=8.4 Hz, 2H), 3.89 (t, J=6.4 Hz, 2H), 2.84 (t, J=6.6 Hz, 2H), 2.70–2.53 (m, 4H), 1.76–1.31 (m, 6H).

EXAMPLE 4(1)–4(10)

By the same procedure as described in Example 4 using the corresponding amine derivatives respectively instead of 3-amino-4-chlorobenzoic acid, the following compounds of the present invention were obtained.

EXAMPLE 4(1)

4-methoxy-3-[3-(4-(5-phenylpentyloxy)phenyl)propanoylamino]benzoic acid

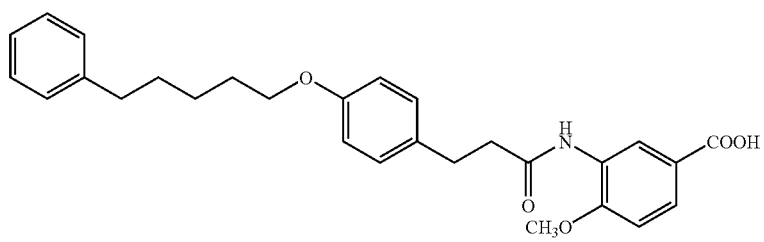

TLC: Rf 0.44 (chloroform:methanol=9:1); NMR (DMSO-$d_6$): δ 12.74–12.52 (br, 1H), 9.16 (s, 1H), 8.55 (d, J=2.0 Hz, 1H), 7.66 (dd, J=8.6, 2.0 Hz, 1H), 7.28–7.06 (m, 8H), 6.80 (d, J=8.6 Hz, 2H), 3.92–3.86 (m, 5H), 2.81 (t, J=7.0 Hz, 2H), 2.69–2.53 (m, 4H), 1.77–1.31 (m, 6H).

EXAMPLE 4(2)

2-hydroxy-5-[3-(4-(5-phenylpentyloxy)phenyl)propanoylamino]benzoic acid

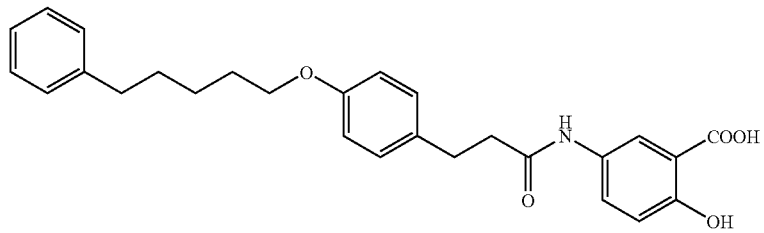

TLC: Rf 0.38 (chloroform:methanol:acetic acid=90:10:1); NMR (DMSO-$d_6$): δ 9.82 (s, 1H), 8.06 (d, J=2.6 Hz, 1H), 7.62 (dd, J=8.8, 2.6 Hz, 1H), 7.28–7.08 (m, 7H), 6.87 (d, J=8.8 Hz, 1H), 6.79 (d, J=8.6 Hz, 2H), 3.89 (t, J=6.4 Hz, 2H), 2.81 (t, J=7.4 Hz, 2H), 2.60–2.51 (m, 4H), 1.76–1.31 (m, 6H).

EXAMPLE 4(3)

2-methyl-5-[3-(4-(5-phenylpentyloxy)phenyl)propanoylamino]benzoic acid

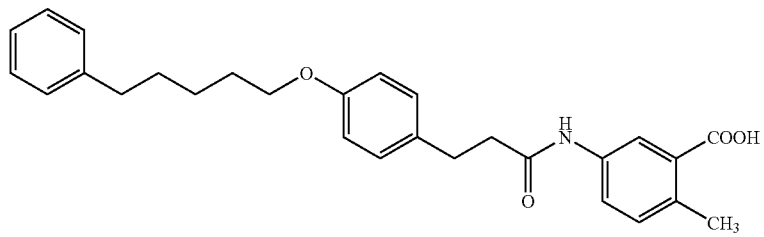

TLC: Rf 0.36 (chloroform:methanol=9:1); NMR (DMSO-$d_6$): δ 12.96–12.56 (br, 1H), 9.93 (s, 1H), 8.04 (d, J=2.2 Hz, 1H), 7.64 (dd, J=8.2, 2.2 Hz, 1H), 7.28–7.09 (m, 8H), 6.79 (d, J=8.6 Hz, 2H), 3.88 (t, J=6.4 Hz, 2H), 2.81 (t, J=7.4 Hz, 2H), 2.60–2.53 (m, 4H), 2.42 (s, 3H), 1.76–1.30 (m, 6H).

EXAMPLE 4(4)
2-fluoro-5-[3-(4-(5-phenylpentyloxy)phenyl)propanoylamino]benzoic acid
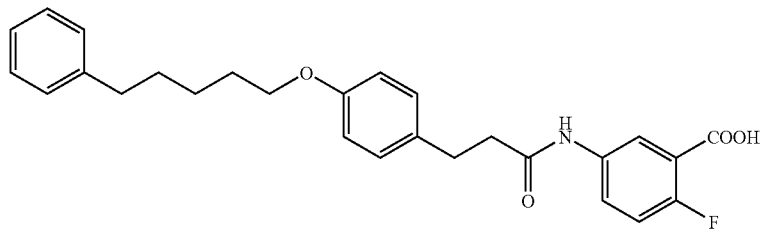
TLC: Rf 0.49 (chloroform:methanol:acetic acid=90:10:1); NMR (DMSO-d$_6$): δ 13.38–13.08 (br, 1H), 10.05 (s, 1H), 8.10 (dd, J=6.8, 2.8 Hz, 1H), 7.80–7.72 (m, 1H), 7.28–7.09 (m, 8H), 6.79 (d, J=8.6 Hz, 2H), 3.88 (t, J=6.4 Hz, 2H), 2.82 (t, J=7.1 Hz, 2H), 2.60–2.53 (m, 4H), 1.76–1.31 (m, 6H).
EXAMPLE 4(5)
2-chloro-3-[3-(4-(5-phenylpentyloxy)phenyl)propanoylamino]benzoic acid
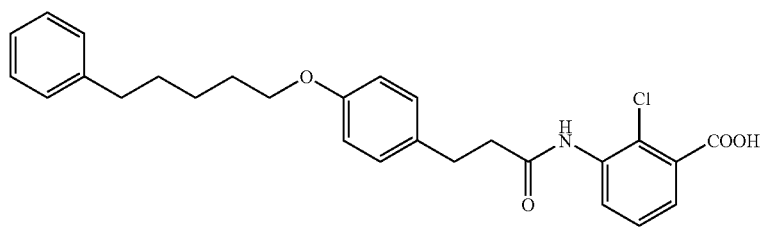
TLC: Rf 0.25 (chloroform:methanol=9:1); NMR (DMSO-d$_6$): δ 13.64–13.18 (br, 1H), 9.55 (s, 1H), 7.74 (dd, J=7.8, 1.8 Hz, 1H), 7.49 (dd, J=7.8, 1.8 Hz, 1H), 7.35 (t, J=7.8 Hz, 1H), 7.29–7.10 (m, 7H), 6.80 (d, J=8.6 Hz, 2H), 3.89 (t, J=6.4 Hz, 2H), 2.83 (t, J=6.9 Hz, 2H), 2.68–2.53 (m, 4H), 1.77–1.32 (m, 6H).

EXAMPLE 4(6)

2-nitro-5-[3-(4-(5-phenylpentyloxy)phenyl)propanoylamino]benzoic acid

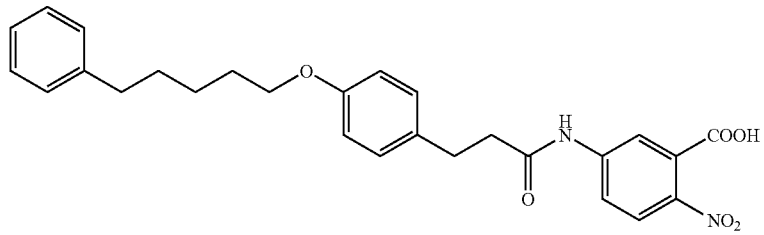

TLC: Rf 0.29 (chloroform:methanol:acetic acid=90:10:1); NMR (DMSO-d$_6$): δ 10.54 (s, 1H), 8.01 (d, J=8.7 Hz, 1H), 7.96 (d, J=2.4 Hz, 1H), 7.81 (dd, J=8.7, 2.4 Hz, 1H), 7.27–7.10 (m, 7H), 6.82–6.77 (m, 2H), 3.87 (t, J=6.6 Hz, 2H), 2.83 (t, J=7.5 Hz, 2H), 2.63 (t, J=7.5 Hz, 2H), 2.56 (t, J=7.5 Hz, 2H), 1.73–1.54 (m, 4H), 1.44–1.33 (m, 2H).

EXAMPLE 4(7)

2-(N,N-diethylamino)-5-[3-(4-(5-phenylpentyloxy)phenyl)propanoylamino]benzoic acid

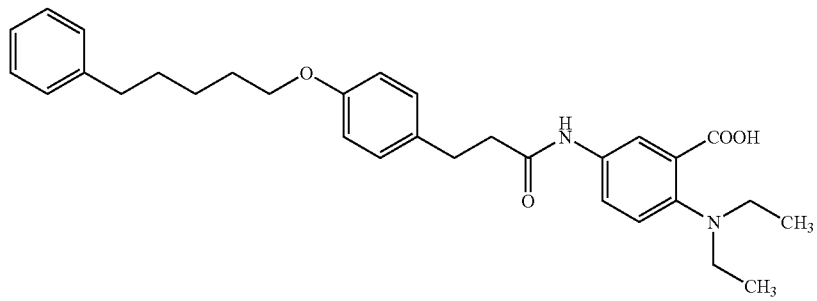

TLC: Rf 0.40 (chloroform:methanol=13:1); NMR (DMSO-d$_6$): δ 10.30 (s, 1H), 8.31 (d, J=2.7 Hz, 1H), 8.00 (dd, J=2.7, 8.7 Hz, 1H), 7.73 (d, J=8.7 Hz, 1H), 7.30–7.15 (m, 5H), 7.14 (d, J=8.4 Hz, 2H), 6.82 (d, J=8.4 Hz, 2H), 3.90 (t, J=6.9 Hz, 2H), 3.36 (t, J=6.6 Hz, 2H), 3.34 (t, J=6.6 Hz, 2H), 2.90–2.80 (m, 2H), 2.60 (q, J=7.5 Hz, 4H), 1.80–1.55 (m, 4H), 1.50–1.35 (m, 2H), 0.92 (t, J=7.5 Hz, 6H).

EXAMPLE 4(8)

2-(2,6-dimethylmorpholin-4-yl)-5-[3-(4-(5-phenyl-pentyloxy)phenyl)propanoylamino]benzoic acid

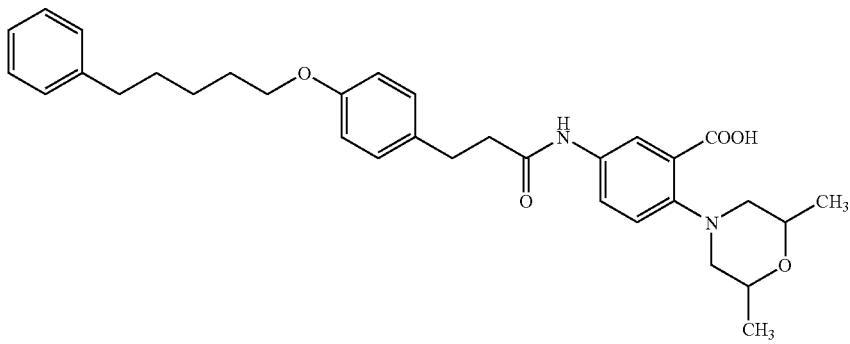

TLC: Rf 0.42 (chloroform:methanol=9:1); NMR (DMSO-$d_6$): δ 10.11 (s, 1H), 8.18 (d, J=2.7 Hz, 1H), 7.87 (dd, J=8.7, 2.7 Hz, 1H), 7.60 (d, J=8.7 Hz, 1H), 7.27–7.10 (m, 7H), 6.82–6.77 (m, 2H), 3.88 (t, J=6.6 Hz, 2H), 3.77–3.68 (m, 2H), 2.95 (d, J=10.8 Hz, 2H), 2.82 (t, J=7.5 Hz, 2H), 2.66 (t, J=10.8 Hz, 2H), 2.56 (t, J=7.5 Hz, 4H), 1.73–1.54 (m, 4H), 1.44–1.34 (m, 2H), 1.12 (d, J=6.0 Hz, 6H).

EXAMPLE 4(9)

2-(N-acetylamino)-5-[3-(4-(5-phenylpentyloxy)phenyl)propanoylamino]benzoic acid

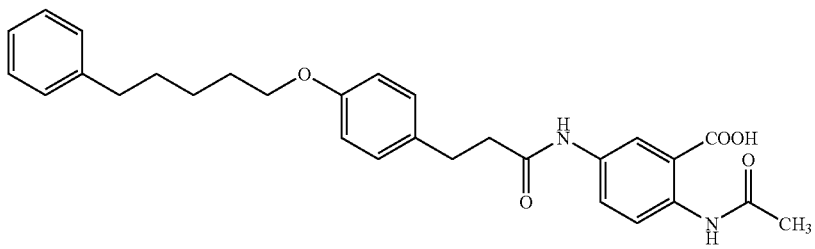

TLC: Rf 0.44 (chloroform:methanol:acetic acid=90:10:1); NMR (DMSO-$d_6$): δ 10.86 (s, 1H), 9.96 (s, 1H), 8.31 (d, J=9.0 Hz, 1H), 8.24 (d, J=2.7 Hz, 1H), 7.69 (dd, J=9.0, 2.7 Hz, 1H), 7.27–7.09 (m, 7H), 6.79 (d, J=8.4 Hz, 2H), 3.88 (t, J=6.6 Hz, 2H), 2.81 (t, J=7.5 Hz, 2H), 2.59–2.49 (m, 4H), 2.08 (s, 3H), 1.73–1.54 (m, 4H), 1.44–1.34 (m, 2H).

EXAMPLE 4(10)

2-(N,N-dimethylamino)-5-[3-(4-(5-phenylpentyloxy)phenyl)propanoylamino]benzoic acid

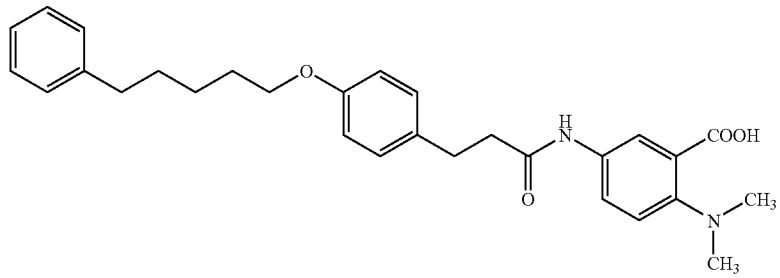

TLC: Rf 0.41 (chloroform:methanol:acetic acid=90:10:1); NMR (DMSO-$d_6$): δ 10.33 (s, 1H), 8.25 (d, J=2.7 Hz, 1H), 7.94 (dd, J=9.0, 2.7 Hz, 1H), 7.81 (d, J=9.0 Hz, 1H), 7.27–7.10 (m, 7H), 6.81–6.77 (m, 2H), 3.87 (t, J=6.6 Hz, 2H), 2.96 (s, 6H), 2.82 (t, J=7.8 Hz, 2H), 2.61–2.53 (m, 4H), 1.73–1.54 (m, 4H), 1.43–1.33 (m, 2H).

EXAMPLE 5 methyl 4-[3-(4-(5-phenylpentyloxy)phenyl)propanoylamino]pyridine-2-carboxylate

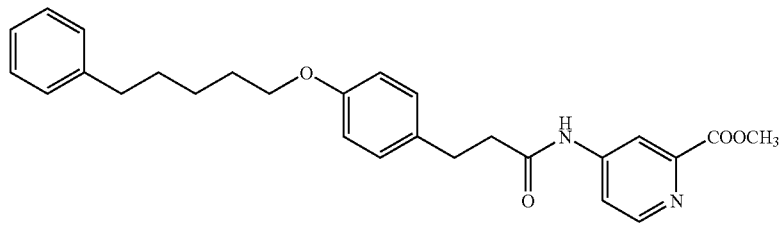

To a solution of the compound prepared in Reference Example 2 (289 mg) in tetrahydrofuran (5 mL) was added triethylamine (0.27 mL). To the mixture was added ethyl chloroformate (0.09 mL) on ice bath. After the mixture was stirred for 10 hours, to the mixture was added a solution of methyl 4-aminopyridine-2-carboxylate (145 mg) in tetrahydrofuran (5 mL). The reaction mixture was refluxed for 2 days. The reaction mixture was concentrated, and the residue was washed with tetrahydrofuran and filtered. The filtrate was concentrated to give the compound of the present invention which is not purified (494 mg). The obtained compound was used without purification.

EXAMPLE 6

4-[3-(4-(5-phenylpentyloxy)phenyl)propanoylamino]pyridine-2-carboxylic acid

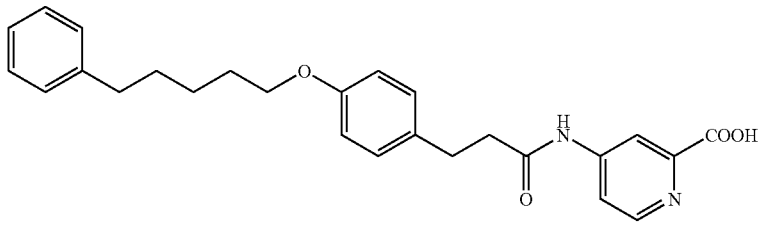

By the same procedure as described in Example 2 using the compound prepared in Example 5 instead of the compound prepared in Example 1, the following compound of the present invention were obtained.

TLC: Rf 0.11 (chloroform:methanol=9:1); NMR (DMSO-$d_6$): δ 10.51 (s, 1H), 8.49 (d, J=5.4 Hz, 1H), 8.23 (d, J=2.1 Hz, 1H), 7.76 (dd, J=5.4 Hz, 2.1 Hz, 1H), 7.27–7.10 (m, 7H), 6.79 (d, J=8.4 Hz, 2H), 3.87 (t, J=6.6 Hz, 2H), 2.83 (t, J=7.5 Hz, 2H) 2.63 (t, J=7.5 Hz, 2H) 2.56 (t, J=7.5 Hz, 2H), 1.73–1.54 (m, 4H), 1.44–1.33 (m, 2H).

EXAMPLE 7 methyl 2-chloro-5-[3-(2-methoxy-4-(5-phenylpentyloxy)phenyl)propanoylamino]benzoate To a mixture of 3-[2-methoxy-4-(5-phenylpentyloxy)phenyl]propanoic acid (342 mg), 1-ethyl-3-[3-(dimethylamino)propyl]carbodiimide hydrochloride (288 mg), 1-hydroxybenzotriazole-1-hydrate (153 mg) and dimethylformamide (5 mL) was added methyl 2-chloro-5-aminobenzoate (265 mg) and triethylamine (0.7 mL). To the reaction mixture was added dimethylaminopyridine (50 mg). The reaction mixture was stirred at room temperature overnight. 1N hydrochloric acid was added to the reaction mixture, which was extracted with ethyl acetate. The extract was washed with saturated aqueous solution of sodium hydrogen carbonate and brine, dried over an anhydrous sodium sulfate and concentrated. The obtained residue was purified by column chromatography on silica gel (hexane:ethyl acetate=4:1) to give the title compound (300 mg) having the following physical data.

TLC: Rf 0.54 (hexane:ethyl acetate=2:1); NMR (CDCl$_3$): δ 7.84 (d, J=2.4 Hz, 1H), 7.64 (dd, J=2.4, 8.7 Hz, 1H), 7.36 (d, J=8.7 Hz, 1H), 7.30–7.15 (m, 5H), 7.05 (d, J=8.4 Hz, 1H), 6.45 (d, J=2.4 Hz, 1H), 6.39 (dd, J=2.4, 8.4 Hz, 1H), 3.93 (t, J=6.6 Hz, 2H), 3.91 (s, 3H), 3.81 (s, 3H), 2.95 (t, J=7.2 Hz, 2H), 2.64 (t, J=7.5 Hz, 2H), 2.62 (t, J=7.5 Hz, 2H), 1.85–1.45 (m, 6H).

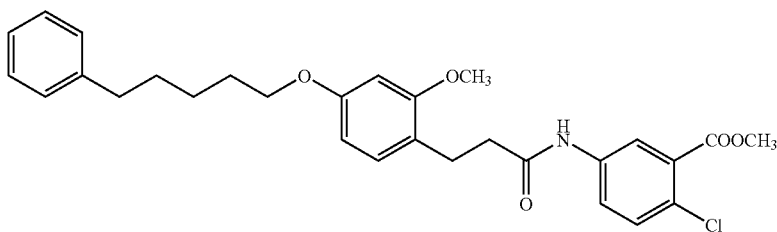

EXAMPLE 7(1)–7(11)

By the same procedure as described in Example 7 using the corresponding amine derivatives respectively instead of methyl 2-chloro-5-aminobenzoate and the corresponding carboxylic acid derivatives respectively instead of 3-[2- methoxy-4-(5-phenylpentyloxy)phenyl]propanoic acid, the following compounds of the present invention were obtained.

EXAMPLE 7(1)

methyl 2-chloro-5-[3-(2-methyl-4-(5-phenylpentyloxy)phenyl)propanoylamino]benzoate

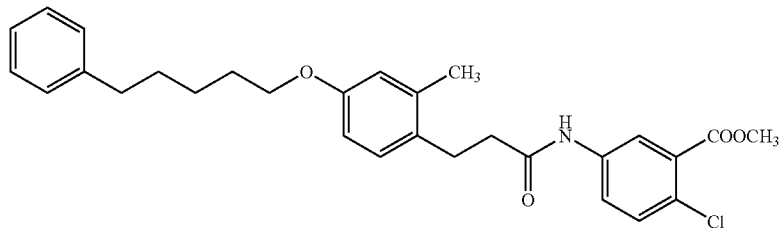

TLC: Rf 0.53 (hexane:ethyl acetate=2:1); NMR (CDCl$_3$): δ 7.85 (m, 1H), 7.65–7.15 (m, 8H), 7.05–7.00 (m, 1H), 6.75–6.60 (m, 2H), 3.90 (s, 3H), 3.95–3.85 (m, 2H), 3.00–2.90 (m, 2H), 2.70–2.50 (m, 4H), 2.28 (s, 3H), 1.85–1.60 (m, 4H), 1.60–1.50 (m, 2H).

EXAMPLE 7(2)

methyl 2-chloro-5-[3-(2-fluoro-4-(5-phenylpentyloxy)phenyl)propanoylamino]benzoate

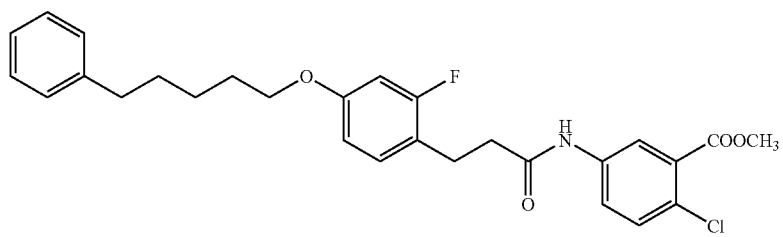

TLC: Rf 0.57 (hexane:ethyl acetate=2:1); NMR (CDCl$_3$): δ 7.87 (d, J=2.7 Hz, 1H), 7.64 (dd, J=2.7, 8.7 Hz, 1H), 7.37 (d, J=8.7 Hz, 1H), 7.30–7.10 (m, 6H), 6.65–6.55 (m, 2H), 3.92 (s, 3H), 3.90 (t, J=6.6 Hz, 2H), 3.05–2.95 (m, 2H), 2.66–2.60 (m, 4H), 1.90–1.50 (m, 6H).

EXAMPLE 7(3)
methyl 2-methoxycarbonyl-5-[3-(2-methyl-4-(5-phenylpentyloxy)phenyl)propanoylamino]benzoate
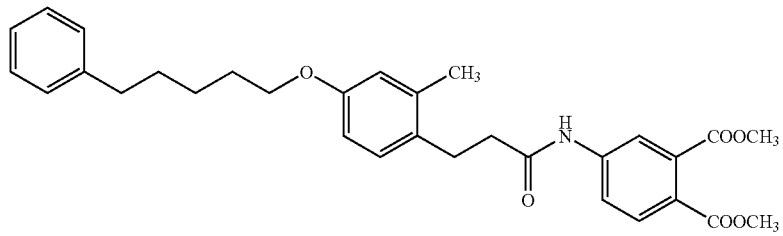
TLC: Rf 0.26 (hexane:ethyl acetate=2:1); NMR (CDCl₃):
δ 7.77–7.66 (m, 3H), 7.31–7.15 (m, 6H), 7.04 (d, J=8.4 Hz, 1H), 6.71 (d, J=2.7 Hz, 1H), 6.66 (dd, J=8.4, 2.7 Hz, 1H), 3.93–3.87 (m, 8H), 2.98 (t, J=7.5 Hz, 2H), 2.64 (t, J=7.5 Hz, 2H), 2.60 (t, J=7.5 Hz, 2H), 2.29 (s, 3H), 1.84–1.64 (m, 4H), 1.55–1.45 (m, 2H).
EXAMPLE 7(4)
methyl 2-methoxycarbonyl-5-[3-(2-fluoro-4-(5-phenylpentyloxy)phenyl)propanoylamino]benzoate
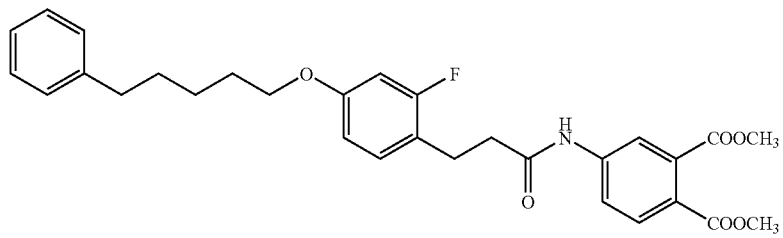
TLC: Rf 0.33 (hexane:ethyl acetate=2:1); NMR (CDCl₃):
δ 7.78–7.69 (m, 3H), 7.35 (s, 1H), 7.30–7.08 (m, 6H), 6.61–6.56 (m, 2H), 3.92–3.87 (m, 8H), 2.99 (t, J=7.5 Hz, 2H), 2.67–2.61 (m, 4H), 1.84–1.64 (m, 4H), 1.54–1.44 (m, 2H).

EXAMPLE 7(5)

methyl 2-methoxycarbonyl-5-[3-(2-methoxy-4-(5-phenylpentyloxy)phenyl)propanoylamino]benzoate

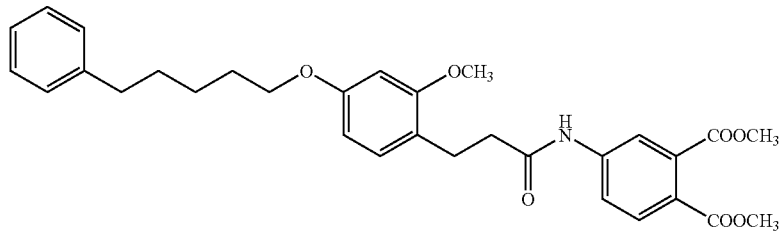

TLC: Rf 0.25 (hexane:ethyl acetate=2:1); NMR (CDCl$_3$):
δ 7.77–7.66 (m, 3H), 7.39 (bs, 1H), 7.31–7.15 (m, 5H), 7.04 (d, J=8.1 Hz, 1H), 6.44 (d, J=2.4 Hz, 1H), 6.39 (dd, J=8.1, 2.4 Hz, 1H), 3.92 (t, J=6.6 Hz, 2H), 3.89 (s, 3H), 3.87 (s, 3H), 3.79 (s, 3H), 2.95 (t, J=7.5 Hz, 2H), 2.67–2.61 (m, 4H), 1.85–1.65 (m, 4H), 1.56–1.45 (m, 2H).

EXAMPLE 7(6)

methyl 2-methoxycarbonyl-5-[3-(3-methoxy-4-(5-phenylpentyloxy)phenyl)propanoylamino]benzoate

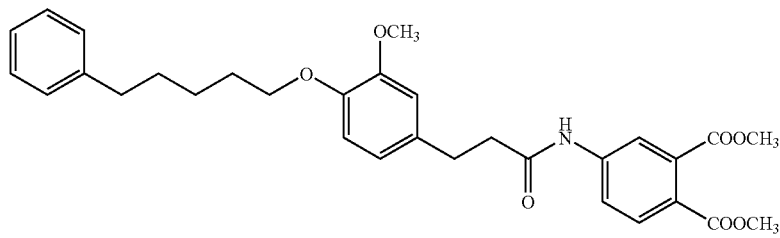

TLC: Rf 0.14 (hexane:ethyl acetate=2:1); NMR (CDCl$_3$):
δ 7.76–7.64 (m, 3H), 7.41 (s, 1H), 7.30–7.15 (m, 5H), 6.80–6.71 (m, 3H), 3.97 (t, J=6.6 Hz, 2H), 3.89 (s, 3H), 3.87 (s, 3H), 3.80 (s, 3H), 2.98 (t, J=7.5 Hz, 2H), 2.67–2.60 (m, 4H), 1.90–1.80 (m, 2H), 1.74–1.63 (m, 2H), 1.54–1.44 (m, 2H).

EXAMPLE 7(7)

methyl 2-chloro-5-[3-(3-methoxy-4-(5-phenylpenty-loxy)phenyl)propanoylamino]benzoate

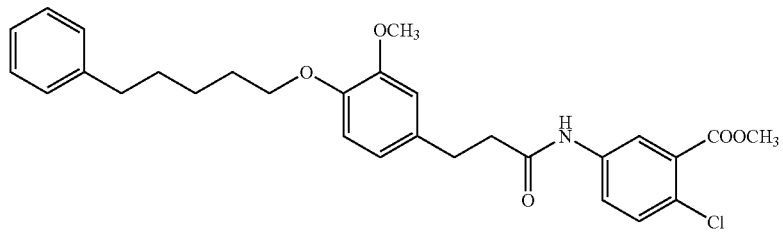

TLC: Rf 0.57 (hexane:ethyl acetate=2:1).

EXAMPLE 7(8)

methyl 2-methoxycarbonyl-5-[3-(4-(4-phenylbuty-loxy)phenyl)propanoylamino]benzoate

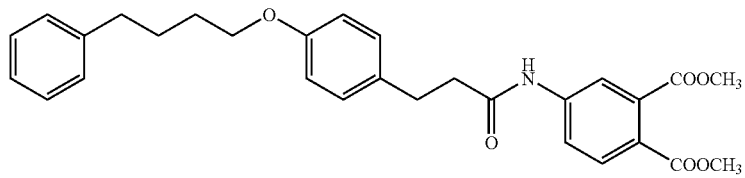

TLC: Rf 0.42 (hexane:ethyl acetate=2:1); NMR (CDCl$_3$): δ 7.76–7.64 (m, 3H), 7.33–7.09 (m, 8H), 6.84–6.79 (m, 2H), 3.96–3.92 (m, 2H), 3.88 (s, 3H), 3.87 (s, 3H), 2.98 (t, J=7.5 Hz, 2H), 2.70–2.61 (m, 4H), 1.82–1.78 (m, 4H).

EXAMPLE 7(9)

methyl 2-methoxycarbonyl-5-[3-(4-(6-phenylhexy-loxy)phenyl)propanoylamino]benzoate

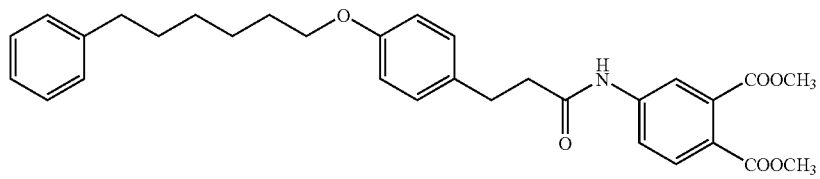

TLC: Rf 0.48 (hexane:ethyl acetate=2:1); NMR (CDCl$_3$): δ 7.77–7.64 (m, 3H), 7.31–7.09 (m, 8H), 6.84–6.79 (m, 2H), 3.93–3.87 (m, 8H), 2.98 (t, J=7.5 Hz, 2H), 2.66–2.59 (m, 4H), 1.81–1.61 (m, 4H), 1.53–1.34 (m, 4H).

EXAMPLE 7(10)
methyl 2-chloro-5-[3-(4-(5-phenylpentylthio)phenyl) propanoylamino]benzoate
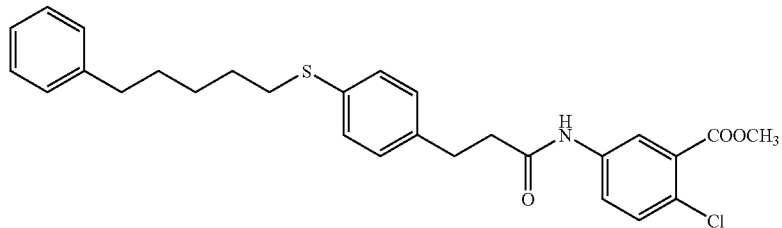
TLC: Rf 0.48 (hexane:ethyl acetate=2:1); NMR (CDCl$_3$): δ 7.86 (d, J=2.7 Hz, 1H), 7.61 (dd, J=2.7, 8.7 Hz, 1H), 7.37 (d, J=8.7 Hz, 1H), 7.30–7.05 (m, 9H), 3.92 (s, 3H), 3.01 (t, J=7.5 Hz, 2H), 2.88 (t, J=7.5 Hz, 2H), 2.64 (t, J=7.5 Hz, 2H), 2.59 (t, J=7.5 Hz, 2H), 1.70–1.40 (m, 6H).
EXAMPLE 7(11)
methyl 2-chloro-5-[3-(4-(5-phenylpentylamino)phenyl)propanoylamino]benzoate
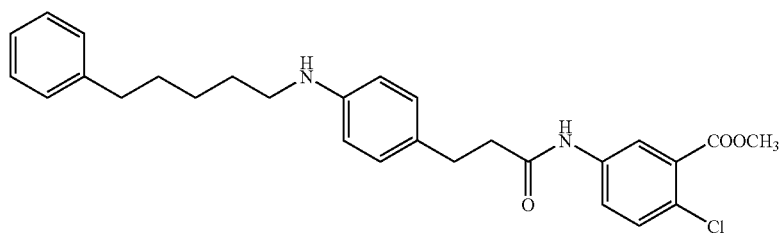
TLC: Rf 0.42 (dichloromethane:ethyl acetate=9:1); NMR (CDCl$_3$): δ 7.84 (d, J=2.7 Hz, 1H), 7.58 (dd, J=8.7, 2.7 Hz, 1H), 7.36 (d, J=8.7 Hz, 1H), 7.31–7.16 (m, 5H), 7.04–7.00 (m, 3H), 6.57–6.52 (m, 2H), 3.91 (s, 3H), 3.08 (t, J=6.9 Hz, 2H), 2.93 (t, J=7.5 Hz, 2H), 2.65–2.58 (m, 4H), 1.72–1.39 (m, 6H).

EXAMPLE 8

2-chloro-5-[3-(2-methoxy-4-(5-phenylpentyloxy)phenyl)propanoylamino]benzoic acid

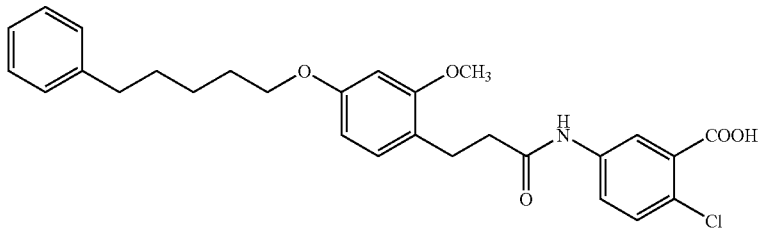

By the same procedure as described in Example 2 using the compound prepared in Example 7 instead of the compound prepared in Example 1, the following compound of the present invention were obtained.

TLC: Rf 0.35 (chloroform:methanol=9:1); NMR (DMSO-d$_6$): δ 13.25 (s, 1H), 10.11 (s, 1H), 8.07 (d, J=2.4 Hz, 1H), 7.71 (dd, J=2.7, 8.7 HZ, 1H), 7.44 (d, J=8.7 HZ, 1H), 7.30–7.10 (m, 5H), 7.01 (d, J=8.4 Hz, 1H), 6.49 (d, J=2.4 Hz, 1H), 6.40 (dd, J=2.4, 8.4 Hz, 1H), 3.91 (t, J=6.3 Hz, 2H), 3.76 (s, 3H), 2.85–2.70 (m, 2H), 2.65–2.50 (m, 4H), 1.80–1.60 (m, 4H), 1.50–1.40 (m, 2H).

EXAMPLE 8(1)-8(11)

By the same procedure as described in Example 8 using the compounds prepared in Example 7(1)-7(11) respectively instead of the compound prepared in Example 7, the following compounds of the present invention were obtained.

EXAMPLE 8(1)

2-chloro-5-[3-(2-methyl-4-(5-phenylpentyloxy)phenyl)propanoylamino]benzoic acid

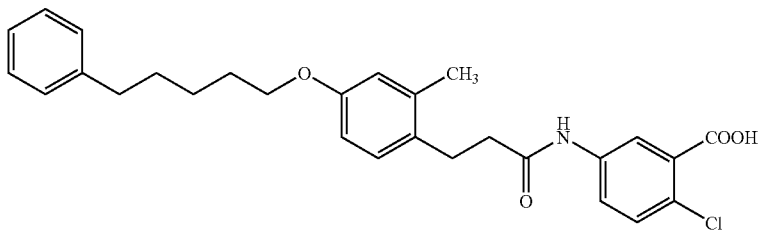

TLC: Rf 0.26 (chloroform:methanol=9:1); NMR (DMSO-d$_6$): δ 13.35 (s, 1H), 10.15 (s, 1H), 8.08 (d, J=2.7 Hz, 1H), 7.72 (dd, J=2.7, 8.7 Hz, 1H), 7.45 (d, J=8.7 Hz, 1H), 7.30–7.10 (m, 5H), 7.04 (d, J=8.4 Hz, 1H), 6.71 (d, J=2.7 Hz, 1H), 6.65 (dd, J=2.7, 8.4 Hz, 1H), 3.89 (t, J=6.6 Hz, 2H), 2.82 (t, J=7.8 Hz, 2H), 2.60–2.50 (m, 4H), 2.26 (s, 3H), 1.80–1.60 (m, 4H), 1.50–1.40 (m, 2H).

EXAMPLE 8(2)

methyl 2-chloro-5-[3-(2-fluoro-4-(5-phenylpentyloxy)phenyl)propanoylamino]benzoic acid

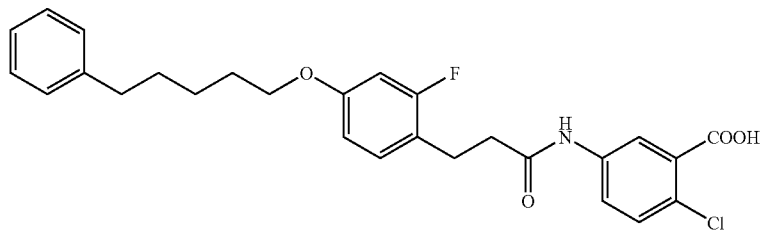

TLC: Rf 0.22 (chloroform:methanol=9:1); NMR (DMSO-d$_6$): δ 13.35 (s, 1H), 10.17 (s, 1H), 8.06 (d, J=2.7 Hz, 1H), 7.70 (dd, J=2.7, 8.7 Hz, 1H), 7.44 (d, J=8.7 Hz, 1H), 7.30–7.10 (m, 6H), 6.73 (dd, J=2.7, 12.6 Hz, 1H), 6.67 (dd, J=2.1, 8.4 Hz, 1H), 3.92 (t, J=6.3 Hz, 2H), 2.85 (t, J=7.2 Hz, 2H), 2.59 (t, J=7.5 Hz, 4H), 1.80–1.60 (m, 4H), 1.55–1.40 (m, 2H).

EXAMPLE 8(3)

2-carboxy-5-[3-(2-methyl-4-(5-phenylpentyloxy)phenyl)propanoylamino]benzoic acid

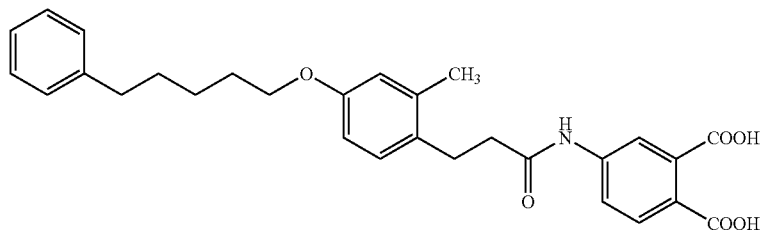

TLC: Rf 0.46 (chloroform:methanol:acetic acid=9:1:1); NMR (DMSO-d$_6$): δ 10.23 (s, 1H), 7.84–7.83 (m, 1H), 7.72–7.66 (m, 2H), 7.27–7.11 (m, 5H), 7.02 (d, J=8.1 Hz, 1H), 6.69 (d, J=2.4 Hz, 1H), 6.63 (dd, J=8.1, 2.4 Hz, 1H), 3.86 (t, J=6.6 Hz, 2H), 2.80 (t, J=7.5 Hz, 2H), 2.59–2.52 (m, 4H), 2.24 (s, 3H), 1.73–1.54 (m, 4H), 1.43–1.33 (m, 2H).

EXAMPLE 8(4)

2-carboxy-5-[3-(2-fluoro-4-(5-phenylpentyloxy)phenyl)propanoylamino]benzoic acid

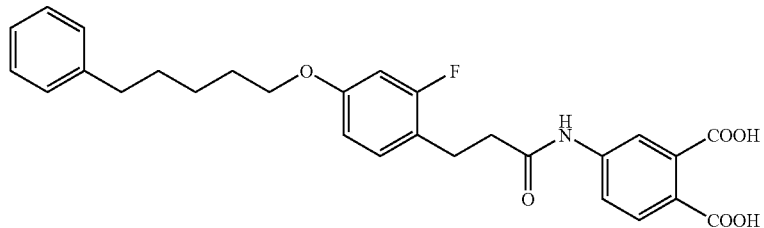

TLC: Rf 0.37 (chloroform:methanol:acetic acid=9:1:1);
NMR (DMSO-$d_6$): δ 10.25 (s, 1H), 7.82 (s, 1H), 7.67 (s, 2H), 7.27–7.11 (m, 6H), 6.75–6.64 (m, 2H), 3.90 (t, J=6.6 Hz, 2H), 2.83 (t, J=7.5 Hz, 2H), 2.62–2.54 (m, 4H), 1.73–1.54 (m, 4H), 1.43–1.33 (m, 2H).

EXAMPLE 8(5)

2-carboxy-5-[3-(2-methoxy-4-(5-phenylpentyloxy)phenyl)propanoylamino]benzoic acid

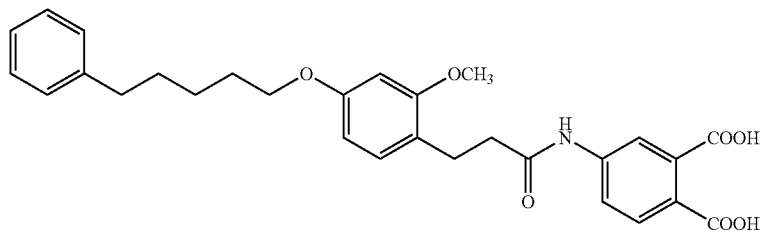

TLC: Rf 0.38 (chloroform:methanol:acetic acid=9:1:1);
NMR (DMSO-$d_6$): δ 10.19 (s, 1H), 7.83 (d, J=1.2 Hz, 1H), 7.72–7.65 (m, 2H), 7.28–7.11 (m, 5H), 7.00 (d, J=8.4 Hz, 1H), 6.47 (d, J=2.1 Hz, 1H), 6.38 (dd, J=8.4, 2.1 Hz, 1H), 3.89 (t, J=6.3 Hz, 2H), 3.74 (s, 3H), 2.77 (t, J=7.5 Hz, 2H), 2.59–2.49 (m, 4H), 1.74–1.55 (m, 4H), 1.45–1.34 (m, 2H).

EXAMPLE 8(6)

2-carboxy-5-[3-(3-methoxy-4-(5-phenylpentyloxy)phenyl)propanoylamino]benzoic acid

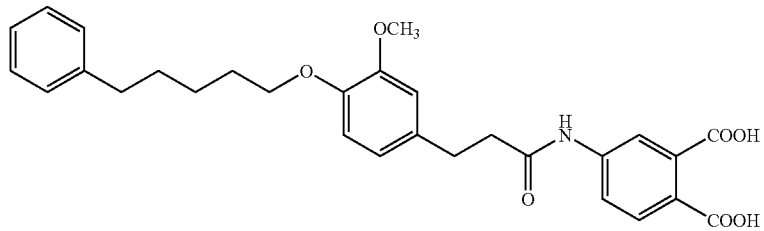

TLC: Rf 0.33 (chloroform:methanol:acetic acid=9:1:1);
NMR (DMSO-$d_6$): δ 10.24 (s, 1H), 7.83 (s, 1H), 7.72–7.66 (m, 2H), 7.27–7.11 (m, 5H), 6.80 (d, J=7.8 Hz, 2H), 6.69 (dd, J=8.1, 1.8 Hz, 1H), 3.85 (t, J=6.6 Hz, 2H), 3.68 (s, 3H), 2.83 (t, J=7.5 Hz, 2H), 2.63–2.54 (m, 4H), 1.73–1.54 (m, 4H), 1.44–1.34 (m, 2H).

EXAMPLE 8(7)

2-chloro-5-[3-(3-methoxy-4-(5-phenylpentyloxy)phenyl)propanoylamino]benzoic acid

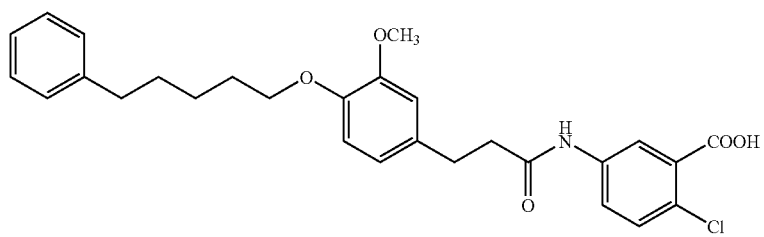

TLC: Rf 0.24 (chloroform:methanol=9:1); NMR (DMSO-$d_6$): δ 10.16 (s, 1H), 8.08 (d, J=2.7 Hz, 1H), 7.72 (dd, J=2.7, 8.7 Hz, 1H), 7.45 (d, J=8.7 Hz, 1H), 7.30–7.15 (m, 5H), 6.83 (d, J=2.1 Hz, 1H), 6.82 (d, J=8.1 Hz, 1H), 6.71 (dd, J=2.1, 8.1 Hz, 1H), 3.88 (t, J=6.3 Hz, 2H), 3.71 (s, 3H), 2.90–2.80 (m, 2H), 2.65–2.55 (m, 4H), 1.80–1.55 (m, 4H), 1.50–1.40 (m, 2H).

EXAMPLE 8(8)

2-carboxy-5-[3-(4-(4-phenylbutyloxy)phenyl)propanoylamino]benzoic acid

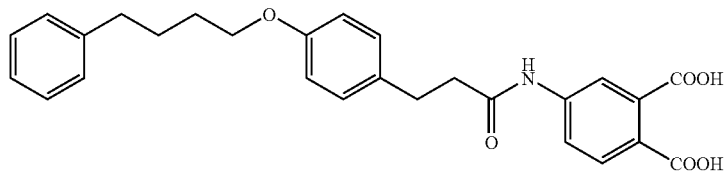

TLC: Rf 0.23 (chloroform:methanol:acetic acid=9:1:1);
NMR (DMSO-$d_6$): δ 10.23 (s, 1H), 7.83 (s, 1H), 7.71–7.65 (m, 2H), 7.28–7.10 (m, 7H), 6.80 (d, J=8.7 Hz, 2H), 3.91 (t, J=6.0 Hz, 2H), 2.82 (t, J=7.5 Hz, 2H), 2.62–2.57 (m, 4H), 1.72–1.63 (m, 4H).

EXAMPLE 8(9)

2-carboxy-5-[3-(4-(6-phenylhexyloxy)phenyl)propanoylamino]benzoic acid

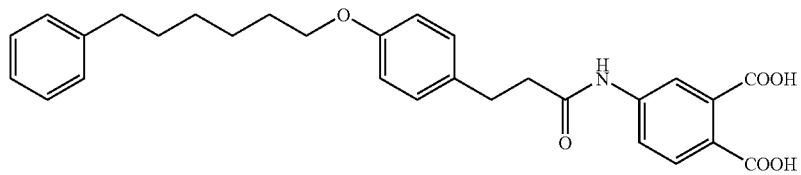

TLC: Rf 0.23 (chloroform:methanol:acetic acid=9:1:1);
NMR (DMSO-$d_6$): δ 10.23 (s, 1H), 7.84 (s, 1H), 7.72–7.66 (m, 2H), 7.26–7.10 (m, 7H), 6.79 (d, J=8.4 Hz, 2H), 3.87 (t, J=6.6 Hz, 2H), 2.82 (t, J=7.5 Hz, 2H), 2.62–2.52 (m, 4H), 1.69–1.51 (m, 4H), 1.45–1.25 (m, 4H).

EXAMPLE 8(10)

2-chloro-5-[3-(4-(5-phenylpentylthio)phenyl)propanoylamino]benzoic acid

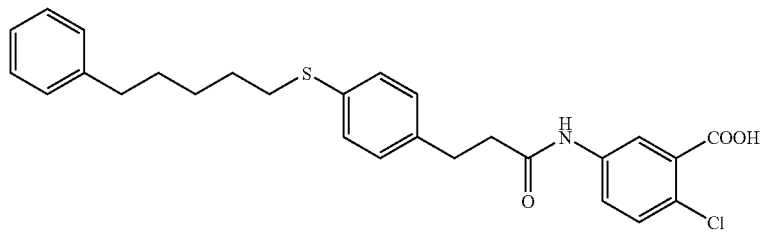

TLC: Rf 0.39 (chloroform:methanol=4:1); NMR (DMSO-$d_6$): δ 13.35 (s, 1H), 10.16 (s, 1H), 8.07 (d, J=2.7 Hz, 1H), 7.70 (dd, J=2.7, 8.7 Hz, 1H), 7.44 (d, J=8.7 Hz, 1H), 7.30–7.15 (m, 9H), 2.90 (t, J=7.5 Hz, 2H), 2.87 (t, J=7.5 Hz, 2H), 2.61 (t, J=7.5 Hz, 2H), 2.54 (t, J=6.9 Hz, 2H), 1.65–1.50 (m, 4H), 1.45–1.35 (m, 2H).

EXAMPLE 8(11)

2-chloro-5-[3-(4-(5-phenylpentylamino)phenyl)propanoylamino]benzoic acid hydrochloride

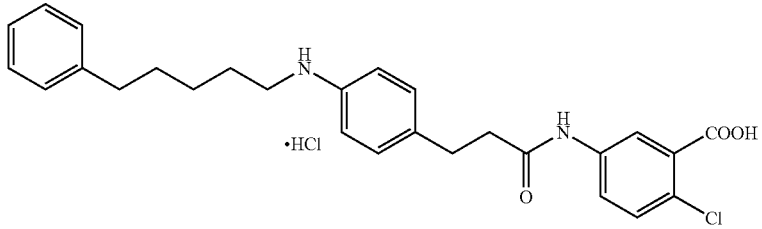

TLC: Rf 0.36 (chloroform:methanol:acetic acid=90:10:1); NMR (DMSO-$d_6$): δ 10.30 (s, 1H), 8.06 (d, J=2.7 Hz, 1H), 7.70 (dd, J=8.7, 2.7 Hz, 1H), 7.42 (d, J=8.7 Hz, 1H), 7.33–7.11 (m, 9H), 3.17 (t, J=8.1 Hz, 2H), 2.91 (t, J=7.5 Hz, 2H), 2.64 (t, J=7.5 Hz, 2H), 2.53 (t, J=7.5 Hz, 2H), 1.67–1.50 (m, 4H), 1.36–1.26 (m, 2H).

EXAMPLE 9

3-[3-(4-(6-phenylhexyl)phenyl)propanoylamino]benzoic acid

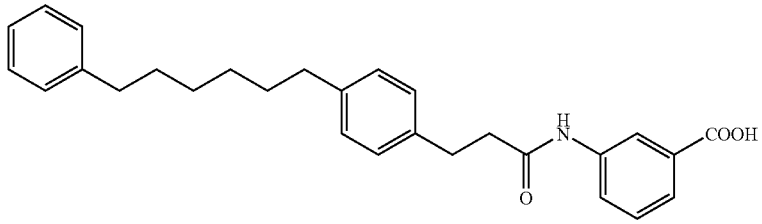

By the same procedure as described in Example 7→Example 8 using methyl 3-aminobenzoate instead of methyl 2-chloro-5-aminobenzoate and 3-[4-(6-phenylhexyl)phenyl]propanoic acid instead of 3-[2-methoxy-4-(5-phenylpentyloxy)phenyl]propanoic acid, the compound of the present invention having the following physical data were obtained.

TLC: Rf 0.37 (chloroform:methanol=9:1); NMR (DMSO-$d_6$): δ 13.05–12.72 (br, 1H), 10.06 (s, 1H), 8.20–8.19 (m, 1H), 7.81–7.76 (m, 1H), 7.61–7.55 (m, 1H), 7.38 (t, J=7.8 Hz, 1H), 7.28–7.03 (m, 9H), 2.86 (t, J=7.4 Hz, 2H), 2.63–2.45 (m, 6H), 1.60–1.40 (br, 4H), 1.33–1.20 (br, 4H).

EXAMPLE 9(1)-9(8)

By the same procedure as described in Example 9 using the corresponding amino derivatives respectively instead of methyl 3-aminobenzoate and the corresponding carboxylic acid derivatives respectively instead of 3-[4-(6-phenylhexyl)phenyl]propanoic acid, the following compounds of the present invention were obtained.

EXAMPLE 9(1)

3-[3-(4-(5-cyclohexylpentyloxy)phenyl)propanoylamino]benzoic acid

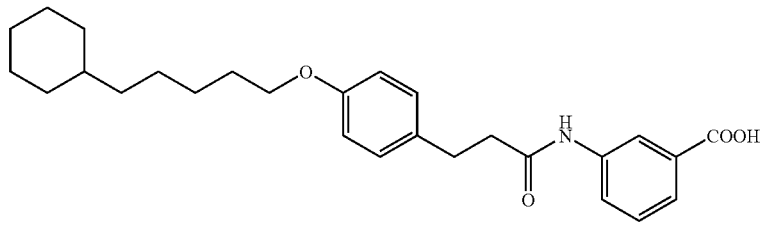

TLC: Rf 0.44 (chloroform:methanol=9:1); NMR (DMSO-$d_6$): δ 12.90 (s, 1H), 10.05 (s, 1H), 8.19 (t, J=1.6 Hz, 1H), 7.81–7.76 (m, 1H), 7.60–7.55 (m, 1H), 7.38 (t, J=7.9 Hz, 1H), 7.12 (d, J=8.6 Hz, 2H), 6.80 (d, J=8.6 Hz, 2H), 3.87 (t, J=6.4 Hz, 2H), 2.82 (t, J=7.6 Hz, 2H), 2.57 (t, J=7.6 Hz, 2H), 1.74–1.50 (br, 7H), 1.40–1.02 (m, 10H), 0.89–0.73 (m, 2H).

EXAMPLE 9(2)

2-chloro-5-[3-(4-(4-(4-methylphenyl)butyloxy)phenyl)propanoylamino]benzoic acid

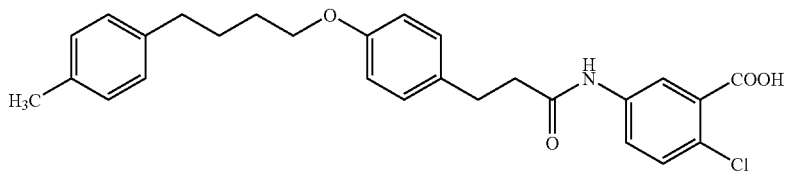

TLC: Rf 0.24 (chloroform:methanol=9:1); NMR (DMSO-$d_6$): δ 13.30 (s, 1H), 10.15 (s, 1H), 8.07 (d, J=2.7 Hz, 1H), 7.71 (dd, J=2.7, 8.7 Hz, 1H), 7.43 (d, J=8.7 Hz, 1H), 7.13 (d, J=8.4 Hz, 2H), 7.07 (s, 4H), 6.81 (d, J=8.4 Hz, 2H), 3.91 (m, 2H), 2.83 (t, J=7.5 Hz, 2H), 2.65–2.55 (m, 4H), 2.25 (s, 3H), 1.68 (m, 4H).

EXAMPLE 9(3)

2-chloro-5-[3-(4-(4-(4-methoxyphenyl)butyloxy)phenyl)propanoylamino]benzoic acid

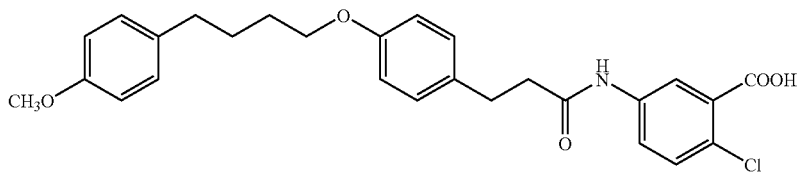

TLC: Rf 0.41 (chloroform:methanol=9:1); NMR (DMSO-$d_6$): δ 13.35 (s, 1H), 10.14 (s, 1H), 8.07 (d, J=2.7 Hz, 1H), 7.71 (dd, J=2.7, 8.7 Hz, 1H), 7.44 (d, J=8.7 Hz, 1H), 7.15–7.05 (m, 4H), 6.85–6.80 (m, 4H), 3.92 (t, J=6.0 Hz, 2H), 3.71 (s, 3H), 2.84 (t, J=7.5 Hz, 2H), 2.65–2.50 (m, 4H), 1.70–1.65 (m, 4H).

EXAMPLE 9(4)

2-carboxy-5-[3-(4-(4-(4-methoxyphenyl)butyloxy)phenyl)propanoylamino]benzoic acid

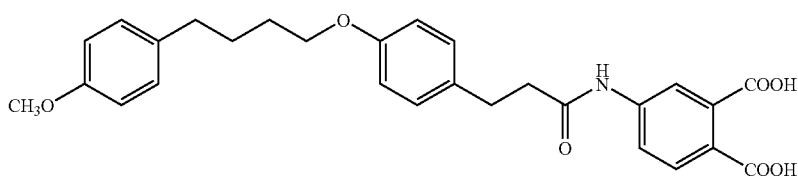

TLC: Rf 0.29 (chloroform:methanol:acetic acid=13:1:1); NMR (DMSO-$d_6$): δ 10.24 (s, 1H), 7.84 (d, J=2.7 Hz, 1H), 7.75–7.65 (m, 2H), 7.13 (d, J=9.0 Hz, 2H), 7.11 (d, J=8.7 Hz, 2H), 6.83 (d, J=9.0 Hz, 2H), 6.82 (d, J=8.7 Hz, 2H), 3.92 (t, J=6.0 Hz, 2H), 3.71 (s, 3H), 2.84 (t, J=7.5 Hz, 2H), 2.61 (t, J=7.8 Hz, 2H), 2.60–2.50 (m, 2H), 1.70–1.65 (m, 4H).

EXAMPLE 9(5)

2-chloro-5-[3-(2-methoxy-4-(5-(pyridin-4-yl)pentyloxy)phenyl)propanoylamino]benzoic acid

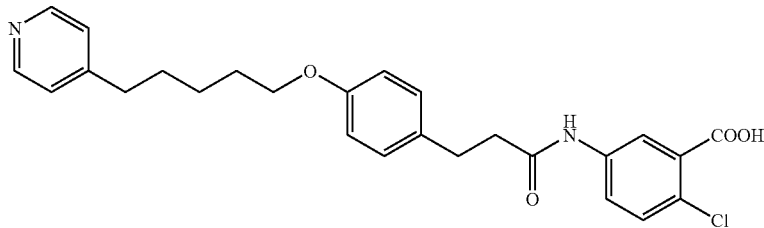

TLC: Rf 0.20 (chloroform:methanol:acetic acid=90:10:1); NMR (DMSO-$d_6$): δ 10.15 (s, 1H), 8.44–8.41 (m, 2H), 8.05 (d, J=2.7 Hz, 1H), 7.69 (dd, J=8.7, 2.7 Hz, 1H), 7.43 (d, J=8.7 Hz, 1H), 7.24–7.22 (m, 2H), 7.13–7.07 (m, 2H), 6.81–6.77 (m, 2H), 3.88 (t, J=6.6 Hz, 2H), 2.81 (t, J=7.5 Hz, 2H), 2.62–2.54 (m, 4H), 1.74–1.57 (m, 4H), 1.44–1.33 (m, 2H).

EXAMPLE 9(6)

2,3-dichloro-5-[3-(4-(5-phenylpentyloxy)phenyl)propanoylamino]benzoic acid

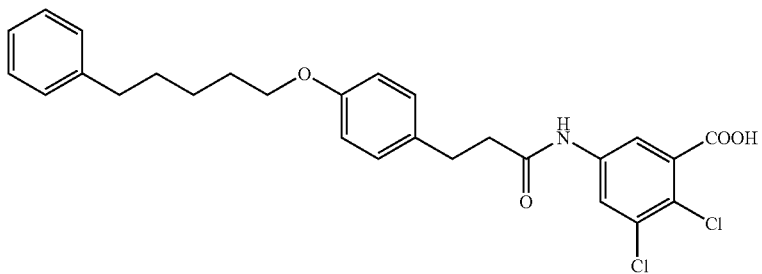

TLC: Rf 0.43 (chloroform:methanol:acetic acid=90:10:1); NMR (DMSO-$d_6$): δ 13.86–13.50 (br, 1H), 10.28 (s, 1H), 8.04 (d, J=2.7 Hz, 1H), 7.85 (d, J=2.7 Hz, 1H), 7.27–7.09 (m, 7H), 6.79 (d, J=8.7 Hz, 2H), 3.88 (t, J=6.6 Hz, 2H), 2.81 (t, J=7.5 Hz, 2H), 2.60–2.54 (m, 4H), 1.73–1.54 (m, 4H), 1.44–1.38 (m, 2H).

EXAMPLE 9(7)

2-methoxy-3-carboxy-5-[3-(4-(5-phenylpentyloxy)phenyl)propanoylamino]benzoic acid

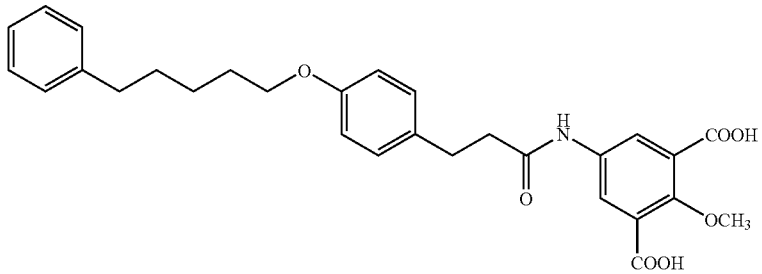

TLC: Rf 0.43 (chloroform:methanol:acetic acid=9:1:1); NMR (DMSO-$d_6$): δ 13.15–12.90 (br, 2H), 10.08 (s, 1H), 8.04 (s, 2H), 7.27–7.09 (m, 7H), 6.79 (d, J=8.7 Hz, 2H), 3.88 (t, J=6.6 Hz, 2H), 3.74 (s, 3H), 2.81 (t, J=7.5 Hz, 2H), 2.59–2.52 (m, 4H), 1.73–1.54 (m, 4H), 1.44–1.34 (m, 2H).

EXAMPLE 9(8)

2-nitro-5-[3-(3-methoxy-4-(5-phenylpentyloxy)phenyl)propanoylamino]benzoic acid

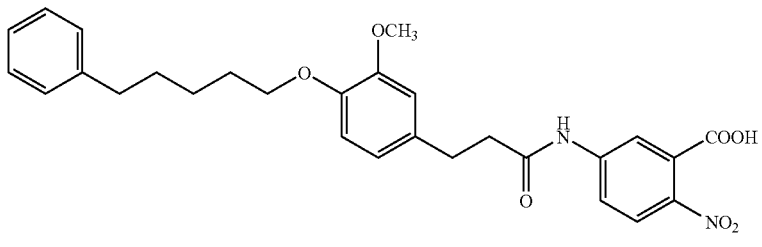

TLC: Rf 0.44 (chloroform:methanol=4:1); NMR (DMSO-$d_6$): δ 10.56 (s, 1H), 8.03 (d, J=8.7 Hz, 1H), 7.99 (d, J=2.4 Hz, 1H), 7.83 (dd, J=2.4, 8.7 Hz, 1H), 7.30–7.10 (m, 5H), 6.84 (d, J=1.8 Hz, 1H), 6.83 (d, J=8.1 Hz, 1H), 6.71 (dd, J=1.8, 8.1 Hz, 1H), 3.88 (t, J=6.6 Hz, 2H), 3.71 (s, 3H), 2.95–2.80 (m, 2H), 2.80–2.50 (m, 4H), 1.80–1.60 (m, 4H), 1.50–1.40 (m, 2H).

EXAMPLE 10

2-chloro-3-[3-(4-(5-(thiophen-2-yl)pentyloxy)phenyl)propanoylamino]benzoic acid

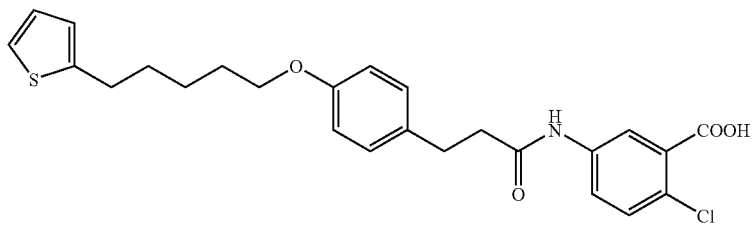

By the same procedure as described in Reference Example 3→Example 4 using 3-[4-(5-(thiophen-2-yl)pentyloxy)phenyl]propanoic acid instead of the compound prepared in Reference Example 2 and 2-chloro-5-aminobenzoic acid instead of 3-amino-4-chlorobenzoic acid, the compound of the present invention having the following physical data were obtained.

TLC: Rf 0.53 (chloroform:methanol:acetic acid=90:10:1); NMR (DMSO-$d_6$): δ 13.43–13.26 (br, 1H), 10.13 (s, 1H), 8.05 (d, J=2.4 Hz, 1H), 7.69 (dd, J=8.7, 3.0 Hz, 1H), 7.43 (d, J=8.7 Hz, 1H), 7.27 (dd, J=5.1, 1.5 Hz, 1H), 7.11 (d, J=8.4 Hz, 2H), 6.90 (dd, J=5.1, 3.3 Hz, 1H), 6.82–6.78 (m, 3H), 3.88 (t, J=6.6 Hz, 2H), 2.84–2.76 (m, 4H), 2.56 (t, J=7.5 Hz, 2H) 1.74–1.59 (m, 4H), 1.47–1.37 (m, 2H).

EXAMPLE 10(1)-10(6)

By the same procedure as described in Example 10 using the corresponding carboxylic acid derivatives respectively instead of 3-[4-(5-(thiophen-2-yl)pentyloxy)phenyl]propanoic acid and the corresponding amine derivatives respectively instead of 2-chloro-5-aminobenzoic acid, the following compounds of the present invention were obtained.

EXAMPLE 10(1)
2-chloro-5-[(6-(5-phenylpentyloxy)naphthalen-2-yl)carbonylamino]benzoic acid
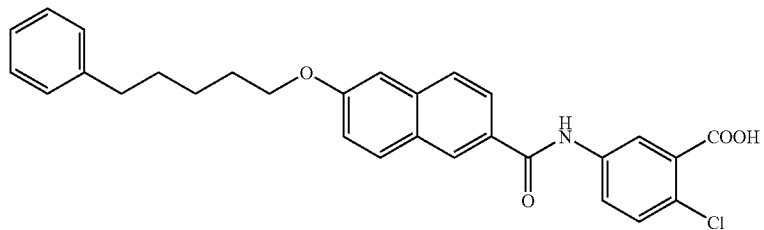
TLC: Rf 0.51 (chloroform:methanol:acetic acid=90:10:1); NMR (DMSO-d$_6$): δ 10.49 (s, 1H), 8.52 (s, 1H), 8.13–7.83 (m, 5H), 7.40–7.11 (m, 8H), 4.09 (t, J=6.4 Hz, 2H), 2.60 (t, J=7.2 Hz, 2H), 1.88–1.42 (m, 6H).
EXAMPLE 10(2)
2-chloro-5-[3-(4-(5-(4-methylphenyl)pentyloxy)phenyl)propanoylamino]benzoic acid
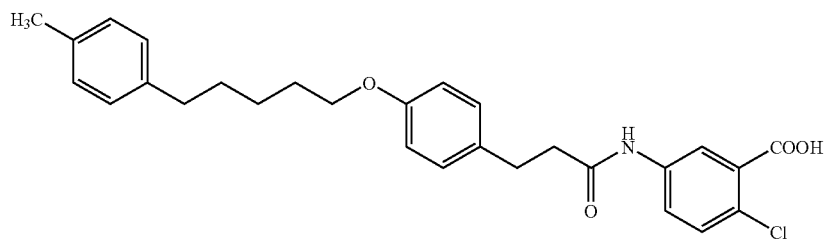
TLC: Rf 0.31 (chloroform:methanol=9:1); NMR (DMSO-d$_6$): δ 13.36 (brs, 1H), 10.14 (s, 1H), 8.07 (d, J=2.7 Hz, 1H), 7.70 (dd, J=2.7, 8.7 Hz, 1H), 7.43 (d, J=8.7 Hz, 1H), 7.12 (d, J=8.4 Hz, 2H), 7.06 (s, 4H), 6.81 (d, J=8.4 Hz, 2H), 3.89 (t, J=6.6 Hz, 2H), 2.83 (t, J=7.5 Hz, 2H), 2.60–2.40 (m, 4H), 2.25 (s, 3H), 1.80–1.55 (m, 4H), 1.50–1.35 (m, 2H).

EXAMPLE 10(3)

2-chloro-5-[2-methyl-3-(4-(5-phenylpentyloxy)phenyl)propanoylamino]benzoic acid

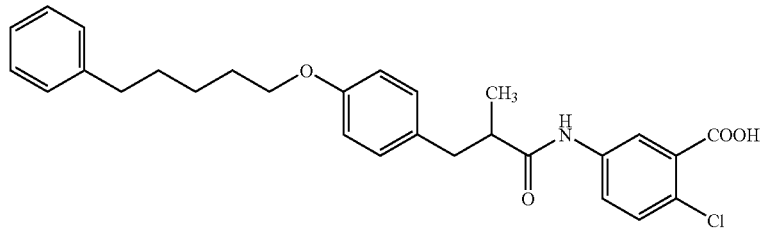

TLC: Rf 0.36 (chloroform:methanol=9:1); NMR (DMSO-$d_6$): δ 13.36 (s, 1H), 10.08 (s, 1H), 8.06 (d, J=2.4 Hz, 1H), 7.70 (dd, J=2.4, 8.7 Hz, 1H), 7.44 (d, J=8.7 Hz, 1H), 7.30–7.15 (m, 5H), 7.09 (d, J=8.7 Hz, 2H), 6.70 (d, J=8.7 Hz, 2H), 3.89 (t, J=6.3 Hz, 2H), 2.88 (dd. J=7.5, 12.9 Hz, 1H), 2.75–2.65 (m, 1H), 2.58 (t, J=7.5 Hz, 2H), 2.55–2.50 (m, 1H), 1.75–1.55 (m, 4H), 1.45–1.35 (m, 2H), 1.07 (d, J=6.9 Hz, 3H).

EXAMPLE 10(4)

2-chloro-5-[3-(4-(4-phenylbutyloxy)phenyl)propanoylamino]benzoic acid

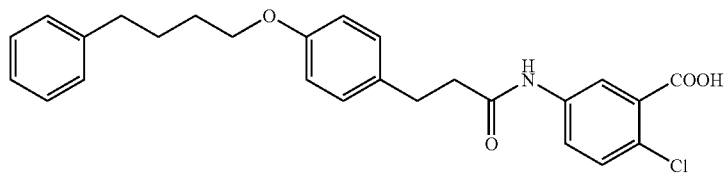

TLC: Rf 0.19 (chloroform:methanol=9:1); NMR (DMSO-$d_6$): δ 13.30 (s, 1H), 10.15 (s, 1H), 8.07 (d, J=2.7 Hz, 1H), 7.71 (dd, J=2.7, 8.7 Hz, 1H), 7.43 (d, J=8.7 Hz, 1H), 7.30–7.15 (m, 5H), 7.13 (d, J=8.7 Hz, 2H), 6.82 (d, J=8.7 Hz, 2H), 3.93 (m, 2H), 2.84 (t, J=7.5 Hz, 2H), 2.65–2.55 (m, 4H), 1.80–1.70 (m, 4H).

EXAMPLE 10(5)

2-chloro-5-[3-(4-(6-phenylhexyloxy)phenyl)propanoylamino]benzoic acid

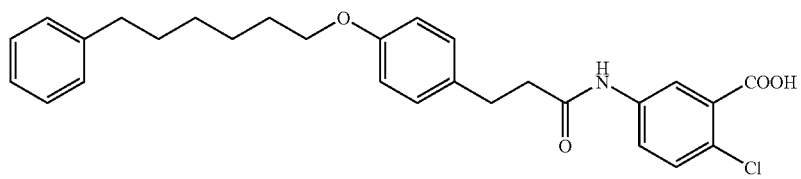

TLC: Rf 0.34 (chloroform:methanol=9:1); NMR (DMSO-$d_6$): δ 10.30 (s, 1H), 10.12 (s, 1H), 8.05 (d, J=2.7 Hz, 1H), 7.69 (dd, J=2.7, 8.7 Hz, 1H), 7.42 (d, J=8.7 Hz, 1H), 7.30–7.14 (m, 5H), 7.11 (d, J=8.4 Hz, 2H), 6.79 (d, J=8.4 Hz, 2H), 3.87 (t, J=6.6 Hz, 2H), 2.82 (t, J=6.9 Hz, 2H), 2.60–2.45 (m, 4H), 1.70–1.50 (m, 4H), 1.50–1.20 (m, 4H).

EXAMPLE 10(6)

2-chloro-5-[3-(4-(5-phenylpentyloxy)phenyl)-(2E)-propenoylamino]benzoic acid

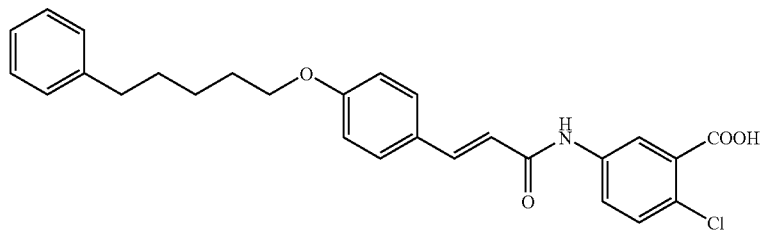

TLC: Rf 0.49 (chloroform:methanol:acetic acid=90:10:1); NMR (DMSO-d$_6$): δ 13.52–13.21 (br, 1H), 10.37 (s, 1H), 8.15 (d, J=2.7 Hz, 1H), 7.82 (dd, J=8.7, 2.7 Hz, 1H), 7.56–7.46 (m, 4H), 7.28–7.12 (m, 5H), 6.96 (d, J=8.7 Hz, 2H), 6.61 (d, J=15.9 Hz, 1H), 3.99 (t, J=6.6 Hz, 2H), 2.58 (t, J=7.5 Hz, 2H) 1.78–1.56 (m, 4H), 1.45–1.33 (m, 2H).

EXAMPLE 11

2-amino-5-[3-(4-(5-phenylpentyloxy)phenyl)propanoylamino]benzoic acid

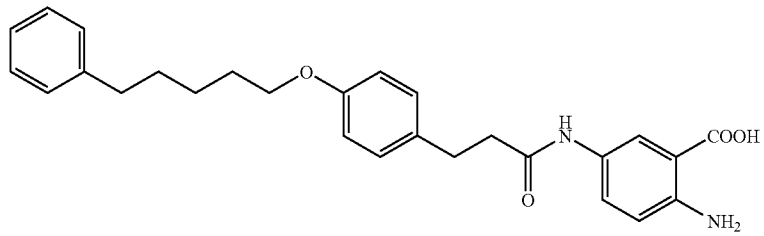

To a solution of the compound prepared in Example 4(6) (306 mg) in methanol (5 mL) was added 5% palladium on carbon (63 mg). The reaction mixture was stirred for 8 hours under an atmosphere of hydrogen. Tetrahydrofuran was added to the reaction mixture, which was filtered through CELITE (brand name) and the filtrate was concentrated. The residue was recrystallized from methanol-water (5:1), filtered and dried to give the compound of the present invention (208 mg) having the following physical data.

TLC: Rf 0.30 (chloroform:methanol=9:1); NMR (DMSO-d$_6$): δ 9.55 (s, 1H), 8.80–8.10 (br, 2H), 7.88 (d, J=2.7 Hz, 1H), 7.40 (dd, J=9.0, 2.7 Hz, 1H), 7.27–7.09 (m, 7H), 6.79 (d, J=8.7 Hz, 2H), 6.65 (d, J=9.0 Hz, 1H), 3.88 (t, J=6.6 Hz, 2H), 2.79 (t, J=7.5 Hz, 2H), 2.56 (t, J=7.5 Hz, 2H), 2.49–2.44 (m, 2H), 1.74–1.54 (m, 4H), 1.44–1.34 (m, 2H).

EXAMPLE 11(1)

2-amino-5-[3-(3-methoxy-4-(5-phenylpentyloxy)phenyl)propanoylamino]benzoic acid

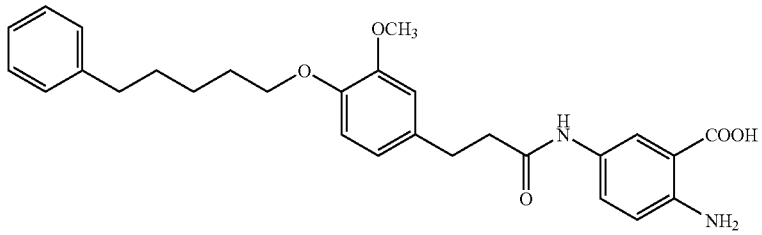

By the same procedure as described in Example 11 using the compound prepared in Example 9(8) instead of the compound prepared in Example 4(6), the compound of the present invention having the following physical data were obtained.

TLC: Rf 0.59 (chloroform:methanol=4:1); NMR (DMSO-$d_6$): δ 9.57 (s, 1H), 8.45 (brs, 2H), 7.90 (d, J=2.7 Hz, 1H), 7.42 (dd, J=2.7, 8.7 Hz, 1H), 7.30–7.12 (m, 5H), 6.85–6.80 (m, 2H), 6.75–6.65 (m, 2H), 3.88 (t, J=6.3 Hz, 2H), 3.71 (s, 3H), 2.81 (t, J=7.8 Hz, 2H), 2.59 (t, J=7.8 Hz, 2H), 2.52–2.45 (m, 2H), 1.80–1.60 (m, 4H), 1.50–1.40 (m, 2H).

EXAMPLE 12 methyl 2-chloro-5-[N-methyl-3-(4-(5-phenylpentyloxy)phenyl)propanoylamino]benzoate

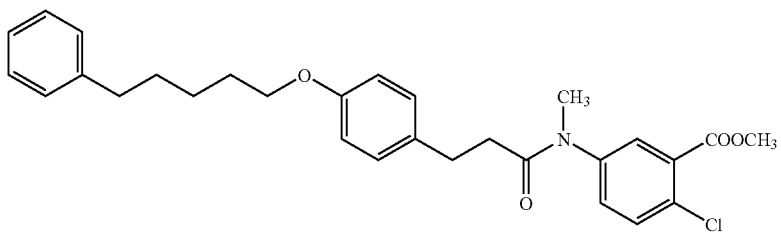

To a solution of the compound prepared in Example 1(1) (209 mg) in dimethylformamide (2 mL) was added 63% sodium hydride (20 mg) at 0° C. The reaction mixture was stirred at 0° C. for 30 minutes. To the reaction mixture was added methyl iodide (32 μL). The reaction mixture was stirred at room temperature for 30 minutes. Saturated aqueous solution of ammonium chloride was added to the reaction mixture, which was extracted with ethyl acetate. The extract was washed with brine, dried over anhydrous sodium sulfate and concentrated. The obtained residue was purified by column chromatography on silica gel (hexane:ethyl acetate=2:1) to give the compound of the present invention (140 mg) having the following physical data.

TLC: Rf 0.31 (hexane:ethyl acetate=1:1).

EXAMPLE 13

2-chloro-5-[N-methyl-3-(4-(5-phenylpentyloxy)phenyl)propanoylamino]benzoic acid

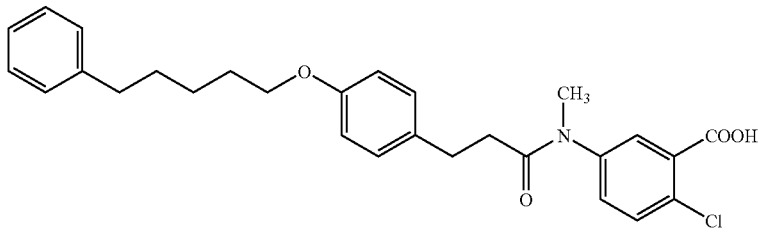

By the same procedure as described in Example 2 using the compound prepared in Example 12 instead of the compounds prepared in Example 1, the compound of the present invention having the following physical data were obtained.

TLC: Rf 0.44 (chloroform:methanol=17:3); NMR (DMSO-$d_6$): δ 13.50 (s, 1H), 7.62 (d, J=2.7 Hz, 1H), 7.56 (d, J=8.4 Hz, 1H), 7.39 (dd, J=2.7, 8.4 Hz, 1H), 7.30–7.12 (m, 5H), 6.98 (brs, 2H), 6.76 (d, J=8.4 Hz, 2H), 3.89 (t, J=6.3 Hz, 2H), 3.16 (s, 3H), 2.76–2.65 (m, 2H), 2.59 (t, J=7.5 Hz, 2H), 2.50–2.20 (m, 2H), 1.80–1.54 (m, 4H), 1.48–1.35 (m, 2H).

EXAMPLE 14

2-chloro-5-[3-(4-(5-phenylpentyloxy)phenyl)propanoylamino]benzamide

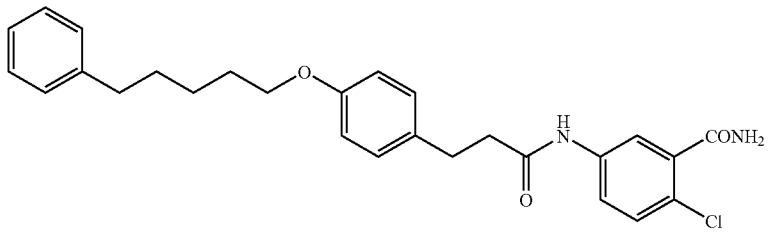

By the same procedure as described in Example 7 using 5-amino-2-chlorobenzamide instead of methyl 2-chloro-5-aminobenzoate and the compound prepared in Reference Example 2 instead of 3-[2-methoxy-4-(5-phenylpentyloxy)phenyl]propanoic acid, the compound of the present invention having the following physical data were obtained.

TLC: Rf 0.58 (chloroform:methanol=9:1); NMR (DMSO-$d_6$): δ 7.83 (s, 1H), 7.67 (d, J=3.0 Hz, 1H), 7.61–7.55 (m, 2H), 7.35 (d, J=8.7 Hz, 1H), 7.27–7.09 (m, 8H), 6.82–6.77 (m, 2H), 3.88 (t, J=6.6 Hz, 2H), 2.81 (t, J=7.5 Hz, 2H) 2.56 (t, J=7.5 Hz, 4H), 1.74–1.55 (m, 4H), 1.44–1.34 (m, 2H).

EXAMPLE 14(1) and 14(2)

By the same procedure as described in Example 14 using the corresponding amine derivatives respectively instead of 5-amino-2-chlorobenzamide, the following compounds of the present invention were obtained.

EXAMPLE 14(1)

3-[3-(4-(5-phenylpentyloxy)phenyl)propanoylamino]benzamide

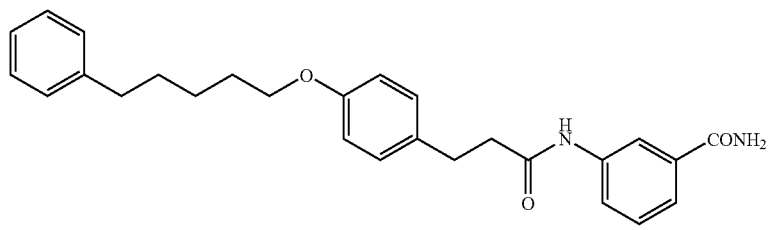

TLC: Rf 0.44 (chloroform:methanol=9:1); NMR (DMSO-$d_6$): δ 10.03 (s, 1H), 8.00 (s, 1H), 7.94–7.84 (br, 1H), 7.74 (d, J=8.8 Hz, 1H), 7.49 (d, J=7.6 Hz, 1H), 7.36–7.10 (m, 9H), 6.79 (d, J=8.6 Hz, 2H), 3.88 (t, J=6.4 Hz, 2H), 2.82 (t, J=7.6 Hz, 2H), 2.56 (t, J=7.6 Hz, 4H), 1.76–1.30 (m, 6H).

EXAMPLE 14(2)

2-fluoro-5-[3-(4-(5-phenylpentyloxy)phenyl)propanoylamino]benzamide

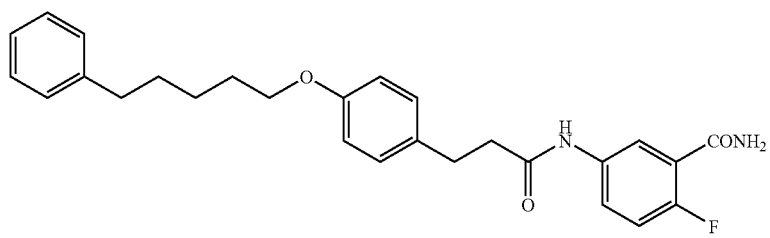

TLC: Rf 0.52 (chloroform:methanol=9:1); NMR (DMSO-$d_6$): δ 10.02 (s, 1H), 7.84 (dd, J=6.6, 2.7 Hz, 1H), 7.71–7.66 (m, 1H), 7.62 (bs, 2H), 7.27–7.10 (m, 8H), 6.82–6.77 (m, 2H), 3.88 (t, J=6.6 Hz, 2H), 2.81 (t, J=7.5 Hz, 2H) 2.59–2.52 (m, 4H), 1.74–1.54 (m, 4H), 1.44–1.34 (m, 2H).

EXAMPLE 15 methyl 2-chloro-5-[2-(4-(5-phenylpentyloxy)phenyl)ethylaminocarbonyl]benzoate

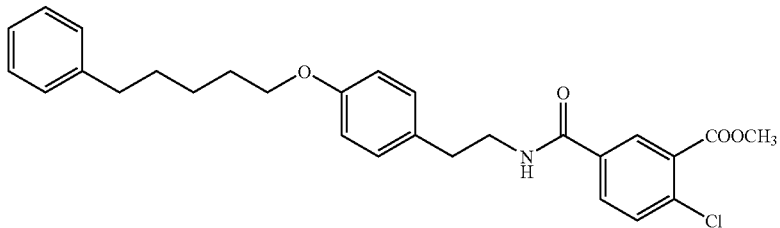

By the same procedure as described in Example 7 using 2-[4-(5-phenylpentyloxy)phenyl]ethylamine instead of methyl 2-chloro-5-aminobenzoate and 4-chloro-3-methoxycarbonylbenzoic acid instead of 3-[2-methoxy-4-(5-phenylpentyloxy)phenyl]propanoic acid, the compound of the present invention having the following physical data were obtained.

TLC: Rf 0.31 (hexane:ethyl acetate=2:1); NMR (CDCl$_3$): δ 8.13 (d, J=2.2 Hz, 1H), 7.78 (dd, J=8.4, 2.2 Hz, 1H), 7.50 (d, J=8.4 Hz, 1H), 7.33–7.09 (m, 7H), 6.88–6.81 (m, 2H), 6.21–6.08 (br, 1H), 3.96–3.90 (m, 5H), 3.72–3.62 (m, 2H), 2.87 (t, J=6.8 Hz, 2H), 2.64 (t, J=7.2 Hz, 2H), 1.88–1.42 (m, 6H).

EXAMPLE 15(1)–15(5)

By the same procedure as described in Example 15 using the corresponding carboxylic acid derivatives respectively instead of 4-chloro-3-methoxycarbonylbenzoic acid, the following compounds of the present invention were obtained.

EXAMPLE 15(1)

methyl 3-[2-(4-(5-phenylpentyloxy)phenyl)ethylaminocarbonyl]benzoate

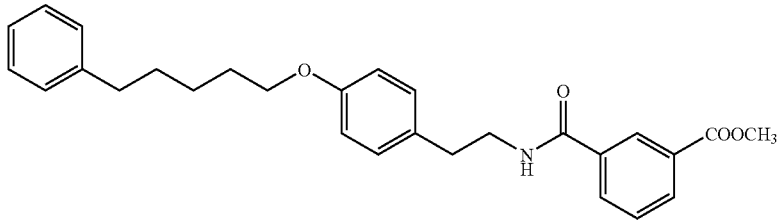

TLC: Rf 0.61 (hexane:ethyl acetate=1:1).

EXAMPLE 15(2)
methyl 2-fluoro-5-[2-(4-(5-phenylpentyloxy)phenyl)ethylaminocarbonyl]benzoate
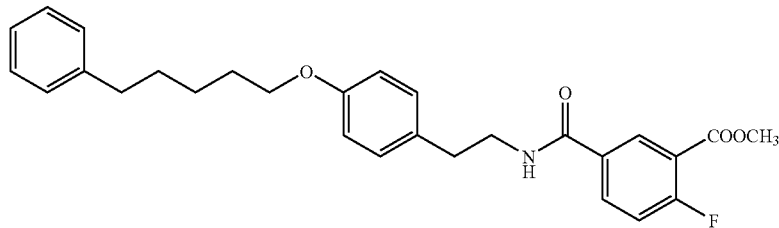
TLC: Rf 0.27 (hexane:ethyl acetate=2:1); NMR (CDCl$_3$): δ 8.23 (dd, J=6.8, 2.4 Hz, 1H), 7.99–7.91 (m, 1H), 7.32–7.10 (m, 8H), 6.85 (d, J=8.6 Hz, 2H), 6.24–6.08 (br, 1H), 3.97–3.90 (m, 5H), 3.73–3.63 (m, 2H), 2.87 (t, J=7.0 Hz, 2H), 2.64 (t, J=7.6 Hz, 2H), 1.88–1.42 (m, 6H).
EXAMPLE 15(3)
methyl 5-[2-(4-(5-phenylpentyloxy)phenyl)ethylaminocarbonyl]pyridine-3-carboxylate
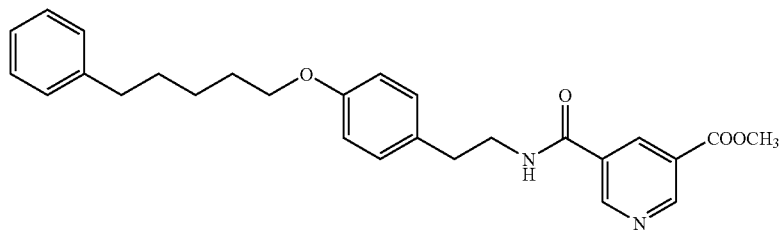
TLC: Rf 0.24 (hexane:ethyl acetate=1:1); NMR (CDCl$_3$): δ 9.29 (d, J=2.2 Hz, 1H), 9.07 (d, J=2.2 Hz, 1H), 8.58 (t, J=2.2 Hz, 1H), 7.32–7.10 (m, 7H), 6.88–6.81 (m, 2H), 6.32–6.16 (br, 1H), 3.97–3.90 (m, 5H), 3.76–3.67 (m, 2H), 2.89 (t, J=7.0 Hz, 2H), 2.64 (t, J=7.4 Hz, 2H), 1.88–1.46 (m, 6H).

EXAMPLE 15(4)

methyl 2-nitro-5-[2-(4-(5-phenylpentyloxy)phenyl)
ethylaminocarbonyl]benzoate

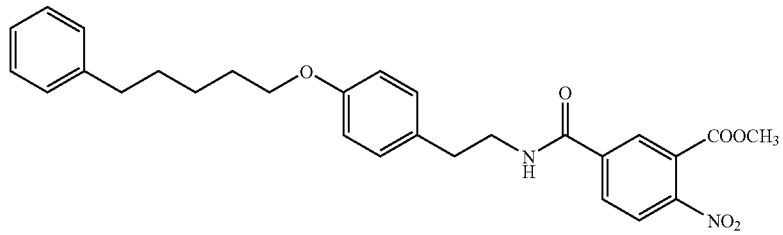

TLC: Rf 0.33 (hexane:ethyl acetate=2:1); NMR (CDCl$_3$):
δ 8.03–7.89 (m, 3H), 7.31–7.10 (m, 7H), 6.88–6.83 (m, 2H),
6.23–6.14 (br, 1H), 3.96–3.91 (m, 5H), 3.73–3.67 (m, 2H),
2.88 (t, J=6.9 Hz, 2H), 2.64 (t, J=7.8 Hz, 2H), 1.86–1.65 (m,
4H), 1.56–1.45 (m, 2H).

EXAMPLE 15(5)

ethyl 3-ethoxycarbonyl-5-[2-(4-(5-phenylpentyloxy)
phenyl)ethylaminocarbonyl]benzoate

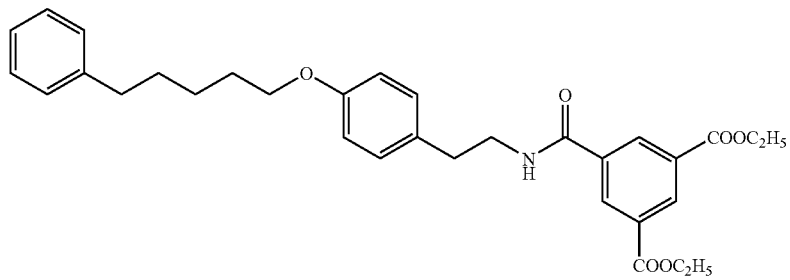

TLC: Rf 0.50 (hexane:ethyl acetate=2:1); NMR (CDCl$_3$):
δ 8.78 (t, J=1.8 Hz, 1H), 8.54 (d, J=1.8 Hz, 2H), 7.30–7.15
(m, 5H), 7.14 (d, J=8.4 Hz, 2H), 6.8 (d, J=8.4 Hz, 2H),
6.35–6.30 (m, 1H), 4.42 (q, J=7.2 Hz, 4H), 3.94 (t, J=6.3 Hz,
2H), 3.70 (q, J=6.3 Hz, 2H), 2.90 (t, J=6.9 Hz, 2H), 2.64 (t,
J=7.5 Hz, 2H), 1.85–1.45 (m, 6H), 1.42 (t, J=7.2 Hz, 6H).

EXAMPLE 16

2-chloro-5-[2-(4-(5-phenylpentyloxy)phenyl)ethylaminocarbonyl]benzoic acid

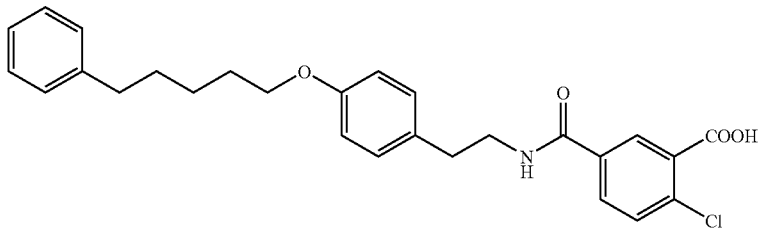

By the same procedure as described in Example 2 using the compound prepared in Example 15 instead of the compound prepared in Example 1, the compound of the present invention having the following physical data were obtained.

TLC: Rf 0.52 (chloroform:methanol:acetic acid=90:10:1); NMR (DMSO-$d_6$): δ 8.73 (t, J=4.8 Hz, 1H), 8.22 (d, J=2.2 Hz, 1H), 7.92 (dd, J=8.4, 2.2 Hz, 1H), 7.63 (d, J=8.4 Hz, 1H), 7.28–7.08 (m, 7H), 6.80 (d, J=8.6 Hz, 2H), 3.88 (t, J=6.4 Hz, 2H), 3.47–3.67 (m, 2H), 2.74 (t, J=7.2 Hz, 2H), 2.56 (t, J=7.6 Hz, 2H), 1.76–1.32 (m, 6H).

EXAMPLE 16(1)–16(5)

By the same procedure as described in Example 16 using the compounds prepared in Example 15(1)–15(5) respectively instead of the compound prepared in Example 15, the following compounds of the present invention were obtained.

EXAMPLE 16(1)

3-[2-(4-(5-phenylpentyloxy)phenyl)ethylaminocarbonyl]benzoic acid

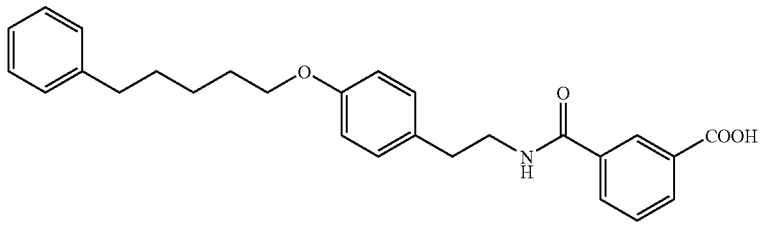

TLC: Rf 0.33 (chloroform:methanol=9:1); NMR (DMSO-$d_6$): δ 8.80–8.70 (m, 1H), 8.44–8.39 (m, 1H), 8.50 (dt, J=7.6, 1.8 Hz, 2H), 7.59 (t, J=7.8 Hz, 1H), 7.32–7.10 (m, 5H), 7.13 (d, J=8.0 Hz, 2H), 6.83 (d, J=8.0 Hz, 2H), 3.91 (t, J=6.4 Hz, 2H), 3.60–3.40 (m, 2H), 2.90–2.70 (m, 2H), 2.59 (t, J=7.5 Hz, 2H), 2.80–1.40 (m, 6H).

EXAMPLE 16(2)

2-fluoro-5-[2-(4-(5-phenylpentyloxy)phenyl)ethylaminocarbonyl]benzoic acid

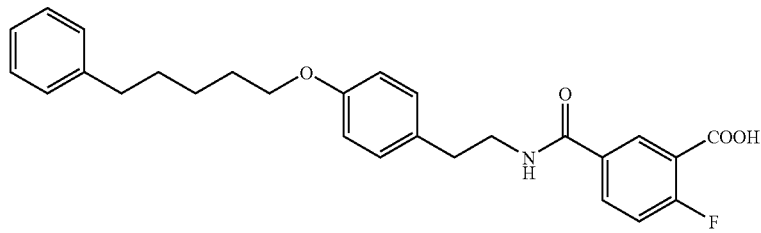

TLC: Rf 0.48 (chloroform:methanol:acetic acid=90:10:1); NMR (DMSO-d$_6$): δ 8.71 (t, J=5.4 Hz, 1H), 8.34 (dd, J=7.2, 2.2 Hz, 1H), 8.08–8.01 (m, 1H), 7.38 (dd, J=10.4, 8.6 Hz, 1H), 7.28–7.08 (m, 7H), 6.80 (d, J=8.4 Hz, 2H), 3.88 (t, J=6.4 Hz, 2H), 3.46–3.37 (m, 2H), 2.74 (t, J=7.4 Hz, 2H), 2.57 (t, J=7.4 Hz, 2H), 1.76–1.32 (m, 6H).

EXAMPLE 16(3)

5-[2-(4-(5-phenylpentyloxy)phenyl)ethylaminocarbonyl]pyridine-3-carboxylic acid

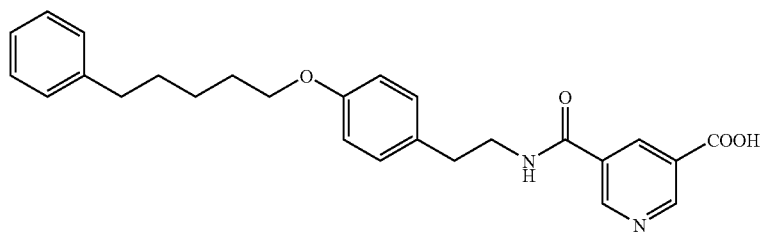

TLC: Rf 0.38 (chloroform:methanol:acetic acid=90:10:1); NMR (DMSO-d$_6$): δ 9.14–9.13 (m, 2H), 8.95–8.84 (br, 1H), 8.62 (t, J=2.0 Hz, 1H), 7.28–7.10 (m, 7H), 6.81 (d, J=8.6 Hz, 2H), 3.89 (t, J=6.4 Hz, 2H), 3.50–3.41 (m, 2H), 2.77 (t, J=7.4 Hz, 2H), 2.57 (t, J=7.4 Hz, 2H), 1.77–1.32 (m, 6H).

EXAMPLE 16(4)

2-nitro-5-[2-(4-(5-phenylpentyloxy)phenyl)ethylaminocarbonyl]benzoic acid

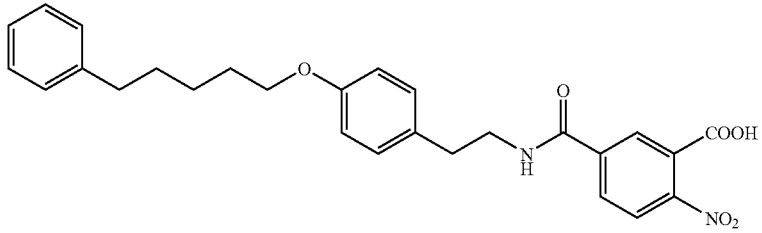

TLC: Rf 0.22 (chloroform:methanol:acetic acid=90:10:1); NMR (DMSO-$d_6$): δ 8.91 (t, J=5.4 Hz, 1H), 8.24 (d, J=1.8 Hz, 1H), 8.14 (dd, J=8.4, 1.8 Hz, 1H), 8.04 (d, J=8.4 Hz, 1H), 7.27–7.09 (m, 7H), 6.83–6.78 (m, 2H), 3.88 (t, J=6.6 Hz, 2H), 3.48–3.41 (m, 2H), 2.76 (t, J=7.5 Hz, 2H), 2.57 (t, J=7.5 Hz, 2H), 1.74–1.55 (m, 4H), 1.44–1.34 (m, 2H).

EXAMPLE 16(5)

3-carboxy-5-[2-(4-(5-phenylpentyloxy)phenyl)ethylaminocarbonyl]benzoic acid

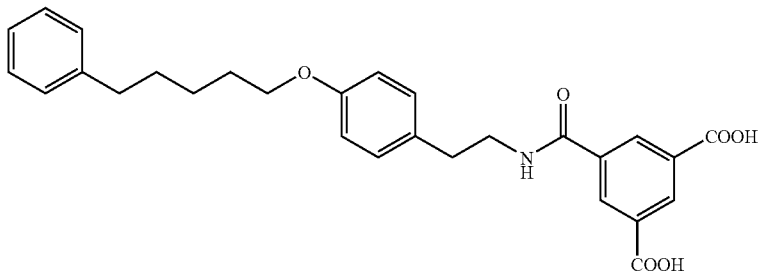

TLC: Rf 0.79 (chloroform:methanol:acetic acid=8:2:1); NMR (DMSO-$d_6$): δ 13.45 (s, 2H), 8.94 (t, J=5.4 Hz, 1H), 8.62 (d, J=1.5 Hz, 2H), 8.57 (t, J=1.5 Hz, 1H), 7.30–7.15 (m, 5H), 7.13 (d, J=8.7 Hz, 2H), 6.83 (d, J=8.7 Hz, 2H), 3.91 (t, J=6.3 Hz, 2H), 3.50–3.40 (m, 2H), 2.79 (t, J=7.8 Hz, 2H), 2.59 (t, J=7.8 Hz, 2H), 1.80–1.55 (m, 4H), 1.50–1.35 (m, 2H).

EXAMPLE 17

6-[2-(4-(5-phenylpentyloxy)phenyl)ethylaminocarbonyl]pyridine-2-carboxylic acid

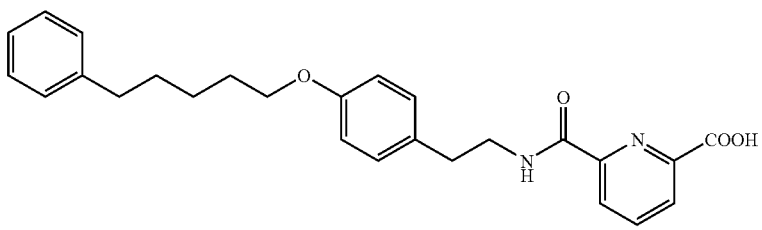

By the same procedure as described in Example 15→Example 16 using the corresponding carboxylic acid derivative instead of 4-chloro-3-methoxycarbonylbenzoic acid, the compound of the present invention having the following physical data were obtained.

TLC: Rf 0.30 (chloroform:methanol:acetic acid=90:10:1); NMR (DMSO-$d_6$): δ 13.22–12.92 (br, 1H), 9.23 (t, J=6.0 Hz, 1H), 8.27–8.14 (m, 3H), 7.28–7.11 (m, 7H), 6.81 (d, J=8.4 Hz, 2H), 3.89 (t, J=6.4 Hz, 2H), 3.56–3.46 (m, 2H), 2.79 (t, J=7.2 Hz, 2H), 2.57 (t, J=7.2 Hz, 2H), 1.77–1.31 (m, 6H).

EXAMPLE 17(1) and 17(2)

By the same procedure as described in Example 17 using the corresponding carboxylic acid derivatives respectively instead of 6-ethoxycarbonylpyridine-2-carboxylic acid, the following compounds of the present invention were obtained.

EXAMPLE 17(1)

4-chloro-3-[2-(4-(5-phenylpentyloxy)phenyl)ethylaminocarbonyl]benzoic acid

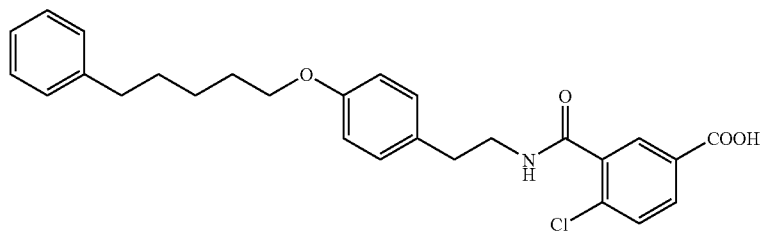

TLC: Rf 0.17 (chloroform:methanol=9:1); NMR (DMSO-d$_6$): δ 8.57 (t, J=5.1 Hz, 1H), 7.92 (dd, J=8.4, 2.1 Hz, 1H), 7.82 (d, J=2.1 Hz, 1H), 7.59 (d, J=8.4 Hz, 1H), 7.27–7.12 (m, 7H), 6.82 (d, J=8.7 Hz, 2H), 3.90 (t, J=6.6 Hz, 2H), 3.44–3.37 (m, 2H), 2.74 (t, J=7.5 Hz, 2H), 2.57 (t, J=7.5 Hz, 2H), 1.75–1.55 (m, 4H), 1.45–1.35 (m, 2H).

EXAMPLE 17(2)

4-[2-(4-(5-phenylpentyloxy)phenyl)ethylaminocarbonyl]pyridine-2-carboxylic acid

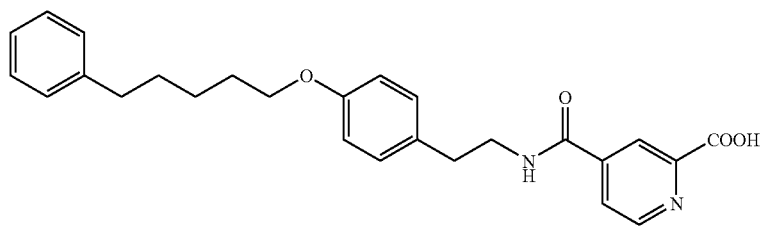

TLC: Rf 0.38 (chloroform:methanol:acetic acid=9:1:1); NMR (DMSO-d$_6$): δ 8.99 (t, J=5.4 Hz, 1H), 8.81 (d, J=4.8 Hz, 1H), 8.38 (s, 1H), 7.92 (dd, J=4.8, 1.8 Hz, 1H), 7.27–7.10 (m, 7H), 6.81 (d, J=8.4 Hz, 2H), 3.88 (t, J=6.6 Hz, 2H), 3.48–3.41 (m, 2H) 2.76 (t, J=7.8 Hz, 2H), 2.56 (t, J=7.8 Hz, 2H), 1.74–1.54 (m, 4H), 1.44–1.34 (m, 2H).

EXAMPLE 18

N-[2-(4-(5-phenylpentyloxy)phenyl)ethyl]-1-(1,3-dioxobenzofuran-5-yl)carboxamide

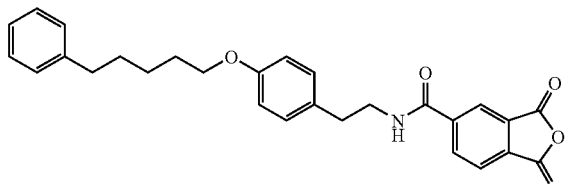

By the same procedure as described in Example 1 using trimellitic anhydride chloride instead of the compound prepared in Reference Example 3 and 4-(5-phenylpentyloxy)phenyl)ethylamine instead of methyl 2-methoxy-5-aminobenzoate, the compound of the present invention were obtained. The obtained compound was used next reaction without purification.

EXAMPLE 19

2-carboxy-5-[2-(4-(5-phenylpentyloxy)phenyl)ethylaminocarbonyl]benzoic acid

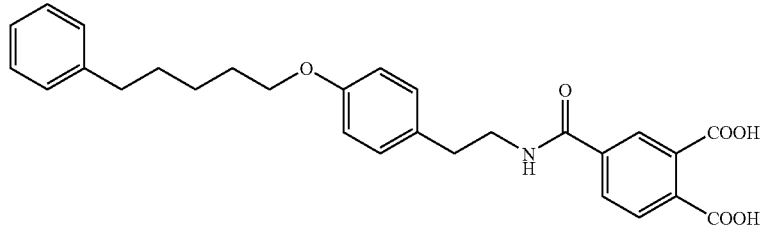

By the same procedure as described in Example 2 using the compound prepared in Example 18 instead of the compound prepared in Example 1, the compound of the present invention having the following physical data were obtained.

TLC: Rf 0.30 (chloroform:methanol:acetic acid=9:1:1); NMR (DMSO-$d_6$): δ 8.77 (t, J=6.0 Hz, 1H), 8.11 (d, J=1.8 Hz, 1H), 7.98 (dd, J=8.1, 1.8 Hz, 1H), 7.71 (d, J=8.1 Hz, 1H), 7.27–7.09 (m, 7H), 6.83–6.78 (m, 2H), 3.88 (t, J=6.6 Hz, 2H), 3.46–3.39 (m, 2H), 2.75 (t, J=7.5 Hz, 2H), 2.57 (t, J=7.5 Hz, 2H), 1.74–1.55 (m, 4H), 1.44–1.34 (m, 2H).

EXAMPLE 20

2-amino-5-[2-(4-(5-phenylpentyloxy)phenyl)ethylaminocarbonyl]benzoic acid

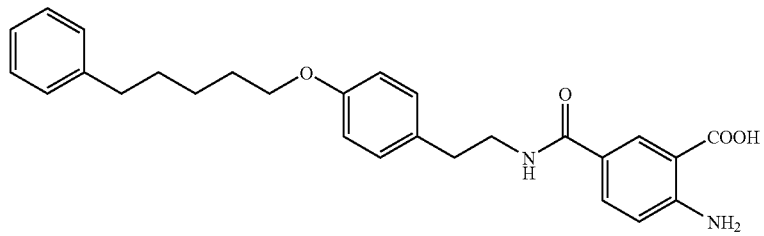

By the same procedure as described in Example 11 using the compound prepared in Example 16(4) instead of the compound prepared in Example 4(6), the compound of the present invention having the following physical data were obtained.

TLC: Rf 0.48 (chloroform:methanol=9:1); NMR (DMSO-$d_6$): δ 8.26–8.22 (m, 2H), 7.69 (dd, J=8.7, 2.1 Hz, 1H), 7.27–7.08 (m, 7H), 6.80 (d, J=8.4 Hz, 2H), 6.72 (d, J=8.7 Hz, 1H), 3.88 (t, J=6.6 Hz, 2H), 3.39–3.32 (m, 2H), 2.71 (t, J=7.5 Hz, 2H), 2.57 (t, J=7.5 Hz, 2H), 1.74–1.55 (m, 4H), 1.44–1.34 (m, 2H).

EXAMPLE 21 methyl 2-methoxycarbonyl-5-[3-(4-(5-phenylpenty-loxy)phenyl)propylamino]benzoate

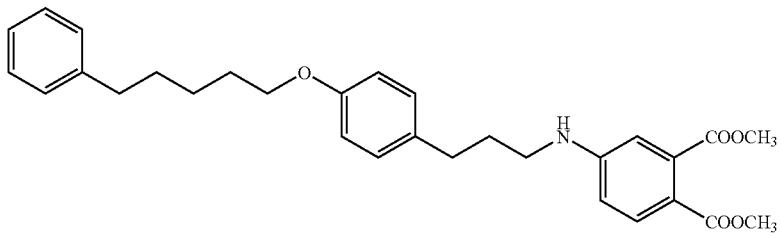

To a solution of 3-(4-(5-phenylpentyloxy)phenyl)propanal (144 mg) in methanol (5 mL) was added methyl 2-methoxycarbonyl-4-aminobenzoate (331 mg), a solution of sodium cyanoborohydride (29 mg) in methanol (2 mL), and acetic acid (35 µL) sequentially. The reaction mixture was stirred at room temperature for 2 hours. Saturated aqueous solution of sodium hydrogen carbonate was added to the reaction mixture, which was extracted with ethyl acetate. The extract was washed with brine, dried over anhydrous magnesium sulfate and concentrated. The obtained residue was purified by column chromatography on silica gel (hexane:ethyl acetate=3:1) to give the compound of the present invention (200 mg) having the following physical data.

TLC: Rf 0.27 (hexane:ethyl acetate=3:1); NMR (CDCl$_3$): δ 7.73 (d, J=8.4 Hz, 1H), 7.30–7.06 (m, 7H), 6.84–6.81 (m, 2H), 6.55–6.50 (m, 2H), 4.14 (t, J=5.4 Hz, 1H), 3.93 (t, J=6.6 Hz, 2H), 3.90 (s, 3H), 3.83 (s, 3H), 3.20–3.13 (m, 2H), 2.68–2.62 (m, 4H), 1.96–1.64 (m, 6H), 1.54–1.45 (m, 2H).

EXAMPLE 22

2-carboxy-5-[3-(4-(5-phenylpentyloxy)phenyl)propylamino]benzoic acid

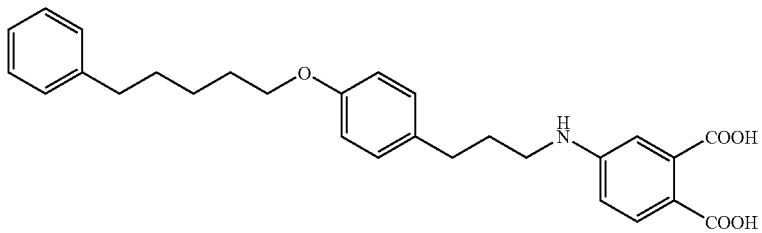

By the same procedure as described in Example 2 using the compound prepared in Example 21 instead of the compound prepared in Example 1, the compound of the present invention having the following physical data were obtained.

TLC: Rf 0.45 (chloroform:methanol:acetic acid=9:1:1); NMR (DMSO-d$_6$): δ 12.70–12.10 (br, 2H), 7.57 (d, J=8.7 Hz, 1H), 7.28–7.06 (m, 7H), 6.82–6.78 (m, 2H), 6.55–6.52 (m, 3H), 3.89 (t, J=6.6 Hz, 2H), 3.06–2.98 (br, 2H), 2.57 (t, J=7.5 Hz, 4H), 1.82–1.55 (m, 6H), 1.45–1.34 (m, 2H).

EXAMPLE 22(1)

2-chloro-5-[3-(4-(5-phenylpentyloxy)phenyl)propy-lamino]benzoic acid

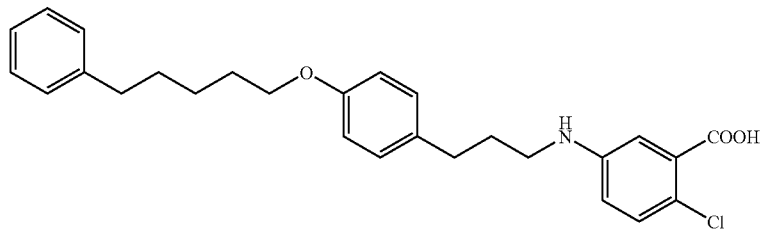

By the same procedure as described in Example 21→Example 22 using methyl 2-chloro-5-aminobenzoate instead of methyl 2-methoxycarbonyl-4-aminobenzoate, the compound of the present invention having the following physical data were obtained.

TLC: Rf 0.26 (chloroform:methanol=9:1); NMR (DMSO-$d_6$): δ 7.27–7.04 (m, 8H), 6.83–6.78 (m, 3H), 6.53 (dd, J=8.7, 3.0 Hz, 1H), 6.00–5.75 (br, 1H), 3.88 (t, J=6.6 Hz, 2H), 2.93 (t, J=7.2 Hz, 2H), 2.57 (t, J=7.5 Hz, 4H), 1.81–1.55 (m, 6H), 1.44–1.34 (m, 2H).

EXAMPLE 23

3-[2-(4-(5-phenylpentyloxy)phenyl)ethylaminosulfo-nyl]benzoic acid

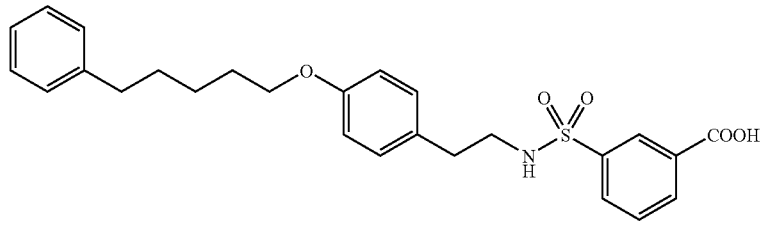

To a solution of 2-(4-(5-phenylpentyloxy)phenyl)ethy-lamine (300 mg) in dichloromethane (5 mL) was added 3-(chlorosulfonyl)benzoic acid (331 mg) and triethylamine (0.7 mL). The reaction mixture was stirred at room temperature for 5 hours. 1N aqueous hydrochloric acid solution was added to the reaction mixture, which was extracted with ethyl acetate. The extract was washed with brine, dried over anhydrous magnesium sulfate and concentrated. The obtained residue was purified by column chromatography on silica gel (chloroform:methanol=20:1) to give the compound of the present invention (186 mg) having the following physical data.

TLC: Rf 0.51 (chloroform:methanol=9:1); NMR (DMSO-$d_6$): δ 13.45 (s, 1H), 8.30 (t, J=1.8 Hz, 1H), 8.17–8.13 (m, 1H), 8.00–7.95 (m, 1H), 7.83 (t, J=5.7 Hz, 1H), 7.70 (t, J=7.8 Hz, 1H), 7.30–7.12 (m, 5H), 7.02 (d, J=8.4 Hz, 2H), 6.76 (d, J=8.4 Hz, 2H), 3.89 (t, J=6.3 Hz, 2H), 3.00–2.90 (m, 2H), 2.59 (t, J=7.5 Hz, 4H), 1.80–1.75 (m, 4H), 1.70–1.35 (m, 2H).

EXAMPLE 24 methyl 2-[2-(4-(5-phenylpentyloxy)phenyl)ethyl]benzoimidazol-5-carboxylate

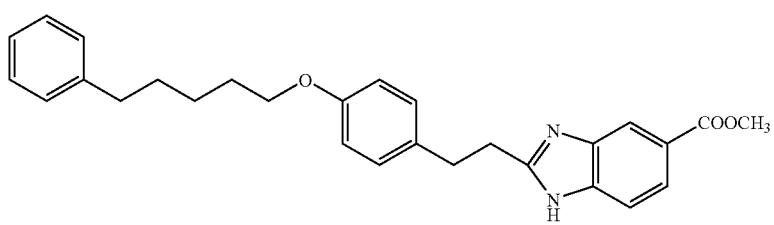

To a solution of the compound prepared in Reference Example 3 which prepared by the same procedure as described in Example 3 using the compound prepared in Reference Example 2 (150 mg) in dichloromethane (5 mL) was added methyl 3,4-diaminobenzoate (160 mg) and triethylamine (0.34 mL). The reaction mixture was stirred at room temperature for 1 hour. The reaction mixture was concentrated. To a solution of the obtained residue in toluene (10 mL) was added p-toluenesulfonate (50 mg). The reaction mixture was refluxed overnight. Saturated aqueous solution of sodium hydrogen carbonate was added to the reaction mixture, which was extracted with ethyl acetate. The extract was washed with brine, dried over anhydrous sodium sulfate and concentrated. The obtained residue was washed with diisopropyl ether to give the compound of the present invention (99 mg) having the following physical data.

NMR (CDCl$_3$): δ 8.24 (m, 1H), 7.95 (dd, J=1.6, 8.6 Hz, 1H), 7.53 (d, J=8.6 Hz, 1H), 7.30–7.15 (m, 5H), 7.09 (d, J=8.6 Hz, 2H), 6.80 (d, J=8.6 Hz, 2H), 3.93 (s, 3H), 3.92 (t, J=6.6 Hz, 2H), 3.30–3.10 (m, 4H), 2.65 (t, J=7.6 Hz, 2H), 1.90–1.59 (m, 6H).

EXAMPLE 25

2-[2-(4-(5-phenylpentyloxy)phenyl)ethyl]benzoimidazol-5-carboxylic acid

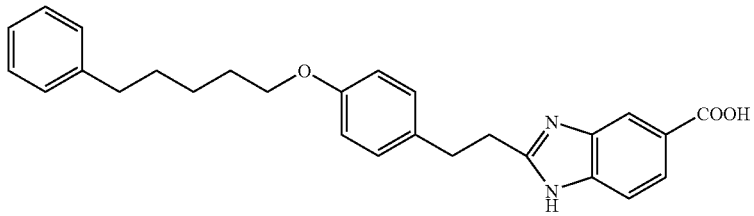

By the same procedure as described in Example 2 using the compound prepared in Example 24 instead of the compound prepared in Example 1, the compound of the present invention having the following physical data were obtained.

TLC: Rf 0.49 (chloroform:methanol=8:1); NMR (DMSO-d$_6$): δ 8.22 (s, 1H), 8.00 (d, J=9.0 Hz, 1H), 7.78 (d, J=9.0 Hz, 1H), 7.30–7.10 (m, 7H), 6.82 (d, J=7.8 Hz, 2H), 3.89 (t, J=6.6 Hz, 2H), 3.35–3.30 (m, 2H), 3.15–3.05 (m, 2H), 2.65–2.55 (m, 2H), 1.80–1.55 (m, 4H), 1.50–1.35 (m, 2H).

EXAMPLE 26

N-[4-chloro-3-(hydroxymethyl)phenyl]-3-[4-(5-phenylpentyloxy)phenyl]propanamide

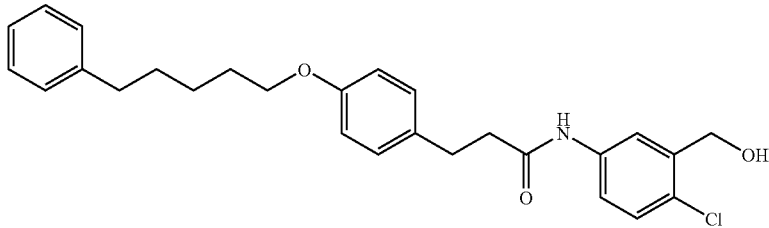

To a solution of the compound prepared in Example 2(1) (245 mg) in tetrahydrofuran (5 mL) was added isobutyl chlorocarbonate (94 mg) and N-methylmorpholine (54 mg) at −20° C. The reaction mixture was stirred at −20 to 30° C. The reaction mixture was concentrated. The obtained residue was purified by column chromatography on silica gel (hexane:ethyl acetate=10:1) to give mixed acid anhydride (250 mg). To a solution of the obtained mixed acid anhydride (250 mg) in dichloromethane (5 mL) was added sodium borohydride (30 mg) and methanol (0.1 mL). The reaction mixture was stirred at room temperature for 1 hour. 1N hydrochloric acid was added to the reaction mixture, which extracted with ethyl acetate. The extract was washed with brine, dried over anhydrous sodium sulfate and concentrated. The obtained residue was washed dichloromethane, isopropylalcohol and hexane to give the compound of the present invention (124 mg) having the following physical data.

TLC: Rf 0.62 (hexane:ethyl acetate=2:1); NMR (DMSO-d$_6$): 10.00 (s, 1H), 7.73 (d, J=2.7 Hz, 1H), 7.59 (dd, J=2.7, 9.0 Hz, 1H), 7.30–7.15 (m, 6H), 7.13 (d, J=8.7 Hz, 2H), 6.80 (d, J=8.7 Hz, 2H), 5.40 (t, J=5.7 Hz, 1H), 4.51 (d, J=5.7 Hz, 2H), 3.89 (t, J=6.6 Hz, 2H), 2.83 (t, J=6.6 Hz, 2H), 2.65–2.50 (m, 4H), 1.80–1.55 (m, 4H), 1.50–1.30 (m, 2H).

EXAMPLE 27 methyl 2-[3-(4-(6-phenylhexyl)phenyl)propanoylamino]acetate

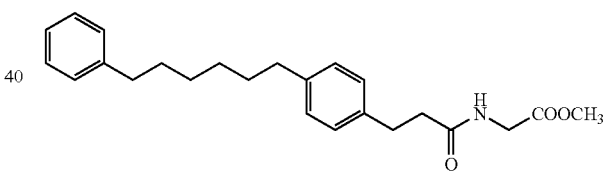

By the same procedure as described in Reference Example 3→Example 1 using 3-[4-(6-phenylhexyl)phenyl]propanoic acid and glycine methyl ester hydrochloride instead of the compound prepared in Reference Example 2, the compound of the present invention having the following physical data were obtained.

TLC: Rf 0.33 (hexane:ethyl acetate=1:1); NMR (CDCl$_3$): δ 7.31–7.05 (m, 9H), 5.95–5.84 (br, 1H), 4.03 (d, J=5.2 Hz, 2H), 3.75 (s, 3H), 2.98–2.90 (m, 2H), 2.63–2.50 (m, 6H), 1.69–1.59 (br, 4H), 1.44–1.26 (m, 4H).

EXAMPLE 28

2-[3-(4-(6-phenylhexyl)phenyl)propanoylamino]acetic acid

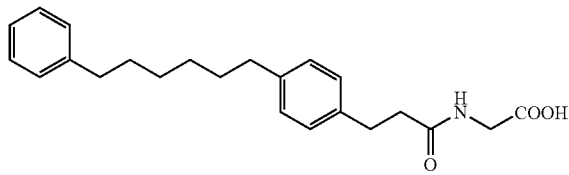

By the same procedure as described in Example 2 using the compound prepared in Example 27 instead of the compound prepared in Example 1, the compound of the present invention having the following physical data were obtained.

TLC: Rf 0.10 (chloroform:methanol=9:1); NMR (CDCl$_3$): δ 7.31–7.05 (m, 9H), 6.17–6.07 (br, 1H), 4.03 (d, J=5.0 Hz, 2H), 2.93 (t, J=7.8 Hz, 2H), 2.62–2.51 (m, 6H), 1.70–1.49 (br, 4H) 1.44–1.26 (m, 4H).

EXAMPLE 28(1)–28(12)

By the same procedure as described in Example 27→Example 28 using the corresponding carboxylic acid derivatives respectively instead of 3-[4-(6-phenylhexyl)phenyl]propanoic acid and the amine derivatives respectively instead of glycine methyl ester hydrochloride, the following compounds of the present invention were obtained.

EXAMPLE 28(1)

3-[3-(4-(6-phenylhexyl)phenyl)propanoylamino]propanoic acid

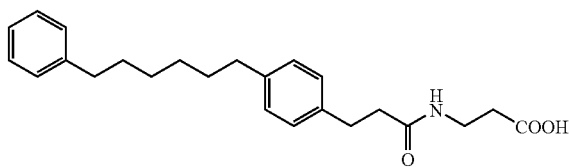

TLC: Rf 0.34 (chloroform:methanol=9:1); NMR (CDCl$_3$): δ 7.31–7.07 (m, 9H), 6.02 (t, J=5.8 Hz, 1H), 3.52–3.43 (m, 2H), 2.91 (t, J=7.8 Hz, 2H), 2.62–2.41 (m, 8H), 1.68–1.51 (m, 4H) 1.38–1.26 (m, 4H).

EXAMPLE 28(2)

2-[3-(4-(5-phenylpentyloxy)phenyl)propanoylamino]acetic acid

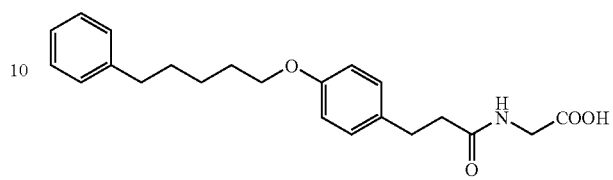

TLC: Rf 0.10 (chloroform:methanol=9:1); NMR (CDCl$_3$): δ 7.32–7.05 (m, 7H), 6.83–6.76 (m, 2H), 6.14 (t, J=5.4 Hz, 1H), 4.02 (d, J=5.4 Hz, 2H), 3.91 (t, J=6.6 Hz, 2H), 2.90 (t, J=7.6 Hz, 2H), 2.67–2.49 (m, 4H), 1.86–1.40 (m, 6H).

EXAMPLE 28(3)

3-[3-(4-(5-phenylpentyloxy)phenyl)propanoylamino]propanoic acid

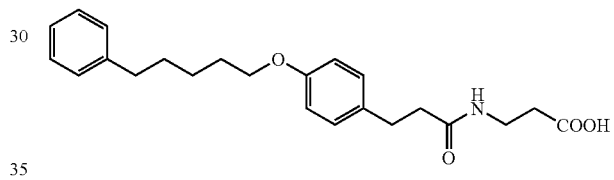

TLC: Rf 0.26 (chloroform:methanol=9:1); NMR (CDCl$_3$): δ 7.32–7.03 (m, 7H), 6.82–6.75 (m, 2H), 6.03 (t, J=5.8 Hz, 1H), 3.91 (t, J=6.6 Hz, 2H), 3.51–3.42 (m, 2H), 2.88 (t, J=7.6 Hz, 2H), 2.64 (t, J=7.6 Hz, 2H), 2.54–2.39 (m, 4H), 1.86–1.40 (m, 6H).

EXAMPLE 28(4)

4-[3-(4-(5-phenylpentyloxy)phenyl)propanoylamino]butanoic acid

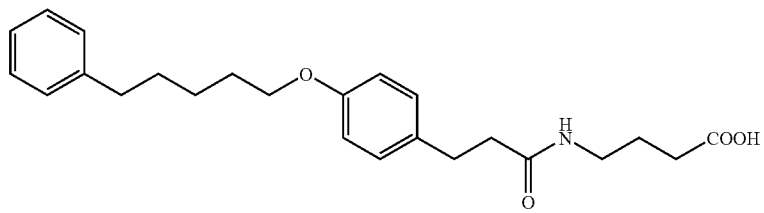

TLC: Rf 0.32 (chloroform:methanol=9:1); NMR (CDCl$_3$): δ 7.32–7.05 (m, 7H), 6.83–6.76 (m, 2H), 5.66 (t, J=5.2 Hz, 1H), 3.91 (t, J=6.6 Hz, 2H), 3.31–3.22 (m, 2H), 2.88 (t, J=7.6 Hz, 2H), 2.64 (t, J=7.6 Hz, 2H), 2.43 (t, J=7.6 Hz, 2H), 2.29 (t, J=7.0 Hz, 2H), 1.86–1.41 (m, 8H).

EXAMPLE 28(5)

4-[3-(4-(6-phenylhexyl)phenyl)propanoylamino]butanoic acid

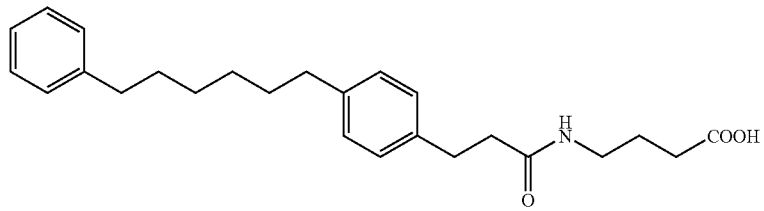

TLC: Rf 0.33 (chloroform:methanol=9:1); NMR (CDCl$_3$): δ 7.30–6.98 (m, 9H), 5.66 (t, J=5.2 Hz, 1H) 3.31–3.22 (m, 2H), 2.91 (t, J=7.6 Hz, 2H), 2.62–2.42 (m, 6H), 2.28 (t, J=7.0 Hz, 2H), 1.81–1.51 (m, 6H), 1.42–1.26 (m, 4H).

EXAMPLE 28(6)

2-[N-methyl-3-(4-(5-phenylpentyloxy)phenyl)propanoylamino]acetic acid

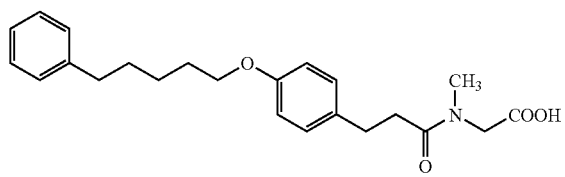

TLC: Rf 0.13 (chloroform:methanol=9:1); NMR (CDCl$_3$): δ 7.31–7.10 (m, 7H), 6.81 (d, J=8.8 Hz, 2H), 4.14–3.89 (m, 4H), 3.02–2.87 (m, 5H), 2.69–2.49 (m, 4H), 1.87–1.42 (m, 6H).

EXAMPLE 28(7)

2-[N-(pyridin-2-yl)methyl-3-(4-(5-phenylpentyloxy)phenyl)propanoylamino]acetic acid hydrochloride

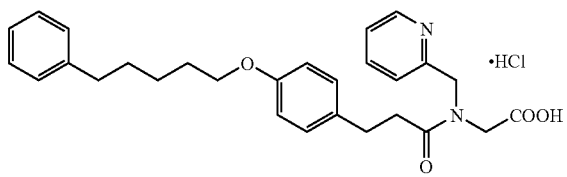

TLC: Rf 0.35 (chloroform:methanol:acetic acid=9:1:1); NMR (DMSO-d$_6$): 68.75–8.64 (m, 1H), 8.41–8.33 and 8.13–8.05 (m, 1H), 7.83–7.77 and 7.61–7.55 (m, 2H), 7.29–7.01 (m, 7H), 6.80–6.72 (m, 2H), 4.87 and 4.80 (m, 2H), 4.35 and 4.02 (m, 2H), 3.91–3.83 (m, 2H), 2.74–2.53 (m, 6H), 1.77–1.23 (m, 6H).

EXAMPLE 28(8)

2-[3-(4-(4-phenylbutoxy)phenyl)-2-propenoylamino]acetic acid

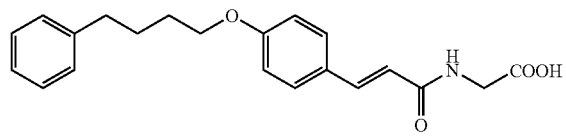

TLC: Rf 0.34 (chloroform:methanol=4:1); NMR (DMSO-d$_6$): δ 8.30 (t, J=5.7 Hz, 1H), 7.50 (d, J=8.8 Hz, 2H), 7.38 (d, J=15.6 Hz, 1H), 7.35–7.14 (m, 5H), 6.96 (d, J=8.8 Hz, 2H), 6.56 (d, J=15.6 Hz, 1H), 4.05–4.00 (m, 2H), 3.87 (d, J=5.7 Hz, 2H), 2.70–2.60 (m, 2H), 1.80–1.60 (m, 4H).

EXAMPLE 28(9)

3-[3-(4-(4-phenylbutoxy)phenyl)-2-propenoylamino]propanoic acid

TLC: Rf 0.37 (chloroform:methanol=9:1); NMR (CDCl$_3$): δ 7.57 (d, J=15.2 Hz, 1H), 7.41 (d, J=8.6 Hz, 2H), 7.35–7.10 (m, 5H), 6.85 (d, J=8.6 Hz, 2H), 6.24 (d, J=15.2 Hz, 1H), 6.35–6.20 (m, 1H), 4.00–3.90 (m, 2H), 3.70–3.60 (m, 2H), 2.80–2.60 (m, 4H), 1.90–1.70 (m, 4H).

EXAMPLE 28(10)

2-[(6-(5-phenylpentyloxy)naphthalen-2-yl)carbonylamino]acetic acid

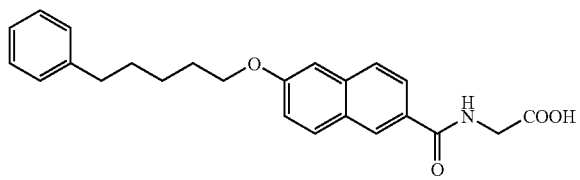

TLC: Rf 0.30 (chloroform:methanol=8:1); NMR (DMSO-d$_6$): δ 12.58 (s, 1H), 8.90 (t, J=5.7 Hz, 1H), 8.40 (s, 1H), 7.92 (d, J=8.7 Hz, 1H), 7.90 (dd, J=1.8, 8.7 Hz, 1H), 7.85 (d, J=8.7 Hz, 1H), 7.36 (d, J=2.4 Hz, 1H), 7.30–7.15 (s, 6H), 4.11 (t, J=6.6 Hz, 2H), 3.96 (d, J=5.7 Hz, 2H), 2.62 (t, J=7.8 Hz, 2H), 1.90–1.75 (m, 2H), 1.75–1.55 (m, 2H), 1.55–1.45 (m, 2H).

EXAMPLE 28(11)

3-[(6-(5-phenylpentyloxy)naphthalen-2-yl)carbonylamino]propanoic acid

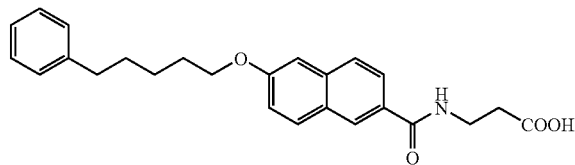

TLC: Rf 0.30 (chloroform:methanol=9:1); NMR (DMSO-d$_6$): δ 12.22 (s, 1H), 8.59 (t, J=5.4. Hz, 1H), 8.34 (s, 1H), 7.90–7.80 (m, 3H), 7.35 (d, J=2.4 Hz, 1H), 7.30–7.10 (m, 6H), 4.10 (t, J=6.6 Hz, 2H), 3.50 (q, J=5.4 Hz, 2H), 2.62 (t, J=7.2 Hz, 2H), 2.55 (t, J=7.2 Hz, 2H), 1.90–1.75 (m, 2H), 1.75–1.60 (m, 2H), 1.55–1.40 (m, 2H).

EXAMPLE 28(12)

2-[3-(4-(5-cyclohexylpentyloxy)phenyl)propanoylamino]acetic acid

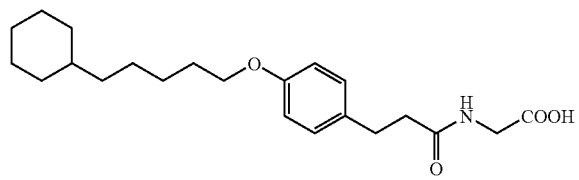

TLC: Rf 0.11 (chloroform:methanol=9:1); NMR (CDCl$_3$): δ 7.09 (d, J=8.6 Hz, 2H), 6.81 (d, J=8.6 Hz, 2H), 6.11 (t, J=5.0 Hz, 1H), 4.04 (d, J=5.0 Hz, 2H), 3.91 (t, J=6.4 Hz, 2H), 2.91 (t, J=7.6 Hz, 2H), 2.54 (t, J=7.6 Hz, 2H), 1.83–1.67 (m, 7H), 1.48–1.09 (m, 10H), 0.93–0.78 (m, 2H).

EXAMPLE 29 ethyl 2-[N-[2-(4-(5-phenylpentyloxy)phenyl)ethyl]carbamoyl]acetate

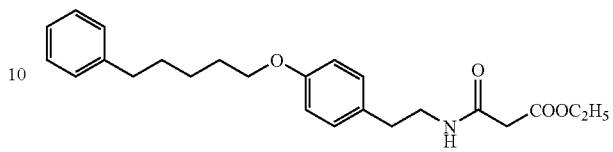

By the same procedure as described in Example 1 using ethyl 3-chloro-3-oxopropionate and 2-[4-(5-phenylpentyloxy)phenyl]ethylamine instead of the compound prepared in Reference Example 3, the compound of the present invention having the following physical data were obtained.

TLC: Rf 0.41 (hexane:ethyl acetate=1:1); NMR (CDCl$_3$): δ 7.32–7.07 (m, 8H), 6.86–6.79 (m, 2H), 4.17 (q, J=7.2 Hz, 2H), 3.93 (t, J=6.6 Hz, 2H), 3.56–3.46 (m, 2H), 3.27 (s, 2H), 2.78 (t, J=7.2 Hz, 2H), 2.64 (t, J=7.2 Hz, 2H), 1.88–1.42 (m, 6H), 1.23 (t, J=7.2 Hz, 3H).

EXAMPLE 30

2-[N-[2-(4-(5-phenylpentyloxy)phenyl)ethyl]carbamoyl]acetic acid

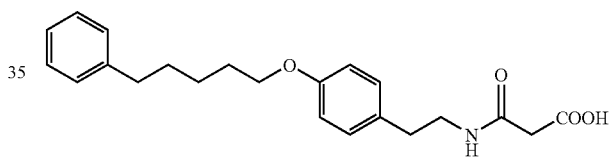

By the same procedure as described in Example 2 using the compound prepared in Example 29 instead of the compound prepared in Example 1, the compound of the present invention having the following physical data were obtained.

TLC: Rf 0.13 (chloroform:methanol=9:1); NMR (CDCl$_3$): δ 7.32–7.05 (m, 7H), 6.83 (d, J=8.6 Hz, 2H), 6.47–6.35 (br, 1H), 3.93 (t, J=6.4 Hz, 2H), 3.60–3.50 (m, 2H), 3.24 (s, 2H), 2.78 (t, J=7.0 Hz, 2H), 2.64 (t, J=7.5 Hz, 2H), 1.88–1.42 (m, 6H).

REFERENCE EXAMPLE 4

3-[4-(5-phenylpentyloxy)phenyl]propanamide

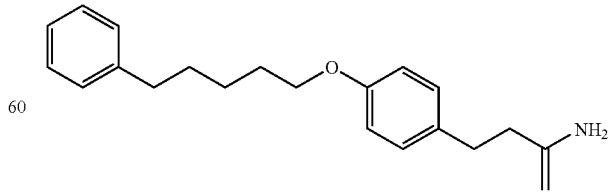

To a solution of the compound prepared in Reference Example 2 (1 g) in dichloromethane (6 mL) was added oxalyl chloride (0.308 mL) and dimethylaformamide (one portion). The reaction mixture was stirred at room temperature for 1 hour. The reaction mixture was concentrated to give acid chloride. To a solution of 28% aqueous ammonia solution (2 mL) in tetrahydrofuran (4 mL) was added a solution of acid chloride in tetrahydrofuran (3 mL) at 0° C. The reaction mixture was stirred at room temperature for 40 minutes. Water was added to the reaction mixture, which was extracted with ethyl acetate. The extract was washed with water and brine, dried over anhydrous sodium sulfate and concentrated. The obtained solid was washed with diethylether and dried to give the title compound (805 mg) having the following physical data.

TLC: Rf 0.50 (chloroform:methanol:acetic acid=100:10:1); NMR (CDCl$_3$): δ 7.30–7.24 (m, 2H), 7.20–7.16 (m, 3H), 7.12 (m, 2H), 6.82 (m, 2H), 5.27 (brs, 2H), 3.92 (t, J=6.6 Hz, 2H), 2.91 (t, J=7.5 Hz, 2H), 2.64 (t, J=7.5 Hz, 2H), 2.50 (t, J=7.5 Hz, 2H), 1.80 (m, 2H), 1.69 (m, 2H), 1.50 (m, 2H).

REFERENCE EXAMPLE 5

3-[4-(5-phenylpentyloxy)phenyl]propylamine

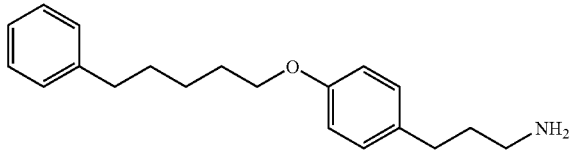

To a suspension of aluminum lithium hydride (146 mg) in tetrahydrofuran (3 mL) was added the compound prepared in Reference 4. The reaction mixture was refluxed for 1 hour. The reaction mixture was cooled to room temperature, then 4N aqueous sodium hydroxide solution (150 μL) and water (450 μL), sequentially. The reaction mixture was stirred at room temperature for 30 minutes. The reaction mixture was dried over anhydrous sodium sulfate and concentrated to give the title compound (713 mg).

REFERENCE EXAMPLE 6 methyl 3-[N-(t-butoxycarbonyl)-3-(4-(5-phenylpentyloxy)phenyl)propylamino]propanoate

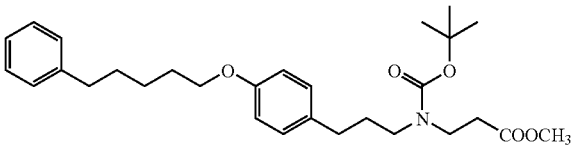

To a solution of the compound prepared in Reference Example 5 (357 mg) in methanol (1.2 mL) was added methyl acrylate (108 μL). The reaction mixture was stirred overnight at room temperature. To the reaction mixture was added tetrahydrofuran (4 mL), di-t-butyl dicarbonate (262 mg) and triethylamine (167 μL). The reaction mixture was stirred at room temperature for 2 hours. The reaction mixture was diluted with ethyl acetate, washed with 1N hydrochloric acid, water and brine, dried over anhydrous sodium sulfate and concentrated. The obtained residue was purified by column chromatography on silica gel (hexane:ethyl acetate=9:1) to give the title compound (340 mg) having the following physical data.

TLC: Rf 0.44 (hexane:ethyl acetate=3:1); NMR (CDC$_3$): δ 7.30–7.24 (m, 2H), 7.20–7.14 (m, 3H), 7.07 (m, 2H), 6.80 (m, 2H), 3.92 (t, J=6.6 Hz, 2H), 3.66 (s, 3H), 3.46 (br, 2H), 3.21 (br, 2H), 2.64 (t, J=7.5 Hz, 2H), 2.60–2.48 (m, 4H), 1.86–1.68 (m, 6H), 1.54–1.44 (m, 11H).

EXAMPLE 31

3-[3-(4-(5-phenylpentyloxy)phenyl)propylamino]propanoic acid hydrochloride

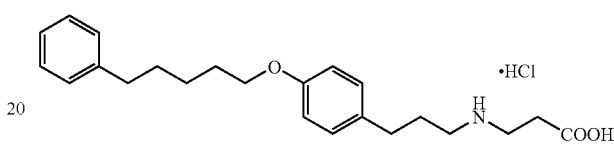

To a solution of the compound prepared in Reference Example 6 (335 mg) in methanol (4 mL) and tetrahydrofuran (2 mL) was added 2N aqueous sodium hydroxide solution (2 mL). The reaction mixture was stirred overnight at room temperature. The reaction mixture was concentrated, diluted with water and washed with diethylether. The aqueous layer was acidified with 2N hydrochloric acid and extracted with ethyl acetate. The extract was washed with water and brine, dried over anhydrous sodium sulfate and concentrated. The residue was dissolved into ethyl acetate (2 mL) and 4N hydrogen chloride/ethyl acetate solution (2 mL) was added thereto. The reaction mixture was stirred at room temperature for 4 hours. The precipitate was filtered, washed with diethylether and dried to give the compound of the present invention (262 mg) having the following data.

TLC: Rf 0.40 (butanol:acetic acid:water=8:1:1); NMR (DMSO-d$_6$): δ 8.70 (brs, 2H), 7.30–7.08 (m, 7H), 6.83 (d, J=8.7 Hz, 2H), 3.90 (t, J=6.6 Hz, 2H), 3.07 (t, J=7.5 Hz, 2H), 2.86 (m, 2H), 2.66–2.52 (m, 6H), 1.90–1.58 (m, 6H), 1.40 (m, 2H).

REFERENCE EXAMPLE 7 methyl 3-[N-(t-butoxycarbonyl)-2-(4-(5-phenylpentyloxy)phenyl)ethylamino]propanoate

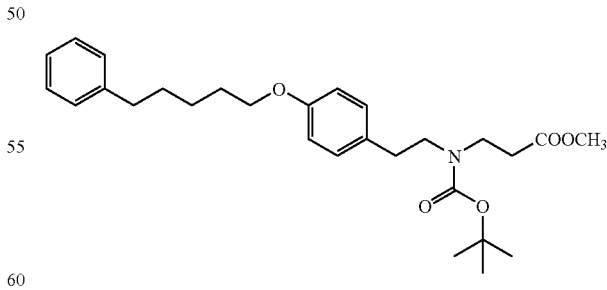

By the same procedure as described in Reference Example 6 using 2-[4-(5-phenylpentyloxy)phenyl]ethylamine instead of the compound prepared in Reference Example 5, the title compound having the following physical data were obtained.

TLC: Rf 0.36 (hexane:ethyl acetate=3:1).

EXAMPLE 32

3-[2-(4-(5-phenylpentyloxy)phenyl)ethylamino]propanoic acid hydrochloride

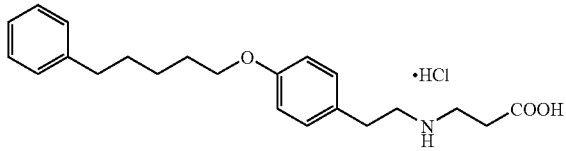

By the same procedure as described in Example 31 using the compound prepared in Reference Example 7, the compound of the present invention having the following physical data were obtained.

TLC: Rf 0.40 (butanol:acetic acid:water=8:1:1); NMR (DMSO-$d_6$): δ 8.80 (brs, 2H), 7.30–7.12 (m, 7H), 6.86 (d, J=8.4 Hz, 2H), 3.91 (t, J=6.6 Hz, 2H), 3.14–3.06 (m, 4H), 2.84 (m, 2H), 2.67 (t, J=7.2 Hz, 2H), 2.58 (t, J=7.5 Hz, 2H), 1.76–1.56 (m, 4H), 1.42 (m, 2H).

REFERENCE EXAMPLE 8

N-(t-butoxycarbonyl)-3-[4-(5-phenylpentyloxy)phenyl]propylamine

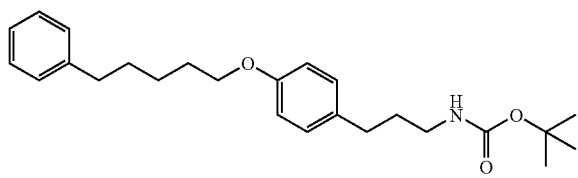

To a solution of the compound prepared in Reference Example 5 (357 mg) in tetrahydrofuran (5 mL) was added di-t-butyl dicarbonate (262 mg) and triethylamine (167 μL). The reaction mixture was stirred overnight at room temperature. The reaction mixture was diluted with ethyl acetate, washed with 1N hydrochloric acid, water and brine, dried over anhydrous sodium sulfate and concentrated. The obtained residue was purified by column chromatography on silica gel (hexane:ethyl acetate=9:1) to give the title compound (410 mg) having the following physical data.

TLC: Rf 0.52 (hexane:ethyl acetate=3:1); NMR (CDCl$_3$): δ 7.30–7.24 (m, 2H), 7.20–7.14 (m, 3H), 7.07 (m, 2H), 6.80 (m, 2H), 4.50 (br, 1H), 3.92 (t, J=6.6 Hz, 2H), 3.13 (m, 2H), 2.64 (t, J=7.5 Hz, 2H), 2.57 (t, J=7.5 Hz, 2H), 1.85–1.64 (m, 6H), 1.54–1.44 (m, 11H).

REFERENCE EXAMPLE 9 methyl 2-[N-(t-butoxycarbonyl)-3-(4-(5-phenylpentyloxy)phenyl)propylamino]acetate

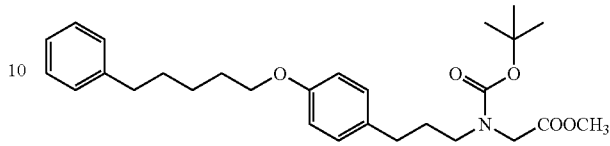

To a solution the compound prepared in Reference Example 8 (397 mg) in tetrahydrofuran (5 mL) was added a solution of 1.0 M lithium hexamethyldisiladide in tetrahydrofuran (1.1 mL) at 0° C. The reaction mixture was stirred at 0° C. for 15 minutes and methyl 2-bromoacetate (99 μL) was added thereto. The reaction mixture was stirred at 0° C. for 1 hour and then at room temperature for 1 hour. The reaction mixture was concentrated, added 1N hydrochloric acid thereto and extracted with ethyl acetate. The extract was washed with water and brine and concentrated to give the title compound having the following physical data.

TLC: Rf 0.46 (hexane:ethyl acetate=3:1).

EXAMPLE 33

2-[N-(t-butoxycarbonyl)-3-(4-(5-phenylpentyloxy)phenyl)propylamino]acetic acid hydrochloride

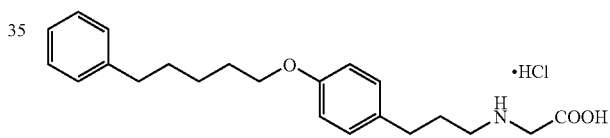

By the same procedure as described in Example 31 using the compound prepared in Reference Example 9, the compound of the present invention having the following physical data were obtained.

TLC: Rf 0.40 (butanol:acetic acid:water=8:1:1); NMR (DMSO-$d_6$): δ 9.00 (brs, 2H), 7.84 (brs, 1H), 7.30–7.06 (m, 7H), 6.82 (d, J=8.7 Hz, 2H), 3.90 (t, J=6.6 Hz, 2H), 3.82 (s, 2H), 2.87 (m, 2H), 2.62–2.50 (m 4H), 1.92–1.56 (m, 6H), 1.42 (m, 2H).

REFERENCE EXAMPLE 10

3-[4-(5-phenylpentyloxy)phenyl]propanol

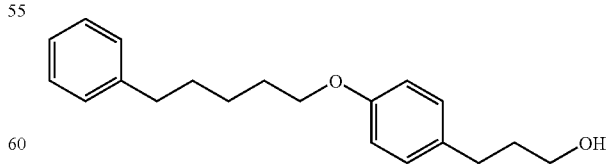

By the same procedure as described in Reference Example 5 using the compound prepared in Reference Example 2, the title compound having the following physical cal data were obtained.

TLC: Rf 0.33 (hexane:ethyl acetate=2:1).

REFERENCE EXAMPLE 11

3-[4-(5-phenylpentyloxy)phenyl]propanal

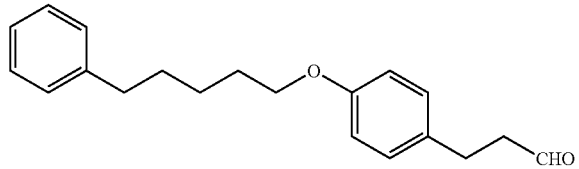

To a solution of the compound prepared in Reference Example 10 (597 mg) in ethyl acetate (10 mL) was added 2,2,6,6-tetramethyl-1-piperidinyloxy free radical (3.1 mg) and potassium bromide (24 mg). A solution of sodium hydrogen carbonate (300 mg) in 2M aqueous sodium hypochlorite solution (1 mL) and water (5 mL) were poured into the reaction mixture at −5° C. The reaction mixture was stirred for 30 minutes. The organic layer was separated, washed with 1.0% aqueous sodium sulfite solution, water and brine, dried over anhydrous sodium sulfate and concentrated to give the title compound (592 mg) having the following physical data.

TLC: Rf 0.63 (hexane:ethyl acetate=2:1); NMR (CDCl$_3$): δ 9.81 (t, J=1.5 Hz, 1H), 7.32–7.06 (m, 7H), 6.81 (m, 2H), 3.92 (t, J=6.6 Hz, 2H), 2.90 (m, 2H), 2.80–2.60 (m, 4H), 1.84–1.42 (m, 6H).

EXAMPLE 34 t-butyl 2-[N-methyl-3-(4-(5-phenylpentyloxy)phenyl)propylamino]acetate hydrochloride

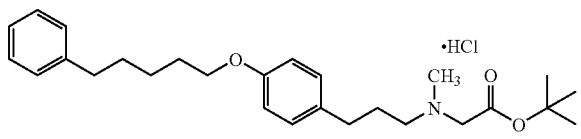

To a solution of the compound prepared in Reference Example 11 (296 mg) and t-butyl sarcosinate hydrochloride in methanol (5 mL) was added sodium cyanoborohydride (63 mg) at 0° C. The reaction mixture was stirred at same temperature for 1 hour. Further, the reaction mixture was stirred overnight at room temperature. Water was added to the reaction mixture, which was concentrated. Ethyl acetate was added to the residue, which was washed with saturated aqueous solution of sodium hydrogen carbonate and brine, dried over anhydrous sodium sulfate and concentrated. The obtained residue was dissolved with diethylether (10 mL) and 1N hydrogen chloride/ethyl acetate solution (1.1 mL) was added thereto. The precipitate was filtered, washed with diethylether and dried to give the compound of the present invention (368 mg) having the following physical data.

TLC: Rf 0.36 (hexane:ethyl acetate=2:1); NMR (DMSO-d$_6$): δ 10.14 (brs, 1H), 7.28–7.08 (m, 7H), 6.83 (m, 2H), 4.06 (brs, 2H), 3.90 (t, J=6.6 Hz, 2H), 3.05 (br, 2H), 2.78 (brs, 3H), 2.60–2.52 (m, 4H) 1.94 (m, 2H), 1.76–1.64 (m, 4H), 1.48–1.38 (m, 11H).

EXAMPLE 35

2-[N-methyl-3-(4-(5-phenylpentyloxy)phenyl)propylamino]acetic acid hydrochloride

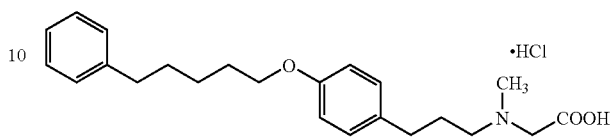

To a solution of the compound prepared in Example 34 (356 mg) in dichloromethane (2 mL) was added trifluoroacetic acid (2 mL). The reaction mixture was stirred at room temperature for 2 hours. The reaction mixture was concentrated. The obtained residue was dissolved with ethyl acetate (2 mL). 4N hydrogen chloride/ethyl acetate solution (0.5 mL) was added thereto and the reaction mixture was concentrated. The obtained residue was recrystallized from methanol-ethyl acetate to give the compound of the present invention (270 mg) having the following physical data.

TLC: Rf 0.28 (butanol: acetic acid:water=8:1:1); NMR (DMSO-d$_6$): δ 7.30–7.09 (m, 7H), 6.83 (d, J=8.7 Hz, 2H), 4.06 (s, 2H), 3.90 (t, J=6.6 Hz, 2H), 3.09 (m, 2H), 2.80 (s, 3H), 2.62–2.50 (m, 4H), 1.92 (m, 2H), 1.78–1.56 (m, 4H), 1.42 (m, 2H).

PREPARATION EXAMPLE 1

The following components were admixed in a conventional method, punched out to give 100 tablets each containing 50 mg of active ingredient.

| | |
|---|---|
| 2-chloro-5-[3-(4-(5-phenylpentyloxy)phenyl)propanoylamino]benzoic acid | 5.0 g |
| calcium carboxymethylcellulose (disintegrant) | 0.2 g |
| magnesium stearate (lubricant) | 0.1 g |
| microcrystalline cellulose | 4.7 g |

PREPARATION EXAMPLE 2

After mixing the following components by a conventional method, the resulting solution was sterilized by a conventional method and 5 ml portions thereof were filled in amples, respectively, and freeze-dried by a conventional method to obtain 100 amples of injection containing each 20 mg of the active ingredient.

| | |
|---|---|
| 2-chloro-5-[3-(4-(5-phenylpentyloxy)phenyl)propanoylamino]benzoic acid | 2.0 g |
| Mannitol | 20 g |
| Distilled water | 500 ml |

The invention claimed is:

1. A pharmaceutical composition comprising a carboxylic acid compound represented by formula (I)

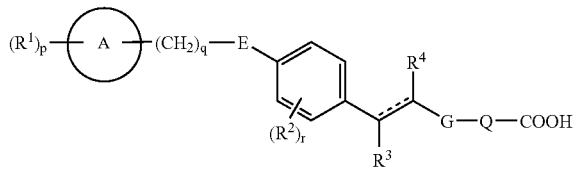

wherein
- $R^1$ is C1–8 alkyl, C1–8 alkoxy, halogen atom, nitro or trifluoromethyl,
- ring A is C5–7 mono-carbocyclic ring or 5–7 membered mono-cyclic hetero ring containing 1–2 nitrogen atoms, one oxygen atom and/or one sulfur atom,
- E is —$CH_2$—, —O—, —S— or —$NR^6$— (wherein $R^6$ is hydrogen or C1–8 alkyl),
- $R^2$ is C1–8 alkyl, C1–8 alkoxy, halogen atom, nitro or trifluoromethyl,
- $R^3$ is hydrogen or C1–8 alkyl,
- $R^4$ is hydrogen or C1–8 alkyl, or
- $R^2$ and $R^4$ taken together form —$CH_2$—$CH_2$— or —CH=CH—,
- G is —$CONR^7$—, —$NR^7CO$—, —$SO_2NR^7$—, —$NR^7SO_2$—, —$CH_2NR^7$— or —$NR^7CH_2$— (wherein $R^7$ is hydrogen, C1–8 alkyl, Cyc1 or C1–8 alkyl substituted by Cyc1, Cyc1 is C5–7 mono-carbocyclic ring or 5–7 membered mono-cyclic hetero ring containing 1–2 nitrogen atoms, one oxygen atom and/or one sulfur atom.),
- Q is C1–4 alkylene or

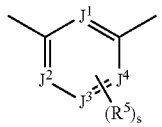

- $J^1$, $J^2$, $J^3$ and $J^4$ are each independently carbon atom or nitrogen atom (with the proviso that the number of nitrogen is less than two),
- $R^5$ is
  (1) C1–8 alkyl,
  (2) halogen atom,
  (3) nitro,
  (4) cyano,
  (5) trifluoromethyl,
  (6) trifluoromethoxy,
  (7) phenyl,
  (8) tetrazolyl,
  (9) —$OR^9$,
  (10) —$SR^{10}$,
  (11) —$COOR^{11}$,
  (12) —$NR^{12}R^{13}$,
  (13) —$CONR^{14}R^{15}$,
  (14) —$SO_2NR^{16}R^{17}$,
  (15) —$NR^{18}COR^{19}$,
  (16) —$NR^{20}SO_2R^{21}$,
  (17) —$SO_2R^{22}$ or
  (18) —$OP(O)(OR^{23})_2$, (wherein $R^9$-$R^{18}$, $R^{20}$ and $R^{23}$ are each independently hydrogen, C1–8 alkyl, Cyc2 or C1–8 alkyl substituted by Cyc2,
$R^{12}$ and $R^{13}$, $R^{14}$ and $R^{15}$, $R^{16}$ and $R^{17}$ together with nitrogen atom to which they are attached, form 5–7 membered mono-cyclic hetero ring containing 1–2 nitrogen atoms, one oxygen atom and/or one sulfur atom (the hetero ring may be optionally substituted by C1–8 alkyl, hydroxy or amino)
$R^{19}$ and $R^{21}$ are each independently C1–8 alkyl, Cyc2 or C1–8 alkyl substituted by Cyc2,
$R^{22}$ is hydroxy, C1–8 alkyl, Cyc2 or C1–8 alkyl substituted by Cyc2, Cyc2 is C5–7 mono-carbocyclic ring or 5–7 membered mono-cyclic hetero ring containing 1–2 nitrogen atoms, one oxygen atom and/or one sulfur atom),
wherein, when Q is

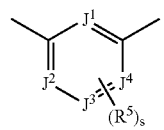

and $J^2$ is carbon atom substituted by $R^5$, G may be

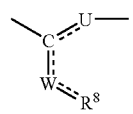

(wherein U is oxygen atom, nitrogen atom or sulfur atom,
W is carbon atom or nitrogen atom,
$R^8$ and $R^5$, which bonds $J^2$, taken together form bond, carbon atom or nitrogen atom),
p is 0 or an integer of 1–5,
q is an integer of 4–6,
r is 0 or an integer of 1–4,
s is 0 or an integer of 1–4, and

----- is single bond or double bond,
a prodrug thereof or a non-toxic salt thereof, wherein said prodrug has a carboxylate ester, a carboxylic amide or an alcohol in place of —COOH in formula (I),
and a pharmaceutically acceptable carrier or diluent.

2. The pharmaceutical composition according to claim 1, wherein the prodrug is a compound represented by formula (IA)

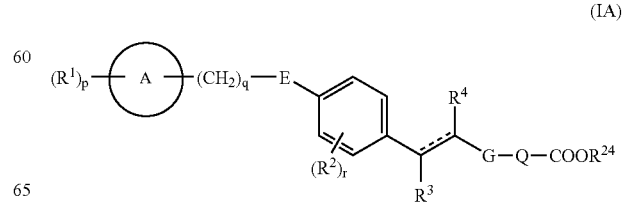

wherein $R^{24}$ is (1) C1–8 alkyl or (2) C1–8 alkyl substituted by 1–2 of hydroxy or amino, and other symbols represent the same meanings as claim 1.

3. The pharmaceutical composition according to claim 1, wherein the prodrug is a compound represented by formula (IB)

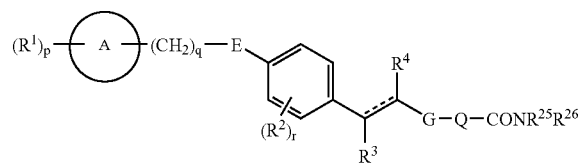

wherein $R^{25}$ and $R^{26}$ are each independently (1) hydrogen, (2) C1–8 alkyl or (3) C1–8 alkyl substituted by 1–2 of hydroxy or amino, and other symbols represent the same meanings as claim 1.

4. The pharmaceutical composition according to claim 1, wherein the prodrug is a compound represented by formula (IC)

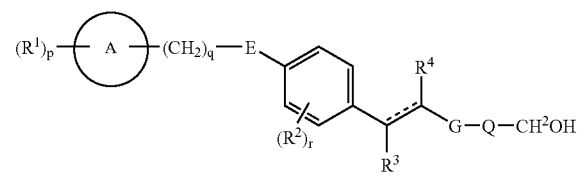

wherein all symbols represent the same meanings as claim 1.

5. The pharmaceutical composition according to claim 1, wherein the prodrug is a compound represented by formula (ID)

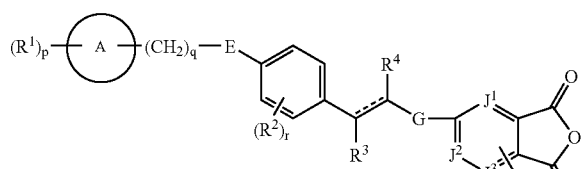

wherein t is 0 or an integer of 1–3, and other symbols represent the same meanings as claim 1.

6. A carboxylic acid compound represented by formula (I)

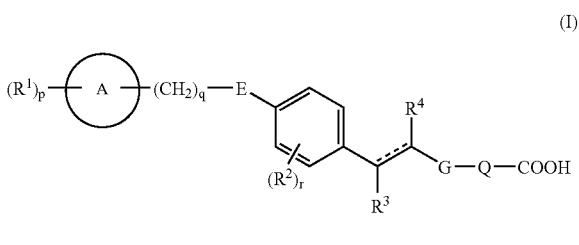

wherein $R^1$ is C1–8 alkyl, C1–8 alkoxy, halogen atom, nitro or trifluoromethyl, ring A is C5–7 mono-carbocyclic ring or 5–7 membered mono-cyclic hetero ring containing 1–2 nitrogen atoms, one oxygen atom and/or one sulfur atom, E is —$CH_2$—, —O—, —S— or —$NR^6$— (wherein $R^6$ is hydrogen or C1–8 alkyl), $R^2$ is C1–8 alkyl, C1–8 alkoxy, halogen atom, nitro or trifluoromethyl, $R^3$ is hydrogen or C1–8 alkyl, $R^4$ is hydrogen or C1–8 alkyl, $R^2$ and $R^4$ taken together form —$CH_2$—$CH_2$— or —CH=CH—, G is —$CONR^7$—, —$NR^7CO$—, —$SO_2NR^7$—, —$NR^7SO_2$—, —$CH_2NR^7$— or —$NR^7CH_2$— (wherein $R^7$ is hydrogen, C1–8 alkyl, Cyc1 or C1–8 alkyl substituted by Cyc1, Cyc1 is C5–7 mono-carbocyclic ring or 5–7 membered mono-cyclic hetero ring containing 1–2 nitrogen atoms, one oxygen atom and/or one sulfur atom), Q is C1–4 alkylene or

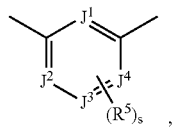

$J^1$, $J^2$, $J^3$ and $J^4$ are each independently carbon atom or nitrogen atom (with the proviso that the number of nitrogen is less than two), $R^5$ is
(1) C1–8 alkyl,
(2) halogen atom,
(3) nitro,
(4) cyano,
(5) trifluoromethyl,
(6) trifluoromethoxy,
(7) phenyl,
(8) tetrazolyl,
(9) —$OR^9$,
(10) —$SR^{10}$,
(11) —$COOR^{11}$,
(12) —$NR^{12}R^{13}$,
(13) —$CONR^{14}R^{15}$,
(14) —$SO_2NR^{16}R^{17}$,
(15) —$NR^{18}COR^{19}$,
(16) —$NR^{20}SO_2R^{21}$,
(17) —$SO_2R^{22}$ or
(18) —$OP(O)(OR^{23})_2$, (wherein R⁹–R¹⁸, R²⁰ and R²³ are each independently hydrogen, C1–8 alkyl, Cyc2 or C1–8 alkyl substituted by Cyc2, R¹² and R¹³, R¹⁴ and R¹⁵, R¹⁶ and R¹⁷ together with nitrogen atom to which they are attached, form 5–7 membered mono-cyclic hetero ring containing 1–2 nitrogen atoms, one oxygen atom and/or one sulfur atom (the hetero ring may be optionally substituted by C1–8 alkyl, hydroxy or amino)

R¹⁹ and R²¹ are each independently C1–8 alkyl, Cyc2 or C1–8 alkyl substituted by Cyc2, R²² is hydroxy, C1–8 alkyl, Cyc2 or C1–8 alkyl substituted by Cyc2, Cyc2 is C5–7 mono-carbocyclic ring or 5–7 membered mono-cyclic hetero ring containing 1–2 nitrogen atoms, one oxygen atom and/or one sulfur atom), wherein, when Q is

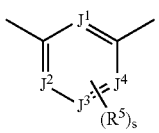

and J² is carbon atom substituted by R⁵, G may be

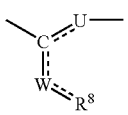

(wherein U is oxygen atom, nitrogen atom or sulfur atom, W is carbon atom or nitrogen atom, R⁸ and R⁵, which bonds J², taken together form bond, carbon atom or nitrogen atom), p is 0 or an integer of 1–5,
q is an integer of 4–6,
r is 0 or an integer of 1–4,
s is 0 or an integer of 1–4, and

----- is single bond or double bond, a prodrug thereof or a non-toxic salt thereof, wherein said prodrug has a carboxylate ester, a carboxylic amide or an alcohol in place of —COOH in formula (I).

7. The prodrug of the compound represented by formula (I) according to claim 6 which is a compound represented by formula (IA)

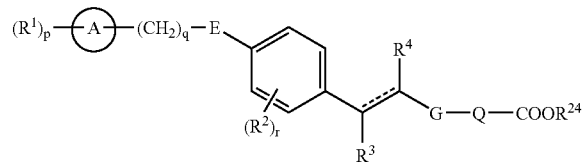

wherein R²⁴ is (1) C1–8 alkyl or (2) C1–8 alkyl substituted by 1–2 of hydroxy or amino, and other symbols represent the same meanings as claim 6.

8. The prodrug of the compound represented by formula (I) according to claim 6 which is a compound represented by formula (IB)

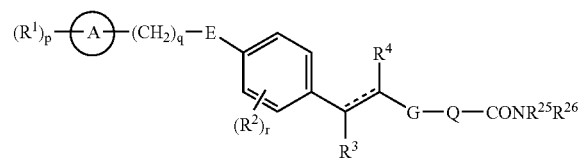

wherein R²⁵ and R²⁶ are each independently (1) hydrogen, (2) C1–8 alkyl or (3) C1–8 alkyl substituted by 1–2 of hydroxy or amino, and other symbols represent the same meanings as claim 6.

9. The prodrug of the compound represented by formula (I) according to claim 6 which is a compound represented by formula (IC)

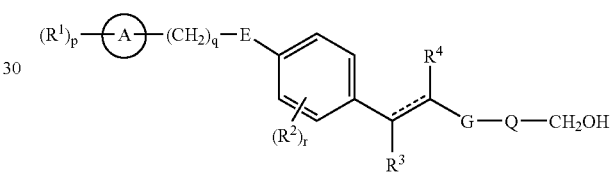

wherein all symbols represent the same meanings as claim 6.

10. The prodrug of the compound represented by formula (I) according to claim 6 which is a compound represented by formula (ID)

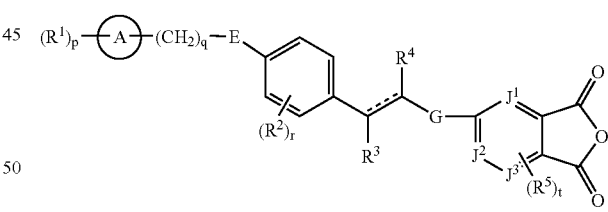

wherein t is 0 or an integer of 1–3, and other symbols represent the same meanings as claim 6.

11. The compound according to claim 6 wherein Q is C1–4 alkyl.

12. The compound according to claim 6 wherein Q is

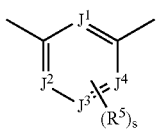

13. The compound according to claim 11 which is
(1) 2-[3-(4-(6-phenylhexyl)phenyl)propanoylamino]acetic acid,
(2) 3-[3-(4-(6-phenylhexyl)phenyl)propanoylamino]propanoic acid,
(3) 2-[3-(4-(5-phenylpentyloxy)phenyl)propanoylamino]acetic acid,
(4) 3-[3-(4-(5-phenylpentyloxy)phenyl)propanoylamino]propanoic acid,
(5) 4-[3-(4-(5-phenylpentyloxy)phenyl)propanoylamino]butanoic acid,
(6) 4-[3-(4-(6-phenylhexyl)phenyl)propanoylamino]butanoic acid,
(7) 2-[N-methyl-3-(4-(5-phenylpentyloxy)phenyl)propanoylamino]acetic acid,
(8) 2-[N-(pyridin-2-yl)methyl-3-(4-(5-phenylpentyloxy)phenyl)propanoylamino]acetic acid,
(9) 2-[3-(4-(4-phenylbutoxy)phenyl)-2-propenoylamino]acetic acid,
(10) 3-[3-(4-(4-phenylbutoxy)phenyl)-2-propenoylamino]propanoic acid,
(11) 2-[(6-(5-phenylpentyloxy)naphthalen-2-yl)carbonylamino]acetic acid,
(12) 3-[(6-(5-phenylpentyloxy)naphthalen-2-yl)carbonylamino]propanoic acid,
(13) 2-[3-(4-(5-cyclohexylpentyloxy)phenyl)propanoylamino]acetic acid,
(14) 2-[N-[2-(4-(5-phenylpentyloxy)phenyl)ethyl]carbamoyl]acetic acid,
(15) 3-[3-(4-(5-phenylpentyloxy)phenyl)propylamino]propanoic acid,
(16) 3-[2-(4-(5-phenylpentyloxy)phenyl)ethylamino]propanoic acid,
(17) 2-[N-(t-butoxycarbonyl)-3-(4-(5-phenylpentyloxy)phenyl)propylamino]acetic acid or
(18) 2-[N-methyl-3-(4-(5-phenylpentyloxy)phenyl)propylamino]acetic acid,
a prodrug thereof or a non-toxic salt thereof.

14. The compound according to claim 12 which is
(1) 2-methoxy-5-[3-(4-(5-phenylpentyloxy)phenyl)propanoylamino]benzoic acid,
(2) 2-chloro-5-[3-(4-(5-phenylpentyloxy)phenyl)propanoylamino]benzoic acid,
(3) 2-bromo-5-[3-(4-(5-phenylpentyloxy)phenyl)propanoylamino]benzoic acid,
(4) 2-carboxy-5-[3-(4-(5-phenylpentyloxy)phenyl)propanoylamino]benzoic acid,
(5) 3-carboxy-5-[3-(4-(5-phenylpentyloxy)phenyl)propanoylamino]benzoic acid,
(6) 2-methylthio-5-[3-(4-(5-phenylpentyloxy)phenyl)propanoylamino]benzoic acid,
(7) 3-[3-(4-(5-phenylpentyloxy)phenyl)propanoylamino]benzoic acid,
(8) 3-[N-(pyridin-2-yl)methyl-3-(4-(5-phenylpentyloxy)phenyl)propanoylamino]benzoic acid,
(9) 3-chloro-5-[3-(4-(5-phenylpentyloxy)phenyl)propanoylamino]benzoic acid,
(10) 2-(morpholin-4-yl)-5-[3-(4-(5-phenylpentyloxyphenyl)propanoylamino]benzoic acid,
(11) 2-(pyrrolidin-1-yl)-5-[3-(4-(5-phenylpentyloxy)phenyl)propanoylamino]benzoic acid,
(12) 6-[3-(4-(5-phenylpentyloxy)phenyl)propanoylamino]pyridin-2-carboxylic acid,
(13) 2-[3-(4-(5-phenylpentyloxy)phenyl)propanoylamino]pyridin-4-carboxylic acid,
(14) 4-chloro-3-[3-(4-(5-phenylpentyloxy)phenyl)propanoylamino]benzoic acid,
(15) 4-methoxy-3-[3-(4-(5-phenylpentyloxy)phenyl)propanoylamino]benzoic acid,
(16) 2-hydroxy-5-[3-(4-(5-phenylpentyloxy)phenyl)propanoylamino]benzoic acid,
(17) 2-methyl-5-[3-(4-(5-phenylpentyloxy)phenyl)propanoylamino]benzoic acid,
(18) 2-fluoro-5-[3-(4-(5-phenylpentyloxy)phenyl)propanoylamino]benzoic acid,
(19) 2-chloro-3-[3-(4-(5-phenylpentyloxy)phenyl)propanoylamino]benzoic acid,
(20) 2-nitro-5-[3-(4-(5-phenylpentyloxy)phenyl)propanoylamino]benzoic acid,
(21) 2-(N,N-diethylamino)-5-[3-(4-(5-phenylpentyloxy)phenyl)propanoylamino]benzoic acid,
(22) 2-(2,6-dimethylmorpholin-4-yl)-5-[3-(4-(5-phenylpentyloxy)phenyl)propanoylamino]benzoic acid,
(23) 2-(N-acetylamino)-5-[3-(4-(5-phenylpentyloxy)phenyl)propanoylamino]benzoic acid,
(24) 2-(N,N-dimethylamino)-5-[3-(4-(5-phenylpentyloxy)phenyl)propanoylamino]benzoic acid,
(25) 4-[3-(4-(5-phenylpentyloxy)phenyl)propanoylamino]pyridin-2-carboxylic acid,
(26) 2-chloro-5-[3-(2-methoxy-4-(5-phenylpentyloxy)phenyl)propanoylamino]benzoic acid,
(27) 2-chloro-5-[3-(2-methyl-4-(5-phenylpentyloxy)phenyl)propanoylamino]benzoic acid,
(28) methyl 2-chloro-5-[3-(2-fluoro-4-(5-phenylpentyloxy)phenyl)propanoylamino]benzoic acid,
(29) 2-carboxy-5-[3-(2-methyl-4-(5-phenylpentyloxy)phenyl)propanoylamino]benzoic acid,
(30) 2-carboxy-5-[3-(2-fluoro-4-(5-phenylpentyloxy)phenyl)propanoylamino]benzoic acid,
(31) 2-carboxy-5-[3-(2-methoxy-4-(5-phenylpentyloxy)phenyl)propanoylamino]benzoic acid,
(32) 2-carboxy-5-[3-(3-methoxy-4-(5-phenylpentyloxy)phenyl)propanoylamino]benzoic acid,
(33) 2-chloro-5-[3-(3-methoxy-4-(5-phenylpentyloxy)phenyl)propanoylamino]benzoic acid,
(34) 2-carboxy-5-[3-(4-(4-phenylbutyloxy)phenyl)propanoylamino]benzoic acid,
(35) 2-carboxy-5-[3-(4-(6-phenylhexyloxy)phenyl)propanoylamino]benzoic acid,
(36) 2-chloro-5-[3-(4-(5-phenylpentylthio)phenyl)propanoylamino]benzoic acid,
(37) 2-chloro-5-[3-(4-(5-phenylpentylamino)phenyl)propanoylamino]benzoic acid,
(38) 3-[3-(4-(6-phenylhexyl)phenyl)propanoylamino]benzoic acid,
(39) 3-[3-(4-(5-cyclohexylpentyloxy)phenyl)propanoylamino]benzoic acid,
(40) 2-chloro-5-[3-(4-(4-(4-methylphenyl)butyloxy)phenyl)propanoylamino]benzoic acid,
(41) 2-chloro-5-[3-(4-(4-(4-methoxyphenyl)butyloxy)phenyl)propanoylamino]benzoic acid,
(42) 2-carboxy-5-[3-(4-(4-(4-methoxyphenyl)butyloxy)phenyl)propanoylamino]benzoic acid,
(43) 2-chloro-5-[3-(2-methoxy-4-(5-(pyridin-4-yl)pentyloxy)phenyl)propanoylamino]benzoic acid,
(44) 2,3-dichloro-5-[3-(4-(5-phenylpentyloxy)phenyl)propanoylamino]benzoic acid,
(45) 2-methoxy-3-carboxy-5-[3-(4-(5-phenylpentyloxy)phenyl)propanoylamino]benzoic acid,
(46) 2-nitro-5-[3-(3-methoxy-4-(5-phenylpentyloxy)phenyl)propanoylamino]benzoic acid,
(47) 2-chloro-3-[3-(4-(5-(thiophen-2-yl)pentyloxy)phenyl)propanoylamino]benzoic acid,

(48) 2-chloro-5-[(6-(5-phenylpentyloxy)naphthalen-2-yl)carbonylamino]benzoic acid,
(49) 2-chloro-5-[3-(4-(5-(4-methylphenyl)pentyloxy)phenyl)propanoylamino]benzoic acid,
(50) 2-chloro-5-[2-methyl-3-(4-(5-phenylpentyloxy)phenyl)propanoylamino]benzoic acid,
(51) 2-chloro-5-[3-(4-(4-phenylbutyloxy)phenyl)propanoylamino]benzoic acid,
(52) 2-chloro-5-[3-(4-(6-phenylhexyloxy)phenyl)propanoylamino]benzoic acid,
(53) 2-chloro-5-[3-(4-(5-phenylpentyloxy)phenyl)-(2E)-propenoylamino]benzoic acid,
(54) 2-amino-5-[3-(4-(5-phenylpentyloxy)phenyl)propanoylamino]benzoic acid,
(55) 2-amino-5-[3-(3-methoxy-4-(5-phenylpentyloxy)phenyl)propanoylamino]benzoic acid,
(56) 2-chloro-5-[N-methyl-3-(4-(5-phenylpentyloxy)phenyl)propanoylamino]benzoic acid,
(57) 2-chloro-5-[2-(4-(5-phenylpentyloxy)phenyl)ethylaminocarbonyl]benzoic acid,
(58) 3-[2-(4-(5-phenylpentyloxy)phenyl)ethylaminocarbonyl]benzoic acid,
(59) 2-fluoro-5-[2-(4-(5-phenylpentyloxy)phenyl)ethylaminocarbonyl]benzoic acid,
(60) 5-[2-(4-(5-phenylpentyloxy)phenyl)ethylaminocarbonyl]pyridin-3-carboxylic acid,
(61) 2-nitro-5-[2-(4-(5-phenylpentyloxy)phenyl)ethylaminocarbonyl]benzoic acid,
(62) 3-carboxy-5-[2-(4-(5-phenylpentyloxy)phenyl)ethylaminocarbonyl]benzoic acid,
(63) 6-[2-(4-(5-phenylpentyloxy)phenyl)ethylaminocarbonyl]pyridin-2-carboxylic acid,
(64) 4-chloro-3-[2-(4-(5-phenylpentyloxy)phenyl)ethylaminocarbonyl]benzoic acid,
(65) 4-[2-(4-(5-phenylpentyloxy)phenyl)ethylaminocarbonyl]pyridin-2-carboxylic acid,
(66) 2-carboxy-5-[2-(4-(5-phenylpentyloxy)phenyl)ethylaminocarbonyl]benzoic acid,
(67) 2-amino-5-[2-(4-(5-phenylpentyloxy)phenyl)ethylaminocarbonyl]benzoic acid,
(68) 2-carboxy-5-[3-(4-(5-phenylpentyloxy)phenyl)propylamino]benzoic acid,
(69) 2-chloro-5-[3-(4-(5-phenylpentyloxy)phenyl)propylamino]benzoic acid,
(70) 3-[2-(4-(5-phenylpentyloxy)phenyl)ethylaminosulfonyl]benzoic acid or
(71) 2-[2-(4-(5-phenylpentyloxy)phenyl)ethyl]benzoimidazol-5-carboxylic acid,
a prodrug thereof or a non-toxic salt thereof.

* * * * *